United States Patent
Gatanaga et al.

(10) Patent No.: US 6,593,456 B1
(45) Date of Patent: Jul. 15, 2003

(54) TUMOR NECROSIS FACTOR RECEPTOR RELEASING ENZYME

(75) Inventors: Tetsuya Gatanaga, Irvine, CA (US); Gale A. Granger, Laguna Beach, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/081,385

(22) Filed: May 14, 1998

Related U.S. Application Data

(63) Continuation-in-part of application No. 08/964,747, filed on Nov. 5, 1997.
(60) Provisional application No. 60/030,761, filed on Nov. 6, 1996.

(51) Int. Cl.$^7$ .................................................. C07K 1/00
(52) U.S. Cl. ....................... 530/350; 435/69.1; 435/7.2; 536/23.5
(58) Field of Search ........................ 530/350; 536/23.5; 435/69.1, 7.2

(56) References Cited

U.S. PATENT DOCUMENTS

| | | |
|---|---|---|
| 4,761,371 A | 8/1988 | Bell et al. |
| 5,395,760 A | 3/1995 | Smith et al. ............. 435/240.1 |
| 6,083,913 A | 7/2000 | Dower et al. |

FOREIGN PATENT DOCUMENTS

| | | | |
|---|---|---|---|
| EP | 0 657 536 A1 | | 6/1995 |
| EP | 418 014 | | 12/1995 |
| WO | WO 9401548 | * | 1/1994 |
| WO | WO 95/31544 | | 11/1995 |
| WO | WO 95/33051 | | 12/1995 |
| WO | WO 96/10642 | | 1/1996 |

OTHER PUBLICATIONS

Gonzalez, I.L. et al. Variation among human 28S ribosomal RNA genes. P roc. Natl. Acad. Sci. USA 82, 7666–7670 (1985).*

Leffers, H. The sequence of 28S ribosomal RNA varies within and between human cell lines. Nucleic Acid Research. 21(6), 1449–1455 (1993).*

Hillier, L. et al. Generation and analysis of 280,000 human expressed sequence tags. Genome Research. 6(9), 807–828 (1996).*

Morgan, D.O. et al. Insulin–like growth factor II receptor as a multifunctional binding protein. Nature. 329(6137) 301–307 (1987).*

Minet, M. et al. Cloning and sequencing of a human cDNA coding for a multifunctional polypeptide of the purine pathway by complementation of the ade2–101 mutant in *Saccharomyces cerevisiae*. Curr. Genet. 18:287–291 (1990).*

Nagfuchi et al. Structure and Expression of the gene responsible for the triplet repeat disorder, dentatorubral and pallidoluysian atrophy (DRPLA) Nature Genetics, vol. 8, pp. 177–182.*

Mikayama T. Molecular cloning and functional expression of a cDNA encoding glycosylation–inhibition factor. Proc. Natl. Acad. Sci. USA vol. 90, pp. 10056–10060, 1993.*

Voet et al. Biochemistry. 1990. John Wiley & Sons, Inc.. pp. 126–128 and 228–234.*

Abraham et al., "p55 tumor necrosis factor receptor fusion protein in the treatment of patients with severe sepsis and septic shock" (1997) *JAMA* 277:1531–1538.

Aderka et al., "Increased serum levels of soluble receptors for tumor necrosis factor in cancer patients" (1991) *Cancer Res.* 51:5602–5607.

Aderka et al., "Variation in serum levels of the soluble TNF receptors among healthy individuals" (1992) *Lymphokine Cytokine Res.* 11:157–159.

Alderson et al., "Regulation of human monocyte cell–surface and soluble CD23 (FCεRII) by granulocyte–macrophage colony–stimulating factor and IL–3" (1992) *J. Immunol.* 149:1252–1257.

Arbós et al., "Effects of tumour necrosis factor–α (cachectin) on glucose metabolism in the rat" (1992) *Mol. Cell. Biochem.* 112:53–59.

Argilés et al., "Journey from cachexia to obesity by TNF" (1997) *FASEB J.* 11:743–751.

Argilés et al., "The metabolic environment of cancer" (1988) *Mol. Cell. Biochem.* 81:3–17.

Armitage,R., "Tumor necrosis factor receptor superfamily members and their ligands" (1994) *Curr. Opin. Immunol.* 6:407–413.

Arner, P. "Obesity and Insulin Resistance in Swedish Subjects" (1996) *Diabetes Metab.* 13:S85–S86.

Ashkenazi et al., "Protection against endotoxic shock by a tumor necrosis factor receptor immunoadhesin" (1991) *Proc. Natl. Acad. Sci. USA* 88:10535–10539.

(List continued on next page.)

Primary Examiner—Yvonne Eyler
Assistant Examiner—Joseph Murphy
(74) Attorney, Agent, or Firm—Bozicevic, Field & Francis LLP; Carol L. Francis

(57) ABSTRACT

The present invention relates to methods of regulating TNF receptor releasing enzyme (TRRE) activity. Composition altering TRRE activity, including a family of proteins and the genes encoding these proteins having TRRE activity, are provided. These proteins, RNA products, or DNA sequences can be administered to individuals suffering from a disease characterized by abnormal TRRE activity. In the case of diseases associated with elevated levels of TNF, such as rheumatoid arthritis, an inhibitor of TRRE is administered to the disease site to decrease the local levels of TNF. Methods of isolating other compositons which increase or decrease TRRE activity are also provided.

31 Claims, 5 Drawing Sheets

OTHER PUBLICATIONS

Banner et al., "Crystal structure of the soluble human 55 kd receptor–human TNFβ complex: Implications for TNF receptor activation" (1993) *Cell* 73:431–445.

Baran et al., "Characterization of the soluble murine IL–2R and estimation of its affinity for IL–2" (1988) *J. Immunol.* 141:539–546.

Bauditz et al., "Treatment with tumour necrosis factor inhibitor oxpentifylline does not improve corticosteroid dependent chronic active Crohn's disease" (1997) *Gut* 40:470–474.

Baum et al., "Molecular characterization of murine and human OX40/OX40 ligand systems: identification of a human OX40 ligand as the HTLV–1–regulated protein gp34" (1994) *EMBO J.* 13:3992–4001.

Beretz et al., "Modulation by cytokines of leukocyte–endothelial cell interactions, implications for thrombosis" (1990) *Biorheology* 27:455–460.

Bermudez et al., "Effect of stress–related hormones on macrophage receptors and response to tumor necrosis factor" (1990) *Lymphokine Res.* 9:137–145.

Beutler et al., "Passive immunization against cachectin/tumor necrosis factor protects mice from lethal effect of endotoxin" (1985) *Science* 229:869–871.

Bianchi et al., "Increased Brown adipose tissue activity in children with malignant disease" (1989) *Horm. Metab. Res.* 21:640–641.

Birkedal–Hansen et al., "Matrix metalloproteinases: A review" (1993) *Crit. Rev. Oral Biol. Med.* 4:197–250.

Bogdan et al., "Macrophage deactivation by interleukin 10" (1991) *J. Exp. Med.* 174:1549–1555.

Brockhaus et al., "Identification of two types of tumor necrosis factor receptors on human cell lines by monoclonal antibodies" (1990) *Proc. Natl. Acad. Sci. USA* 87:3127–3131.

Buck et al., "Tumor necrosis factor–α inhibits collagen α1(1) gene expression and wound healing in a murine model of cachexia" (1996) *Am. J. Pathol.* 149:195–204.

Calvano et al., "Monocyte tumor necrosis factor receptor levels as a predictor of risk in human sepsis" (1996) *Arch. Surg.* 131:434–437.

Chitambar, "Shedding of transferrin receptor from rat reticulocytes during maturation in vitro: Soluble transferrin receptor is derived from receptor shed in vesicles" (1991) *Blood* 78:2444–2450.

Colotta et al., "Interleukin–1 type II receptor: A decoy target for IL–1 that is regulated by IL–4" (1993) *Science* 261:472–475.

Corcoran et al., "Characterization of ligand binding by the human p55 tumour–necrosis–factor receptor" (1994) *Eur. J. Biochem.* 223:831–840.

Cornelius et al., "Regulation of lipoprotein lipase mRNA content in 3T3–L1 cells by tumour necrosis factor" (1988) *Biochem. J.* 249:765–769.

Cosman, "A family of ligands for the TNF receptor superfamily" (1994) *Stem Cells* (Dayt.) 12:440–455.

Costelli et al., "Tumor necrosis factor–α mediates changes in tissue protein turnover in a rat cancer cachexia model" (1993) *J. Clin. Invest.* 92:2783–2789.

Crowe et al., "A metalloprotease inhibitor blocks shedding of the 80–kD TNF receptor and TNF processing in T lymphocytes" (1995) *J. Exp. Med.* 181:1205–1210.

de Waal Malefyt et al., "Interleukin 10(IL–10) inhibits cytokine synthesis by human monocytes: An autoregulatory role of IL–10 produced by monocytes" (1991) *J. Exp. Med.* 174:1209–1220.

Dean et al., "Evidence for metalloproteinase and metalloproteinase inhibitor imbalance in human osteoarthritic cartilage" (1989) *J. Clin. Invest.* 84:678–685.

Dembic et al. "Two human TNF receptors have similar extracellular, but distinct intracellular, domain sequences" (1990) *Cytokine* 2:231–237.

Derkx et al., "High levels of interleukin–10 during the initial phase of fulminant meningococcal septic shock" (1995) *J. Infect Dis.* 171:229–232.

Dessi et al. "Perturbations of triglycerides but not of cholesterol metabolism are prevented by anti–tumour necrosis factor treatment in rats bearing an ascites hepatoma (Yoshida AH–130)" (1995) *Br. J. Cancer* 72:1138–1143.

Dett et al., "Enhancement of lymphokine–activated T killer cell tumor necrosis factor receptor mRNA transcription, tumor necrosis factor receptor membrane expression, and tumor necrosis factor/lymphotoxin release by IL–1β, IL–4, and IL–6 in vitro" (1991) *J. Immunol.* 146:1522–1526.

Diez–Ruiz et al., "Soluble receptors for tumour necrosis factor in clinical laboratory diagnosis" (1995) *Eur. J. Haematol.* 54:1–8.

Driscoll, K., "Macrophage inflammatory proteins" (1994) *Exp. Lung Res.* 20:474–490.

Dubravec et al., "Circulating human peripheral blood granulocytes synthesis and secrete tumor necrosis factor α" (1990) *Proc. Natl. Acad. Sci. USA* 87:6758–6761.

Durez et al., "In vivo induction of interleukin 10 by anti–CD3 monoclonal antibody or bacterial lipopolysaccharide: Differential modulation by cyclosporin A" (1993) *J. Exp. Med.* 177:551–555.

Echtenacher et al., "Critical protective role of mast cells in a model of acute septic peritonitis" (1996) *Nature* 381:75–77.

Engelmann et al., "A tumor necrosis factor–binding protein purified to homogeneity from human urine protects cells from tumor necrosis factor toxicity" (1989) *J. Biol. Chem.* 264:11974–11980.

Engelmann et al., "Two tumor necrosis factor–binding proteins purified from human urine" (1990) *J. Biol. Chem.* 265:1531–1536.

Ertel et al., "Increased release of soluble tumor necrosis factor receptors into blood during clinical sepsis" (1994) *Arch. Surg.* 129:1330–1337.

Evans et al., "Tumour nectosis factor I (cachectin) mimics some of the effects of tumour growth on the disposal of a [$^{14}$C]lipid load in virgin, lactating and litter–removed rats" (1988) *Biochem. J.* 256:1055–1058.

Fargeas et al., "Central action of interleukin 1∂ on intestinal motility in rats: Mediation by two mechanisms" (1993) *Gastroenterology* 104:377–383.

Feingold et al., "Stimulation of lipolysis in cultured fat cells by tumor necrosis factor, interleukin–1, and the interferons is blocked by inhibition of prostaglandin synthesis" (1992) *Endocrinology* 130:10–16.

Fenner, H., "TNF–inhibitoren: Eine neue therapeutische perspektive bei chronisch–entzündlichen Erkrankungen in der Rheumatologie?" (English abstract included) (1995) *Z. Rheumatol.* 54:158–164.

Ferrante, "Activation of neutrophils by interleukins–1 and – 2 and tumor necrosis factors" (1992) *Immunol. Ser.* 57:417–436.

Fiers, "Tumor necrosis factor: Characterization at the molecular, cellular and in vivo level"(1991) *FEBS Lett.* 285:199–212.

Fiorentino et al., "IL–10 inhibits cytokine production by activated macrophages" (1991) *J. Immunol.* 147:3815–3822.

Fisher et al., "Treatment of septic shock with the tumor necrosis factor receptor:Fc fusion protein" (1996) *N. Engl. J. Med.* 334:1697–1702.

Fried et al., "Cachectin/tumor necrosis factor decreases human adipose tissue lipoprotein lipase mRNA levels, synthesis, and activity" (1989) *J. Lipid. Res.* 30:1917–1923.

Fukunaga et al., "Three different mRNAs encoding human granulocyte colony–stimulating factor receptor" (1990) *Proc. Natl. Acad. Sci. USA* 87:8702–8706.

Garcia–Martinez et al., "Tumour necrosis factor–I increased the ubiquitinization of rat skeletal muscle proteins" (1993) *FEBS Lett.* 323:211–214.

Gatanaga, et al., "Release of soluble TNF/LT receptors from a human ovarian tumor cell line (PA–1) by stimulation with cytokines in vitro" (1993) *Lymphokine and Cytokine Res.* 12:249–253.

Gatanaga et al., "Identification of TNF–LT blocking factor(s) in the serum and ultrafiltrates of human cancer patients" (1990) *Lymphokine Res.* 9:225–229.

Gatanaga et al., "Purification and characterization of an inhibitor (soluble tumor necrosis factor receptor) for tumor necrosis factor and lymphotoxin obtained from the serum ultrafiltrates of human cancer patients" (1990) *Proc. Natl. Acad. Sci USA* 87:8781–8784.

Gatanaga et al., "The regulation of TNF receptor mRNA synthesis, membrane expression, and release by PMA– and LPS–stimulated human monocytic THP–1 cells in vitro" (1991) *Cell Immunol.* 138:1–10.

Gearing et al., "Processing of tumour necrosis factor–I precursor by metalloproteinases" (1994) *Nature* 370:555–557.

Gearing et al., "Matrix metalloproteinases and processing of pro–TNF–$_I$" (1995) *J. Leukoc. Biol.* 57:774–777.

Gehr et al., "Both tumor necrosis factor receptors types mediate proliferative signals in human mononuclear cell activation" (1992) *J. Immunol.* 149:911–917.

Gérard et al., "Interleukin 10 reduces the release of tumor necrosis factor and prevents lethality in experimental endotoxemia" (1993) *J. Exp. Med.* 177:547–550.

Golstein et al., "Cell death mechanisms and the immune system" (1991) *Immunol. Rev.* 121:29–65.

Goodman, "Tumor necrosis factor induces skeletal muscle protein breakdown in rats" (1991) *Am. J. Physiol.* 260:E727–E730.

Goodwin et al., "Cloning of the human and murine interleukin–7 receptors: Demonstration of a soluble form and homology to a new receptor superfamily" (1990) *Cell* 60:941–951.

Gorton et al., "Mast cells as a source of both preformed and immunologically inducible TNF–$_I$/cachetin" (1990) *Nature* 346:274–276.

Grau et al., "Tumor necrosis factor (cachectin) as an essential mediator in murine cerebral malaria" (1987) *Science* 237:1210–1212.

Grell et al., "Segregation of APO–1/Fas antigen– and tumor necrosis factor receptor–mediated apoptosis" (1994) *Euro. J. Immunol.* 24:2563–2566.

Grosen et al., "Measurement of the soluble membrane receptors for tumor necrosis factor and lymphotoxin in the sera of patients with gynecologic malignancy" (1993) *Gynecol. Oncol.* 50:68–77.

Grunfeld et al., "Endotoxin and cytokines induce expression of leptin, the ob gene product, in hamsters" (1996) *J. Clin. Invest.* 97:2152–2157.

Gullberg et al., "Involvement of an Asn/Val cleavage site in the production of a soluble form of a human tumor necrosis factor (TNF) receptor. Site–directed mutagenesis of a putative cleavage site in the p55 TNF receptor chain" *Eur. J. Cell. Biol.* (1992) 58:307–312.

Hahne et al., "A novel soluble form of mouse VCAM–1 is generated from a glycolipid–anchored splicing variant" (1994) *Eur. J. Immunol.* 24:421–428.

Halwachs et al., "Serum levels of the soluble receptor for tumor necrosis factor in patients with renal disease" (1994) *Clin. Investig.* 72:473–476.

Hauner et al., "Effects of tumour necrosis factor alpha ($TNF_I$) on glucose transport and lipid metabolism of newly–differentiated human fat cells in cell culture" (1995) *Diabetologia* 38:764–771.

Heller et al., "Complementary DNA cloning of a receptor for tumor necrosis factor and demonstration of a shed form of the receptor" (1990) *Proc. Natl. Acad. Sci. USA* 87:6151–6155.

Henney et al., "Localization of stromelysin gene expression in atherosclerotic plaques by in situ hybridization" (1991) *Proc. Natl. Acad. Sci. USA* 88:8154–8158.

Himmler et al., "Molecular cloning and expression of human and rat tumor necrosis factor receptor chain (p60) and its soluble derivative, tumor necrosis factor–binding protein" (1990) *DNA Cell Biol.* 9:705–715.

Hintzen et al., "Characterization of the human CD27 ligand, a novel member of the TNF gene family" (1994)*J. Immunol.* 152:1762–1773.

Hjemdahl et al., "$\vartheta$–adrenoceptors in human alveolar macrophages isolated by elutriation" (1990) *Br. J. Clin. Pharmacol.* 30:673–682.

Hofmann et al., "Altered gene expression for tumor necrosis factor–I and its receptors during drug and dietary modulation of insulin resistance" (1994) *Endocrinology* 134:264–270.

Holtmann et al., (1987) *J. Immunol.* 139:151–153.

Hotamisligil et al., "Increased adipose tissue expression of tumor necrosis factor–I in human obesity and insulin resistance" (1995) *J. Clin. Invest.* 95:2409–2415.

Howard et al., "Interleukin 10 protects mice from lethal endotoxemia" (1993) *J. Exp. Med.* 177:1205–1208.

Hu et al., "The effect of norepinephrine on endotoxin–mediated macrophage activation" (1991) *J. Neuroimmunol.* 31:35–42.

Huizinga et al., "The PI–linked receptor FcRIII is released on stimulation of neutrophils" (1988) *Nature* 333:667–669.

Jin et al., "Protection against rat endotoxic shock by p55 tumor necrosis factor (TNF) receptor immunoadhesin: Comparison with anti–TNF monoclonal antibody" (1994) *J. Infect. Dis.* 170:1323–1326.

Joyce et al., "Two inhibitors of pro–inflammatory cytokine release, interleukin–10 and interleukin–4, have contrasting effects on release of soluble p75 tumor necrosis factor receptor by cultured monocytes" (1994) *Eur. J. Immunol.* 24:2699–2705.

Kalinkovich et al., "Increased soluble tumor necrosis factor receptor expression and release by human immunodeficiency virus type 1 infection" (1995) *J. Interferon Cyto. Res.* 15:749–757.

Katsura et al., "Identification and characterization of soluble TNF receptor releasing enzyme (TRRE) from PMA–stimulated human monocytic THP–1 cells" (1996) *Proc. Amer. Cancer Res. Meeting* Apr. 20–24,37:492 (Abstract 3359).

Kawakami et al., "Human recombinant TNF suppresses lipoprotein lipase activity and stimulates lipolysis in 3T3–L1 cells" (1987) *J. Biochem.* 101:331–338.

Khire et al., "EGF stimulates the processing and export of a secreted form of EGF receptor" (1990) *Febs. Lett.* 272:69–72.

Khokha et al., "Antisense RNA–induced reduction in murine TIMP levels confers oncogenicity on Swiss 3T3 cells" (1989) *Science* 243:947–950.

Klinkert et al., "TNR–α receptor fusion protein prevents experimental auto–immuno encephalomyelitis and demyelination in Lewis rats: an overview" (1997) *J. Neuroimmun.* 72:163–168.

Kohno et al., "A second tumor necrosis factor receptor gene product can shed a naturally occurring tumor necrosis factor inhibitor" (1990) *Proc. Natl. Acad. Sci. USA* 87:8331–8335.

Kriegler et al., "A novel form of TNF/cachectin is a cell surface cytotoxic transmembrane protein: Ramifications for the complex physiology of TNF" (1988) *Cell* 53:45–53.

Lambert et al., "Natural serum TNF antagonists in end–stage renal failure and following renal transplantation" (1994) *Nephrol. Dia. Transplant.* 9:1791–1796.

Landmann et al., "Interferon–γ and interleukin–4 down–regulate soluble CD14 release in human monocytes and macrophages" (1992) *J. Leukoc. Biol.* 52:323–330.

Latza et al., "CD30 antigen in embryonal carcinoma and embryogenesis and release of the soluble molecule" (1995) *Am. J. Pathol.* 146:463–471.

Lawson et al. "Metabolic approaches to cancer cachexia" (1982) *Annu. Rev. Nutr.* 2:277–301.

Leeuwenberg et al., "Slow release of soluble TNF receptors by monocytes in vitro" (1994) *J. Immunol.* 152:4036–4043.

Lesslauer et al., "Recombinant soluble tumor necrosis factor receptor proteins protect mice from lipopolysaccharide–induced lethality" (1991) *Eur. J. Immunol.* 21:2883–2886.

Llovera et al., "Effects of tumor necrosis factor–α on muscle–protein turnover in female Wistar rats" (1993) *J. Natl. Cancer Inst.* 85:1334–1339.

Loenen et al., "The CD27 membrane receptor, a lymphocyte–specific member of the nerve growth factor receptor family, gives rise to a soluble form by protein processing that does not involve receptor endocytosis" (1992) *Eur. J. Immunol.* 22:447–455.

Loetscher et al., "Purification and partial amino acid sequence analysis of two distinct tumor necrosis factor receptors from HL60 cells" (1990) *J. Biol. Chem.* 265:20131–20138.

Loetscher et al., "Molecular cloning can expression of the human 55 kd tumor necrosis factor receptor"(1990) *Cell* 61:351–359.

López–Casillas et al., "Structure and expression of the membrane proteoglycan betaglycan, a component of the TGF–β receptor system" (1991) *Cell* 67:785–795.

Lovejoy et al., "Structure of the catalytic domain of fibroblast collagenase complexed with an inhibitor" (1994) *Science* 263:375–377.

Lowry et al., "Metal ion stabilization of the conformation of a recombinant 19–kDa catalytic fragment of human fibroblast collagenase" (1992) *Proteins* 12:42–48.

Madej et al., "Threading analysis suggests that the obese gene product may be a helical cytokine" (1995) *FEBS Lett.* 373:13–18.

Marchant et al., "Interleukin–10 controls interferon–γ and tumor necrosis factor production during experimental endotoxemia" (1994) *Eur. J. Immunol.* 24:1167–1171.

Marchant et al., "Interleukin–10 production during septicaemia" (1994) *Lancet* 343:707–708.

Massagué "TGFβ signaling: Receptors, transducers, and mad proteins" (1996) *Cell* 85:947–950.

Massagué et al., "Membrane–anchored growth factors" (1993) *Annu. Rev. Biochem.* 62:515–541.

Matrisian, "Metalloproteinases and their inhibitors in matrix remodeling" (1990) *Trends Genet.* 6:121–125.

Meakin et al., "The nerve growth factor family of receptors" (1992) *Trends Neurosci.* 15:323–331.

Michie et al., "Detection of circulating tumor necrosis factor after endotoxin administration" (1988) *New Engl. J. Med.* 318:1481–1486.

Mignatti et al. "Tumor invasion through the human amniotic membrane: Requirement for a proteinase cascade" (1986) *Cell* 47:487–498.

Miles et al., "Induction of soluble tumour necrosis factor receptors during treatment with interleukin–2" (1992) *Br. J. Cancer* 66:1195–1199.

Mohler et al., "Soluble tumor necrosis factor (TNF) receptors are effective therapeutic agents in lethal endotoxemia and function simultaneously as both TNF carriers and TNF antagonists" (1993) *J. Immunol.* 151:1548–1561.

Mohler et al., "Protection against a lethal dose of endotoxin by an inhibitor of tumour necrosis factor processing" (1994) *Nature* 370:218–220.

Möller et al., "Expression of APO–1 (CD95), a member of the NGF/TNF receptor superfamily, in normal and neoplastic colon epithelium" (1994) *Int. J. Cancer* 57:371–377.

Moore, "Interleukin–10" (1993) *Annu. Rev. Immunol.* 11:165–190.

Moreland et al., "Treatment of rheumatoid arthritis with a recombinant human tumor necrosis factor receptor (p75)–Fc fusion protein" (1997) *N. Eng. J. Med.* 337:141–147.

Mosley et al., "The murine interleukin–4 receptor: Molecular cloning and characterization of secreted and membrane bound forms" (1989) *Cell* 59:335–348.

Müllberg et al., "A metalloprotease inhibitor blocks shedding of the IL–6 receptor and the p60 TNF receptor" (1995) *J. Immunol..* 155:5198–5205.

Neurath et al., "Predominant pathogenic role of tumor necrosis factor in experimental colitis in mice" (1997) *Eur. J. Immun.* 27:1743–1750.

Nicholls, "The thermogenic mechanism of brown adipose tissue" (1983) *Biosci. Rep.* 3:431–441.

Nophar et al., "Soluble forms of tumor necrosis factor receptors (TNF–Rs). The cDNA for the type 1 TNF–R, cloned using amino acid sequence data of its soluble form, encodes both the cell surface and a soluble form of the receptor" (1990) *EMBO J.* 9:3269–3278.

Novick et al., "Soluble cytokine receptors are present in normal human urine" (1989) *J. Exp. Med.* 170:1409–1414.

Ogiwara et al., "Diminished visceral adipose tissue in cancer cachexia" (1994) *J. Surg. Oncol.* 57:129–133.

Old, "Another chapter in the long history of endotoxin" (1987) *Nature* 330:602–603.

Oliff et al., "Tumors secreting human TNF/cachectin induce cachexia in mice" (1987) *Cell* 50:555–563.

Olsson et al., "Isolation and characterization of a tumor necrosis factor binding protein from urine" (1989) *Eur. J. Haematol.* 42:270–275.

Olsson et al., "The receptors for regulatory molecules of hematopoiesis" (1992) *Eur. J. Haematol.* 48:1–9.

Olsson et al., "Tumour necrosis factor (TNF) binding proteins (soluble TNF receptor forms) with possible roles in inflammation and malignancy" (1993) *Eur. Cytokine Netw.* 4:169–180.

Oudart et al., "Stimulation of brown adipose tissue activity in tumor–bearing rats" (1995) *Can. J. Physiol. Pharmacol.* 73:1625–1631.

Pandiella et al., "Cleavage of the membrane precursor for transforming growth factor α is a regulated process" (1991) *Proc. Natl. Acad. SCi. USA* 88:1726–1730.

Peetre et al., "A tumor necrosis factor binding protein is present in human biological fluids" (1988) *Eur. J. Haematol.* 41:414–419.

Phillips et al., "Leptin receptor missense mutation in the fatty Zucker rat" (1996) *Nature Genet.* 13:18–19.

Plata–Salamán et al., "Chemokines/intercrines and central regulation of feeding" (1994) *Am. J. Physiol.* 266:R1711–R1715.

Porat et al., "Glycosylated recombinant human tumor necrosis factor binding protein–1 reduces mortality, shock, and production of tumor necrosis factor in rabbit *Escherichia coli* sepsis" (1995) *Crit. Care Med.* 23:1080–1089.

Porteu, "Tumor necrosis factor induces a selective shedding of its p75 receptor from human neutrophils" (1994) *J. Biol. Chem.* 269:2834–2840.

Porteu et al., "Shedding of tumor necrosis factor receptors by activated human neutrophils" (1990) *J. Exp. Med.* 172:599–607.

Price et al., "Regulation of lipoprotein lipase synthesis by recombinant tumor necrosis factor—the primary regulatory role of the hormone in 3T3–L1 adipocytes" (1986) *Arch. Biochem. Biophys.* 251:738–746.

Raines et al., "Identification and molecular cloning of a soluble human granulocyte–macrophage colony–stimulating factor receptor" (1991) *Proc. Natl. Acad. Sci. USA* 88:8203–8207.

Renauld et al., "Expression cloning of the murine and human interleukin 9 receptor cDNAs" (1992) *Proc. Natl. Acad. Sci. USA* 89:5690–5694.

Rose–John et al., "Soluble receptors for cytokines and growth factors: generation and biological function" (1994) *Biochem. J.* 300:281–290.

Rothwell, "Cytokines and thermogenesis" (1993) *Int. J. Obesity* 17:S98–S101.

Saghizadeh et al., "The expression of TNFα by human muscle: Relationship to insulin resistance" (1996) *J. Clin. Invest.* 97:1111–1116.

Satal et al., "Hemostatic parameters in sepsis patients treated with anti–TNFα–monoclonal antibodies" (1996) *Shock* 6:233–237.

Schall et al., "Molecular cloning and expression of a receptor for human tumor necrosis factor" (1990) *Cell* 61:361–370.

Schwartz et al., "Hypothalamic response to starvation: implications for the study of wasting disorders" (1995) *Am. J. Physiol.* 269:R949–R957.

Scuderi et al., "Raised serum levels of tumour necrosis factor in parasitic infections" (1986) *Lancet* Dec. 13:1364–1365.

Seckinger et al., "A human inhibitor of tumor necrosis factor α" (1988) *J. Exp. Med.* 167:1511–1516.

Seckinger et al., "Purification and biologic characterization of a specific tumor necrosis factor α inhibitor" (1989) *J. Biol. Chem.* 264:11966–11973.

Seitz et al., "In vitro modulation of cytokine, cytokine inhibitor, and prostaglandin E release from blood mononuclear cells and synovial fibroblasts by antirheumatic drugs" (1997) *J. Rheumatology* 24:1471–1476.

Semb et al., "Multiple effects of tumor necrosis factor on lipoprotein lipase in vivo" (1987) *J. Biol. Chem.* 262:8390–8394.

Senior et al., "Elastin degradation by human alveolar macrophages" (1989) *Am. Rev. Respir. Dis.* 139:1251–1256.

Seth et al., "Circulating ICAM–1 isoforms: diagnostic prostpects for inflammatory and immune disorders" (1991) *Lancet* 338:83–84.

Severn, et al. "Regulation of tumor necrosis factor production by adrenaline and β–adrenergic agonists" (1992) *J. Immunol.* 148:3441–3445.

Shalaby et al., "Binding and regulation of cellular functions by monoclonal antibodies against human tumor necrosis factor receptors" (1990) *J. Exp. Med.* 172:1517–1520.

Shohami et al., "Cytokine production in the brain following closed head injury: dexanabinol (HU–211) is a novel TNF–α inhibitor and an effective neuroprotectant" (1997) *J. Neuroimmun.* 72:169–177.

Simon et al., "Divergent T–cell cytokine patterns in inflammatory arthritis" (1994) *Proc. Natl. Acad. Sci. USA* 91:8562–8566.

Smith et al., "A receptor for tumor necrosis factor defines an unusual family of cellular and viral proteins" (1990) *Science* 248:1019–1023.

Smith et al., "CD30 antigen, a marker for Hodgkin's lymphoma, is a receptor whose ligand defines an emerging family of cytokines with homology to TNF" (1993) *Cell* 73:1349–1360.

Speiser et al., "TNF receptor p55 controls early acute graft–versus–host disease" (1997) *J. Immun.* 158:5185–5190.

Spengler et al., "Endogenous norepinephrine regulates tumor necrosis factor–α production from macrophages in vitro" (1994) *J. Immunol.* 152:3024–3031.

Spiegelman et al., "Through thick and thin: Wasting, obesity, and TNFα" (1993) *Cell* 73:625–627.

Stack et al., "Randomised controlled trial of CDP571 antibody to tumour necrosis factor–α in Crohn's disease" (1997) *Lancet* 349:521–524.

Stein et al., "Proteolytic processing of a plasma membrane–bound precursor to human macrophage colony–stimulating factor (CSF–1) is accelerated by phorbol ester" (1991) *Oncogene* 6:601–605.

Takaki et al., "Molecular cloning and expression of the murine interleukin–5 receptor" (1990) *EMBO J.* 9:4367–4374.

Talmadge et al., "Molecular pharmacology of the beta–adrenergic receptor on THP–1 cells" (1993) *Int. J. Immunopharmacol.* 15:219–228.

Tartaglia et al., "Two TNF receptors" (1992) *Immunol. Today* 13:151–153.

Tartaglia et al., "The two different receptors for tumor necrosis factor mediate distinct cellular responses" (1991) *Proc. Natl. Acad. Sci. USA* 88:9292–9296.

Tiesman et al., "Identification of a soluble receptor for platelet–derived growth factor in cell–conditioned medium and human plasma" (1993) *J. Biol. Chem.* 268:9621–9628.

Tracey et al., "Anti–cachectin/TNF monoclonal antibodies prevent septic shock during lethal bacteraemia" (1987) *Nature* 330:662–664.

Tracey et al., "Cachectin/tumor necrosis factor induces lethal shock and stress hormone response in the dog" (1987) *Surg. Gynecol. Obstet.* 164:415–422.

van der Poll, et al., "Endogenous IL–10 protects mice from death during septic peritonitis" (1995) *J. Immunol.* 155:5397–5401.

van der Poll et al., "Tumor necrosis factor in sepsis: Mediator of multiple organ failure or essential part of host defense?" (1995) *Shock* 3:1–12.

van Deuren, "Kinetics of tumour necrosis factor–alpha, soluble tumour necrosis factor receptors, interleukin 1–beta and its receptor antagonist during serious infections" (1994) *Eur. J. Clin. Microbiol. Infect. Dis.* 13 (Suppl. 1):S12–S16.

van Deventer et al., "Monoclonal antibody therapy of inflammatory bowel disease" (1997) *Pharm. World Sci.* 19:55–59.

Van Hogezand et al., "New therapies for inflammatory bowel disease: an update on chimeric anti–TNFα antibodies and IL–10 therapy" (1997) *Scand. J. Gastro.* 223:105–107.

Van Zee et al., "Tumor necrosis factor soluble receptors circulate durng experimental and clinical inmflammation and can protect against excessive tumor necrosis factor α in vitro and in vivo"(1992) *Proc. Natl. Acad. Sci. USA* 89:4845–4849.

Waage et al., "Detection of tumour necrosis factor–like cytotoxicity in serum from patients with septicaemia but not from untreated cancer patients" (1986) *Scand. J. Immunol.* 24:739–743.

Woessner, Jr., "Matrix metalloproteinases and their inhibitors in connective tissue remodeling" (1991) *FASEB J.* 5:2145–2154.

Yamamoto et al., "FR167653, a dual inhibitor of interleukin–1 and tumor necrosis factor–α, ameliorates endotoxin–induced shock" (1997) *Eur. J. Pharmacol.* 327:169–175.

Yui et al., "Cytotoxicity of tumour necrosis factor–alpha and gamma–interferon against primary human placental trophoblasts" (1994) *Placenta* 15:819–835.

Zamir et al., "Evidence that tumor necrosis factor participates in the regulation of muscle proteolysis during sepsis" (1992) *Arch. Surg.* 127:170–174.

Zhang et al., "Positional cloning of the mouse obese gene and its human homologue" (1994) *Nature* 372:425–432.

Zupan et al., "Identification, purification, and characterization of truncated forms of the human nerve growth factor receptor" (1989) *J. Biol. Chem.* 264:11714–11720.

(2000) "Enbrel(R) (etanercept) U.S. and European Long–Term Clinical Trial Data Presented at the Annual Meeting of the European League Against Rheumatism." *Company News On–Call* http://www.prnewswire.com/cgi–bin/stories.pl?ACCT=105&STORY=/www/story/06–23–2000/0001250565 (Jun. 23, 2000).

(2000) "Immunex Reports Second Quarter 2000 Results." *Immunex Investor Relations* http://www.immunex.com/investor/pressreleases/pr000719.html (Jul. 19, 2000).

Lesslauer, et al., "Recombinant soluble tumor necrosis factor receptor proteins protect mice form lipopolysaccharide–induced lethality," *Eur. J. of Immunol.* (1991) vol. 21:2883–2886.

Monler, et al., "Soluble tumor necrosis factor (TNF) receptors are effective therapeutic agents in lethal endotoxemia and function simultaneously as both TNF carriers and TNF Antagonists," *J. of Immunol.* (Aug. 1, 1993) vol. 151(3):1548–1561.

Trehu, et al., "Phase I trail of interleukin 2 in combination with the soluble tumor necrosis factor receptor p75 IgG chimera," (Aug. 1996) vol. 2:1341–1351.

Gonzalez et al., "Variation among human 28S ribosomal RNA genes," *Proc. Natl. Acad. Sci. USA* 82:7666–7670 (1985).

Katsura et al., "Identification of the proteolytic enzyme which cleaves human p75 TNG receptor in vitro," *Biochemical and Biophysical Research Communications* 222:298–302 (1996).

Minet and Lacroute, "Cloning and sequencing of a human cDNA coding for a multifunctional polypeptide of the purine pathway by complementation of the ade2–101 mutant in *Saccharomyces cerevisiae*," *Curr. Genet.* 18:287–291 (1990).

Oshima et al., "The human cation–independent mannose 6–phosphate receptor. Cloning and sequence of the full–length cDNA and expression of functional receptor in cos cells," *The Journal of Biological Chemistry* 5:2553–2562 (1988).

Porteu et al., "Human neutrophil elastase releases a ligand–binding fragment from the 75–kDa tumor necrosis factor (TNF) receptor," *The Journal of Biological Chemistry* 266:18846–18853 (1991).

\* cited by examiner

SEQUENCE LISTING (1) GENERAL INFORMATION:

(iii) NUMBER OF SEQUENCES: 154

(2) INFORMATION FOR SEQ ID NO:1:

(i) SEQUENCE CHARACTERISTICS:
        (A) LENGTH: 4047 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:1:

```
AAGCTTTTTG CTTTCCTTCC CCGGGAAAGG CCGGGGCCAG AGACCCGCAC TCGGACCAGG      60

CGGGGGCTGC GGGGCCAGAG TGGGCTGGGG AGGGCTGGGA GGGCGTCTGG GGCCGGCTCC     120

TCCAGGCTGG GGGCCGCCAG CTCCGGGAAG GCAGTCCTGG CCTGCGGATG GGGCCGCGCG     180

TGGGGCCCGG CGGGGCGGCC TCGGGAGGCG TCCAGGCTGC GGGAGCGGGA GGAGCGGCCG     240

TGCGGGCGCC AGCGCCGTGG GTGGAGGTCG CCGTCCCTCC TGAGGGGCAG CCAGTGCGTT     300

TGGGACCCGG GAGCAGAGCC CGCGCCTCCC CAGCGGCCTC CCCGGGGGTC TCACCGGGTC     360

ACCCGAGAGC GGAGGCCCCG GCTCCGCAGA AACCCGGGGC GGCCGCGGGG AAGCAGCGCC     420

CTCAGGCGTC GGAGGAGCCC CCAGAAGGAC CTCGCGCCTT CCCGCCGGGC TCCGACCGCC     480

TGGGTTCGGT GCGGGACGGC CCAGGCCGCC AGGACCCCCA AGCGCAGCTC AGTCTGCGGG     540

GCACGACCCA GAGGCCAGCA GCAGAGGACG GGGCCGGGGC CGGGAGAGGG CGGGGAGGGC     600

GCTCCTGGGA GGTCAAGGCC AGGGCTAGAC TTTCAGGGTC ATGGCCTGGC CCCTCATCCC     660

CAGGGAGGTG AGGGGGCTCT GTGAGCAGAG GGGGCCCCGG TGGAGAAGGC GCTGCTAGCC     720

AGGGGCGGGG CAGGAGCCCA GGTGGGGACT TAAGGGTGGC TGAAGGGACC CTCAGGCTGC     780

AGGGATAGGG AGGGAAGCTA GGGGTGTGGC TTGGGGAGGT GCTGGGGGAC CGCGGGCGCC     840

CTTTATTCTG AAGCCGAATG TGCTGCCGGA GTCCCCAGTG ACCTAGAAAT CCATTTCAAG     900

ATTTTCAGGA GTTTCAGGTG GAGACAAAGG CCAGGCCCAG GTGAAAATGT GGCAGTGACA     960

GAGTATGGGG TGAGAACCAC GGAGAGAGGA AGTCCCCGAG GCGGATGATG GGACAGAGAG    1020

CGGGGACCAG AATTTTTTAA AACGCATCTG AGATGCGTTT GGCAGACTCA TAGTTGTTTT    1080

CCTTTCACGG AGAAAGTGTG GGCAGAAGCC AGCTCTAAAG CCCAGGCTGC CCAGCCTGCA    1140

CTGGCAGAGC TGACGGAAGG CCAGGGCAGA GCCTTCCCTC CCTGTCACAG ACATGAGCCC    1200

TGGAGATCTG GAATGAGGCA GATGTGCCCA GGGAAAGCTG ATCCGCCCCG ACCCAGGGCC    1260

CCCCGGGTGC CCCTTTGAGC GTGGAATCGT TGCCAGGTCA TGGCTCCCTG CTATCGAACA    1320

CCGGACACGG GTCGTGTGCT GCACCTGGCA GTTGCAGGAC CGACACCCAC AATGCCTTAA    1380

GAGGTGATGA CTGCCTTCCA GGGGCCTGGC TGGCTGACAC TTTGCATGGC TCCTGGAGAA    1440
```

```
GAGGGATTGA GTGGAGTCCA CGGGTCATGG CCACGTCCTG GGTGCTGCCT CTGAGGCAGG    1500

GCCCGGCTGG GGTGAGAAGG GGCTGGAGAC AGGTTCCTGC CAGTTCAGCC TCTAACCGGT    1560

GGTCTTCATG CCTAGGAACC CACTGGGGGC TTATGAAACT GCAGGTGGCT GAGTCCTTGC    1620

CATGGGGTCT CTCCTTCAGG AGGTCTGGGT GGGGCCGGAG ACTGTACCCC ACAAAGGGTC    1680

CCAGGTGAGG CGGATGTGGC CTGGCGCTGT GTGGCTCTGG ACCTAGTCCT TGGGCTTGGG    1740

CTGGCGCCCA GGGCCTGGGC TTGAGACAGC TGTGACGCAG GCAAGCCATT TACCCCGTTT    1800

GTGGGACAT  TACATCTTCC TAGCTTGGAA CACACAGGCA GCCAGGGTTG TTATCCACAT    1860

TCCTCCTCCA TGTTCTTCTC TTGAGAACTT TTACCAGGTA TGTCAGGAGC TGGGCTCCAC    1920

CAGGGAGACT CAAGTGGAAA GCCCTCATCC TTGTCCTCCA GGAGACAGGA AAACCTATGG    1980

TTACAATTCC AGGGACAAGA GCGATGCATG TGAGGTGTGG CAAATCTCAC TGTTCAACTG    2040

GAGAAATCAG AGACAGCTTC CTGGAGGCAG TGACACCTGG ACAGGCTTCT CCACAGGAGG    2100

AAGCGAGTGA GAGAAGCCAA CTGGGATGGA CCCATCATGT AGGGGGAACA GTGCGCGCAG    2160

AACCAACAAC CACCCCCACC CTAGGCCCAG AGCTCACGGA GAGAGCTGGG CCTCTCGGGG    2220

TGACTACATA GTTCCCTGCT GGATCTTAGG TCTTGTCCTT GGGCAGCTCT GCTGAGACCT    2280

CTATGCCTGT TCCAGGCTGC ACCAAGGTTT TGTGACTATT GGTCTGGGGT TGTTTTGCAG    2340

CAACTGAAGT GTTCTGTTGT AAAACAGGCA CTTGATTTGC TGGAAGGAAT GCTGTTTGTT    2400

CTTGCTGCGA CAAACATTGA GCAGCATTTA GTGGGCGGTT TATATCTTGT GGAGTAATGG    2460

GTGTTTTTGA AGTCTGTCCT GGGTACTGCA CATTAAAAGG AATATCATTT TCTGAAACAT    2520

TGCTATTTTC CACACCAGAA ATCATATCCT CTTGCTGGTC CATGTCTGAA GACCTTACAC    2580

GAGAAAGTCT TAATGTAAGT TTAGTAGAGT CCTTGGATGG AGAACTAATT ATATCATACA    2640

TTGCCGCTTT CTCACTCTGC TCTTTTTCAT CCTTGCCTAA TTTCATTTTC TTCTGCTTCT    2700

TTTGTTTTCT TTCTGGAGAA TCTAGCAAGA TATCTGGTGG AACATCTCGA GGTGATGAAC    2760

AAGGTAGAGA CTGAGATTGT AGGATTAAAG GTGGTCTTGA GCCTTTAGGA GTTCCTTCAC    2820

TTCCAGCAGG GGAGCATACT GGCTGTGGAG ATCTCAAGGG AAAAGATGCA GCATTCCTCA    2880

TTGTTGAAGA ATCTCCATCG TCACTACTTA GCCTGTGCAC CATGTGTAGG TAGTCCTCAC    2940

TTGAACCATG TCTAGGATTA TCAGCATGAT GATTAGCTGA ATTGCCAGAC AACGGACCAG    3000

AAACTTTATT ATCATGTATG TTTCTCAAAC CACCTGCAAC AATGGGACTT GATACCGATG    3060

CTTGTTGCAT CTGTGGATGT GTTGTGTAAC TTGAAGGATG GGAATATGGC ATGTATCCTG    3120

CAGGGCTTTG TGGGCGTAT  GGACTAGGCA CTGGGCTATT TTGCTGTGGC ATAAATCTGT    3180

TCCCAGAGCT TGTCTGTGGT GGCACAAACC GGCTGGAGGG CTATGTGAG  ATAGTGGTTT    3240

GTTGATAATT GGAAGATGCA GGACTACTGT GCATGGAATT CTGAGAAAGT TTATACTGAG    3300

ACATCATCAT TCCACTTTGT ACATATCTGT TCTGCATGCT TTTCTCCCTG AAAACATTAG    3360

GACTCCTTGC CAGGACGGCC TGCAACAAGA CTGGTATGTC ACCTTCTGGG TCATCACTGC    3420

CAAGGTTATC TTTCAACTCT ATGTGATCTG TTGATACCTG GTTGAGGCTA TGGACAAGCT    3480

GTGAAACCAA ATTGTCATCC CTACAAGCCA AAAGGCAGTT CACCTCTTCT GCTATTCGTG    3540

CATTAAAGAG AAGGCTCTTT GTAGTTGTAG CAGGTAAAGG AGATGGAAGA GGCAGCTGGT    3600

TCAGGAGGTC TGTGAGACTA GCAATCCCCG CAAGAGTAGT AATGGGACA  TGGGCATAT    3660

CCCCATTCAT CCTGAATTTC TGGAATGGTG TTGCCTATAA AGTACTTAG  TTCAGGTGCC    3720

AGCTGTCATT ACTTCCCATT TCCCAAACAC TGGGCGAATC GGCGTCTGAA TCCAAGGGGA    3780
```

-continued

```
GGCCGAGGCC GCTGTGGCGA GAGACTATAA TCCGGGCCGG GAGGGGGGGC GGCTACGGCT    3840

CCTCTTCCGT CTCCTCAGTG CGGGGAACAT GTAGAGCCGG GGGGAGACCA GCCGAGAAGA    3900

CAAATCGTTG CTTCTTCTTC CTCCTCCTCC TCCTTCTCCC ACATAGAAAC ACTCACAAAC    3960

ACCCGACCAC GGGCCCGAGC TACCGGGGGG GCATCGCCGC GGGCCCGGGA ACCAATTCTC    4020

CTGTCGGCGG GGGCGTCCTT TGGATCC                                       4047
```

(2) INFORMATION FOR SEQ ID NO:2:

(i) SEQUENCE CHARACTERISTICS:
        (A) LENGTH: 739 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:2:

```
GGATCCAAAG GTCAAACTCC CCACCTGGCA CTGTCCCCGG AGCGGGTCGC GCCCGGCCGG      60

CGCGCGGCCG GGCGCTTGGC GCCAGAAGCG AGAGCCCCTC GGGGCTCGCC CCCCCGCCTC     120

ACCGGGTCAG TGAAAAAACG ATCAGAGTAG TGGTATTTCA CCGGCGGCCC GCAGGGCCGG     180

CGGACCCCGC CCCGGGCCCC TCGCGGGGAC ACCGGGGGGG CGCCGGGGGC CTCCCACTTA     240

TTCTACACCT CTCATGTCTC TTCACCGTGC CAGACTAGAG TCAAGCTCAA CAGGGTCTTC     300

TTTCCCCGCT GATTCCGCCA AGCCCGTTCC CTTGGCTGTG GTTTCGCTGG ATAGTAGGTA     360

GGGACAGTGG GAATCTCGTT CATCCATTCA TGCGCGTCAC TAATTAGATG ACGAGGCATT     420

TGGCTACCTT AAGAGAGTCA TAGTTACTCC CGCCGTTTAC CCGCGCTTCA TTGAATTTCT     480

TCACTTTGAC ATTCAGAGCA CTGGGCAGAA ATCACATCGC GTCAACACCC GCCGCGGGCC     540

TTCGCGATGC TTTGTTTTAA TTAAACAGTC GGATTCCCCT GGTCCGCACC AGTTCTAAGT     600

CGGCTGCTAG GCGCCGGCCG AAGCGAGGCG CCGCGCGGAA CCGCGGCCCC CGGGGCGGAC     660

CCGCGGGGGG GACCGGGCCG CGGCCCCTCC GCCGCCTGCC GCCGCCGCCG CCGCCGCGCG     720

CCGAAGAAGA AGGGGGAAA                                                 739
```

(2) INFORMATION FOR SEQ ID NO:3:

(i) SEQUENCE CHARACTERISTICS:
        (A) LENGTH: 233 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:3:

```
CAAGAGTGGC GGCCGCAGCA GGCCCCCCGG GTGCCCGGGC CCCCCTCGAG GGGGACAGTG      60

CCCCCGCCGC GGGGGCCCCG CGGCGGCCG CCGCCGGCCC CTGCCGCCCC GACCCTTCTC     120

CCCCCGCCGC CGCCCCCACG CGGCGCTCCC CCGGGGAGGG GGGAGGACGG GGAGCGGGGG     180

AGAGAGAGAG AGAGAGAGGG CGCGGGGTGG CTCGTGCCGA ATTCAAAAAG CTT           233
```

(2) INFORMATION FOR SEQ ID NO:4:

(i) SEQUENCE CHARACTERISTICS:
        (A) LENGTH: 2998 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:4:

```
GGATCCAAAG AATTCGGCAC GAGGTAGTCA CGGCTCTTGT CATTGTTGTA CTTGACGTTG    60
AGGCTGGTGA GCTTGGAAAA GTCGATGCGC AGCGTGCAGC AGGCGTTGTA GATGTTCTGC   120
CCGTCCAGCG ACAGCTTGGC GTGCTGGGCG CTCACGGGGT CCGCATACTG CAGCAGGGCC   180
TGGAACTGGT TGTTCTTGGT GAAGGTGATG ATCTTCAACA CTGTGCCGAA CTTGGAGAAA   240
ATCTGGTGCA GCACATCCAG GGTCACAGGG TAGAAGAGGT TCTCCACGAT GATCCTGAGC   300
ACGGGGCTCT GCCCGGCCAT CGCCATCCCT GCATCCACGG CCGCCGCCGA GGCAGCCAAG   360
GCCAGGTTCC CCGACTGGAC CGAGTTCACC GCCTGCAGGG CCGCCTGGGC CCGCGCCTGG   420
TTGGGAGAGC TGTCGGTCTT CAGCTCCTTG TGGTTGGAGA ACTGGATGTA GATGGGCTGG   480
CCGCGCAGCA CAGGGGTCAC CGAGGTGTAG TAGTTCACCA TGGTATTGGC AGCCTCCTCC   540
GTGTTCATCT CGATGAAGGC CTGGTTTTTC CCCTTCAGCA TCAGGAGGTT GGTGACCTTC   600
CCAAAGGGCA GCCCCAGGGA GATGACTTCC CCCTCCGTGA CGTCGATGGG GAGCTTCCGG   660
ATGTGGATCA CTCTAGAGGG GACGCCTGCA CTTCGGCTGT CACCTTTGAA CTTCTTGCTG   720
TCATTTCCGT TTGCTGCAGA AGCCGAGTTG CTGCTCATGA TAAACGGTCC GTTAGTGACA   780
CAAGTAGAGA AAAGCTCGTC AGATCCCCGC TTTGTACCAA CGGCTATATC TGGGACAATG   840
CCGTCCATGG CACACAGAGC AGACCCGCGG GGGACGGAGT GGAGGCGCCG GAATCCTGGA   900
GCTAGAGCTG CAGATTGAGT TGCTGCGTGA GACGAAGCGC AAGTATGAGA GTGTCCTGCA   960
GCTGGGCCGG GCACTGACAG CCCACCTCTA CAGCCTGCTG CAGACCCAGC ATGCACTGGG  1020
TGATGCCTTT GCTGACCTCA GCCAGAAGTC CCCAGAGCTT CAGGAGGAAT TTGGCTACAA  1080
TGCAGAGACA CAGAAACTAC TATGCAAGAA TGGGGAAACG CTGCTAGGAG CCGTGAACTT  1140
CTTTGTCTCT AGCATCAACA CATTGGTCAC CAAGACCATG GAAGACACGC TCATGACTGT  1200
GAAACAGTAT GAGGCTGCCA GGCTGGAATA TGATGCCTAC CGAACAGACT TAGAGGAGCT  1260
GAGTCTAGGC CCCCGGGATG CAGGGACACG TGGTCGACTT GAGAGTGCCC AGGCCACTTT  1320
CCAGGCCCAT CGGGACAAGT ATGAGAAGCT GCGGGGAGAT GTGGCCATCA AGCTCAAGTT  1380
CCTGGAAGAA AACAAGATCA AGGTGATGCA CAAGCAGCTG CTGCTCTTCC ACAATGCTGT  1440
GTCCGCCTAC TTTGCTGGGA ACCAGAAACA GCTGGAGCAG ACCCTGCAGC AGTTCAACAT  1500
CAAGCTGCGG CCTCCAGGAG CTGAGAAACC CTCCTGGCTA GAGGAGCAGT GAGCTGCTCC  1560
CAGCCCAACT TGGCTATCAA GAAAGACATT GGGAAGGGCA GCCCCAGGGT GTGGGAGATT  1620
GGACATGGTA CATCCTTTGT CACTTGCCCT CTGGCTTGGG CTCCTTTTTC TGGCTGGGGC  1680
CTGACACCAG TTTTGCCCAC ATTGCTATGG TGGGAAGAGG GCCTGGAGGC CCAGAAGTTG  1740
CTGCCCTGTC TATCTTCCTG GCCACAGGGT TCATTCCCA  GATCTTTTCC TTCCACTTCA  1800
CAGCCAACGG CTATGACAAA ACCACTCCCT GGCCAATGGC ATCACTCTTC AGGCTGGGGT  1860
GTGCTCCCTG ACCAATGACA GAGCCTGAAA ATGCCCTGTC AGCCAATGGC AGCTCTTCTC  1920
GGACTCCCCT GGGCCAATGA TGTTGCGTCT AATACCCTTT GTCTCTCCTC TATGCGTGCC  1980
CATTGCAGAG AAGGGGACTG GGACCAAAGG GGTGGGGATA ATGGGGAGCC CCATTGCTGG  2040
CCTTGCATCT GAATAGGCCT ACCCTCACCA TTTATTCACT AATACATTTT ATTTGTGTTC  2100
TCTAATTTAA AATTACCTTT TCATCTTGCT TGATTTTCCT TCAGCTAAAT TAGAAATTTG  2160
TAGTTTTTCC CCTAAAAAAT TCAATGGCAT TCTTTCTTAT AAATTACATT CTCTGATTTT  2220
CTTGTCAGCC TGCTTCAAGG AAATCCATGT GTTCAAAATG CTTGCTCGCA GTTTGCTCCA  2280
```

```
TACCAAATGG TTGCTTAACC CAAATATCTG AGCAGCAAAT TGAGCTGATC CTTCTGGAGA   2340

AAGTACGGTT GAACAGCCAA GACCACTGGG TAGTCGAAGA GAAGACCACA CATCCTGAAC   2400

TCCCCAGTCT GGTGTGAGGG GAGGACAGCT GATAACTGGA TATGCAGTGT TCCCAGACAT   2460

CACTGGTCCC AAACCATTAC TTCTGCCTGC CACTGCCACA AATACAGTAG GAATGCCATC   2520

CCCTTCATAC TCAGCTTTAA TCCTCAGAGT TTCATCTGGT CCTTTATGCG CAGATGTTAC   2580

TCGAAGTTCA CATGGAATGC CAAAATTTCC ACAGGCCTTC TTGATTTTTT CACAGTGACC   2640

AAGATCAGAA GTAGAGCCCA TCAACACTAC AACCCTGCAC TGACTTTCTG ATTTCAAAAG   2700

CAACTCTACT CTCTCTGCAA CCCACTCAAA GTTTTTCTTT ACCATTTGGA GCCCTTCAGG   2760

AGTTACTTCT TTGAGGTCCC GATAAGACTG TTTGTCTTTC TGTTGGCTTC GATCTCCTGA   2820

TGGCCAGAGT CTCCAGGAAT CATTGTCAAT AACATCAGCA AGAACAATTT CTTTGGTGGT   2880

TACATCAACA CCAAATTCAA TCTTCATATC AACCAGTGTA CAATTCTGGG GCAACCAGGA   2940

TTTCTCCAGT ATTTCAAATA TAGCCTGTGT AGCATCTCGT GCCGAATTCA AAAAGCTT    2998
```

(2) INFORMATION FOR SEQ ID NO:5:

(i) SEQUENCE CHARACTERISTICS:
        (A) LENGTH: 4152 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:5:

```
AAGCTTTTTG TGAAAACCCT AGGATATGTC CCCTCCCTCA CCACACCCAA CCCCCCGCCC     60

CTGCCCCAGG ACATGACGAT GCCTCACACA CACACACACA CACACATACA CACAAGGCCG    120

TGAGCTGCAC GCAGGAACAT GGGCTGCACT CACGACAACA TTGAAAAAAT ATACATTATA    180

TATGTACACC CGGGGCCCCC ACGTCCCCTC CCGTCCCCGC AGCCTGGCCA CACCAGGTCA    240

CGGAGGAGGG GCCGGGGCTG CAGGACCTCA GGACTGCAAG GCAGGAAGG GAAACAGGAC     300

AAGAAAGGAA GGAAGTTGGA AAGGAGGGAG AAATGGGGTC CCCAGACTGA AATGGAAATG    360

AGGTGGGGCG ATCATAAGAG AAGCAGGGAC GATGGTCCAG CTGAGGGAGC CCTGCAGAGG    420

GGGAAAAGCT TCCCATGGAC AGGAGAGAGA AGGGAAGGGG AGAGGAGAGG GTTTCCTTCA    480

ATCCCACCCC CAGCCCCAGC CCCAGCCCCA GCCATTGCAA TCGTCACCCT CTCCCCAACA    540

CAGTGAGTGC TAAGGGGGCA GCTGCCATTG GGGGTAGAAA GGCAGCTGAA GTCCAGCCCA    600

CTTTCCAACC CAGCCAGCCC CAGTGCAAGG GCACACCAG GAGCATGACA GCCCAGAAGT     660

GAGGGATGGG GGGCCGGGGG AGGGCAGGG CGGACTCCAG AGGGCCCGCT GGGGTTTTGA     720

AATGAAAGGA GGACTGGTTC TGAAGCCTCT CTCCCTCTTG GTCTCTGTGT TCCCAGAAAG    780

TCCTTCTCCC ATGTCTGGAG TGTCTGTTTC ACCAGGGCAG AATTCCCCCT CTGCGTGGGG    840

AGAGGTGTAG GCCTTAGTAG CGGTGTGGGG GGGTCTCGAT GATGCGTCTC TCGTCGCTGC    900

TGGGGGAATC GGCCACCTCC GAGTCACTGC TGTCCTCATC CTCCTGCTGG CCCCCAACAG    960

CCCCCGTCAC ACAGGACTGC CGATTCTGGT AGGACTCCAT GGGGTTCACA ATGATGGTGA   1020

GAGCTGAGTC ATCCCAGAAG AGGTCTGGGT CCTTGGGGTC ACTGGAGGCC CCTGGAGGCC   1080

CGCCGGCCCC TGAGACGCGG CGGTGAAGGG AATGGATGCG CACCAGGCCC AGGACGACCA   1140

TGAGCACCAG GAAGCCCACG CACACCACAA TGATGAGGGT TGCGGCGCTG GGTATCATGG   1200

AGTTTCTGTG GGAGCTGGCT AGGCTGTGTC CAGCCATCTC AGGCGGGGGC TGGTGACCAC   1260
```

```
GGTGCAGGAA CTGCTGGGAG CTGAGCACGT GGCTGGGGTG GGCAACCCGG TTCATGCTGT   1320

GCAGGACATT GACCTCCACG ATGAATTCAT TGCTGGAGTA ACGGCCATTC ATTTCCGAGC   1380

AGGAAAGCCG GAACTTCCTG GTGTAGAGGG CAGCTCCGTG TCGCAGCCGA TAACGAGCCT   1440

GCCTCAGGAT CTCTTCATAC ACAGTGATGC TCTCCACCCC AGCAATAGTG AGGTAGGCAG   1500

ATGTGTTGGT GAGCTCCAGC CCCCGCTGCT GCAGAGAGGT TGTGTCCAGG AGCAGGCTTT   1560

CCCGCTCGGG ATCCAGGTCA TCCCCCACCA GAGAAATTTC ACAGCCATCC AGGTTGTGCA   1620

CAATCTCATC CGACATGCGT GTGTCTGTCA CTGTGCCCTG CCAACTCTCA TCCTTTTTGG   1680

CCTCCACCTG GTGAGAAATG GAGCAGGTGA TTTGAAGATC AGGGAACAAA GGGACGCCGT   1740

TGGTTCCCTC AAAGTCCACA GCTGGGCGGG CAAAATGAGC AGTGCCACTC AGCAGGATCT   1800

GGGGGGCGTC AGGCTGAAGG ACGACCACGT AGCCCTCCAC TTCAGGGATG GAGACGCAGG   1860

ACTCTTCGCT GAAGCACTTG ACAGCAGTGG TGAGGCGCAG GGGCCTGACG CCGGGCGTGG   1920

CAAAGCGCAG AGTGTTCATG TAAGCCACAT GCTGCAGGGC ATGGTTGAAG GTCTCCACAT   1980

CATCCCCCTC CAGGGTGAGC AGGGACTGTG AGGGGTTCAC GTGGACCTTC ATGCCTTTGC   2040

CCAGGCTCTC GAAATCCCTA TAGTCCAGCC CCTCCCGACA TGCATAGAGG CACTCGATGA   2100

CCTCGCGGCT CTCCAGGCGA CCTGAGCGCA CGCTGAAACC AGCCAGGTAG CCATGGAAGT   2160

AGTGGTGGAT CGACAAAGGG TCTCCTTGGG TGGTGTCTGT ACTGTTGTCT CCCTTTTCCT   2220

TCTCTTTGTT CTTCTCCTCA GTCCAGCAGG CCCCAATCAT GAGAGCAGGC TCCCTTCGGG   2280

GTGGGTGGAT GAGGCCATTG TCATGGATGA GGGCAGGGTC GAAGGAGATG CCGTCGGTAT   2340

AGAGTGTGAC TGTGGGGAAC TCGAGGTTCA GAGCGTAGTG GTGCCACTCA TCATCACAGA   2400

CCTGCTCCAG CTTCCAGAGG AACTTGACTG GGCGGGCACT CTCAAGCAGG GGCCAGTAGA   2460

GGAAGGCAAT CCTACAGCCG TGGACAGTCA GCGAGTAGTG AGAGAAGCCG TCCTCATTCT   2520

GGACAGTGTT ACATACGATG GTTTCCTCTT CCTTCTTGCC CTTGTTGGGA GTTACGCCAT   2580

GCTTCATCCA GAAGGACAGG GTGAAGTGGT CACTGAGGCT GTCCTGGGGC CCAGAGCCCA   2640

GCCCACTGGG GCCACCCAGG GGCACCTGCA CAGCCTGGGT GCCATTGAAC CAGTAGATCA   2700

GGCTGCTGTC CTGGCTGTAG TGCACCGAGA GTCCTGCTGT CCAGTTGGCA TTGGGGCCAG   2760

GCATGGGCAA CAGATCCACT TCCCCAGTGG CAGCACCACA GAGTTTCCGC AGCGCCCGCT   2820

CTGAGTAGTT GTCACGGTCA CAGCCCTTGG CCACATGGCT GGTCTGCAGC TCTATGGTGG   2880

CCTGAATGTT CCAGAGTGGT TCATCACAGG TCTCCAGGCG GATACCAGGG AACAAAGCCA   2940

AGCTCCCAGC ACCTGGTGCA TATTCGATCC TTTTGTTCCA GCCTTGCCAG CTGGGTTTAC   3000

AGGTGGGCTT CACCTGAATC TCCACCTCAG CATCATCTGC TGCCCGCTTC TTCCCACAGT   3060

CATAAGCTGT CACTGTAAAC TTATAGAGCC TCTCACCACT GTACTGCAGC TTCTCTGTGT   3120

TCTCAATGTT CCCGTCATTG TCAATGAGGA AAGGGGTGTT GGGTGTGAGA ATCTCATAGT   3180

AGCAGATCTG GCTGTACTGG GGGGAGCAGT CACCGTCAAT GGCTTCCACC CGCAGGATGC   3240

GATCGTACAG CTTCCCCTCT GTCACAGCCG CACGATACAG CCGTTCCACA AACACTGGGG   3300

CAAACTCGTT CACATCGTTG ACCCGCACAT GCACAGTGGC CTTGTGGGAC TTCTTGGTGT   3360

TGGCCCCGTC GGGGCCCTCG CCACAGTCAT AGGCCTGGAT GGTGAAGGTG TGTTCCTTCT   3420

GGGCCTCGCA GTCCACAGGC TCCTTGGCCC GGATCAGCCC CTCTCCTGTC GCCTTGTCAA   3480

GGATCACAGC CTCAAAGGGC ACCCAGACC CATGGAGCCG GAAGCCGCAG ATCTCACCTG   3540

CATAGCGCAG CGGGGCATCC TTGTCCAAGG CAAAGAGTGG TGGATTCAGT AGGACCGTGT   3600
```

```
TGTCATTCTC CATGACGATG CCCTGGTACT CTGCCTCAAT CCATGGCTTG TGCTTGTTGG    3660

CTTTGTTACA GGAGCAGGAC GCGAGCAGAG AGGCCAGCAG AAGGGGCAGC AGCAGGAGGG    3720

TCATGGTGCG GCGTGGGGCA GGGCAGGGCC AGGCGTTTGC CTCCCCTGGG AGCCTCCAGC    3780

CTGCGGATTC CACCTTGCGG GAGGGATACA GGGGGGGAAA ACCAAAATAA AACGTCAAAT    3840

AAATTGTGTA GGAGGAGTCC AGCTTAGGAC CGGGCCAGAG CCAGGCCAGG CTCGGGGAGG    3900

GGGCCTCTGC AGGTTCAGAG GATCACTGCT GCCACCACCG CCACCCTGGG AGCCAGTTAT    3960

TTTGCCATGG CCTTGATTGC AACAGCTGCC TCCTCTGTCA TGGCAGACAG CACCGTGATC    4020

AGGATCTCTT CTCCACAGTC GTACTTCTGC TCAATCTCCT TGCCAAGGTC TCCCTCAGGG    4080

AGACGAAGGT CCTCTCGTAC CTCCCCGCTG TCCTGGAGCA GTGATAGGTA CCCATCCTGG    4140

ATCTTTGGAT CC                                                        4152
```

(2) INFORMATION FOR SEQ ID NO:6:

(i) SEQUENCE CHARACTERISTICS:
        (A) LENGTH: 3117 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:6:

```
GGATCCAAAG ATTCGGCACG AGTGGCCACA TCATGAACCT CCAGGCCCAG CCCAAGGCTC      60

AGAACAAGCG GAAGCGTTGC CTCTTTGGGG GCCAGGAACC AGCTCCCAAG GAGCAGCCCC     120

CTCCCCTGCA GCCCCCCCAG CAGTCCATCA GAGTGAAGGA GGAGCAGTAC CTCGGGCACG     180

AGGGTCCAGG AGGGGCAGTC TCCACCTCTC AGCCTGTGGA ACTGCCCCCT CCTAGCAGCC     240

TGGCCCTGCT GAACTCTGTG GTGTATGGGC CTGAGCGGAC CTCAGCAGCC ATGCTGTCCC     300

AGCAGGTGGC CTCAGTAAAG TGGCCCAACT CTGTGATGGC TCCAGGGCGG GGCCCGGAGC     360

GTGGAGGAGG TGGGGGTGTC AGTGACAGCA GCTGGCAGCA GCAGCCAGGC CAGCCTCCAC     420

CCCATTCAAC ATGGAACTGC CACAGTCTGT CCCTCTACAG TGCAACCAAG GGGAGCCCGC     480

ATCCTGGAGT GGGAGTCCCG ACTTACTATA ACCACCCTGA GGCACTGAAG CGGGAGAAAG     540

CGGGGGGCCC ACAGCTGGAC CGCTATGTGC GACCAATGAT GCCACAGAAG GTGCAGCTGG     600

AGGTAGGGCG GCCCCAGGCA CCCCTGAATT CTTTCCACGC AGCCAAGAAA CCCCCAAACC     660

AGTCACTGCC CCTGCAACCC TTCCAGCTGG CATTCGGCCA CCAGGTGAAC CGGCAGGTCT     720

TCCGGCAGGG CCCACCGCCC CCAAACCCGG TGGCTGCCTT CCCTCCACAG AAGCAGCAGC     780

AGCAGCAGCA ACCACAGCAG CAGCAGCAGC AGCAGCAGGC AGCCCTACCC CAGATGCCGC     840

TCTTTGAGAA CTTCTATTCC ATGCCACAGC AACCCTCGCA GCAACCCCAG GACTTTGGCC     900

TGCAGCCAGC TGGGCCACTG GGACAGTCCC ACCTGGCTCA CCACAGCATG GCACCCTACC     960

CCTTCCCCCC CAACCCAGAT ATGAACCCAG AACTGCGCAA GGCCCTTCTG CAGGACTCAG    1020

CCCCGCAGCC AGCGCTACCT CAGGTCCAGA TCCCCTTCCC CCGCCGCTCC CGCCGCCTCT    1080

CTAAGGAGGG TATCCTGCCT CCCAGCGCCC TGGATGGGGC TGGCACCCAG CCTGGGCAGG    1140

AGGCCACTGG CAACCTGTTC CTACATCACT GGCCCCTGCA GCAGCCGCCA CCTGGCTCCC    1200

TGGGGCAGCC CCATCCTGAA GCTCTGGGAT TCCCGCTGGA GCTGAGGGAG TCGCAGCTAC    1260

TGCCTGATGG GGAGAGACTA GCACCCAATG GCCGGAGCG AGAGGCTCCT GCCATGGGCA    1320

GCGAGGAGGG CATGAGGGCA GTGAGCACAG GGGACTGTGG GCAGGTGCTA CGGGGCGGAG    1380
```

-continued

```
TGATCCAGAG CACGCGACGG AGGCGCCGGG CATCCCAGGA GGCCAATTTG CTGACCCTGG    1440

CCCAGAAGGC TGTGGAGCTG GCCTCACTGC AGAATGCAAA GGATGGCAGT GGTTCTGAAG    1500

AGAAGCGGAA AAGTGTATTG GCCTCAACTA CCAAGTGTGG GGTGGAGTTT TCTGAGCCTT    1560

CCTTAGCCAC CAAGCGAGCA CGAGAAGACA GTGGGATGGT ACCCCTCATC ATCCCAGTGT    1620

CTGTGCCTGT GCGAACTGTG GACCCAACTG AGGCAGCCCA GGCTGGAGGT CTTGATGAGG    1680

ACGGGAAGGG TCTTGAACAG AACCCTGCTG AGCACAAGCC ATCAGTCATC GTCACCCGCA    1740

GGCGGTCCAC CCGAATCCCC GGGACAGATG CTCAAGCTCA GCGGAGGAC ATGAATGTCA    1800

AGTTGGAGGG GGAGCCTTCC GTGCGGAAAC CAAAGCAGCG GCCCAGGCCC GAGCCCCTCA    1860

TCATCCCCAC CAAGGCGGGC ACTTTCATCG CCCCTCCCGT CTACTCCAAC ATCACCCCAT    1920

ACCAGAGCCA CCTGCGCTCT CCCGTGCGCC TAGCTGACCA CCCCTCTGAG CGGAGCTTTG    1980

AGCTACCTCC CTACACGCCG CCCCCCATCC TCAGCCCTGT GCGGGAAGGC TCTGGCCTCT    2040

ACTTCAATGC CATCATATCA ACCAGCACCA TCCCTGCCCC TCCTCCCATC ACGCCTAAGA    2100

GTGCCCATCG CACGCTGCTC CGGACTAACA GTGCTGAAGT AACCCCGCCT GTCCTCTCTG    2160

TGATGGGGGA GGCCACCCCA GTGAGCATCG AGCCACGGAT CAACGTGGGC TCCCGGTTCC    2220

AGGCAGAAAT CCCCTTGATG AGGGACCGTG CCCTGGCAGC TGCAGATCCC CACAAGGCTG    2280

ACTTGGTGTG GCAGCCATGG GAGGACCTAG AGAGCAGCCG GGAGAAGCAG AGGCAAGTGG    2340

AAGACCTGCT GACAGCCGCC TGCTCCAGCA TTTTCCCTGG TGCTGGCACC AACCAGGAGC    2400

TGGCCCTGCA CTGTCTGCAC GAATCCAGAG GAGACATCCT GGAAACGCTG AATAAGCTGC    2460

TGCTGAAGAA GCCCCTGCGG CCCCACAACC ATCCGCTGGC AACTTATCAC TACACAGGCT    2520

CTGACCAGTG GAAGATGGCC GAGAGGAAGC TGTTCAACAA AGGCATTGCC ATCTACAAGA    2580

AGGATTTCTT CCTGGTGCAG AAGCTGATCC AGACCAAGAC CGTGGCCCAG TGCGTGGAGT    2640

TCTACTACAC CTACAAGAAG CAGGTGAAAA TCGGCCGCAA TGGGACTCTA ACCTTTGGGG    2700

ATGTGGATAC GAGCGATGAG AAGTCGGCCC AGGAAGAGGT TGAAGTGGAT ATTAAGACTT    2760

CCCAAAAGTT CCCAAGGGTG CCTCTTCCCA GAAGAGAGTC CCCAAGTGAA GAGAGGCTGG    2820

AGCCCAAGAG GGAGGTGAAG GAGCCCAGGA AGGAGGGGGA GGAGGAGGTG CCAGAGATCC    2880

AAGAGAAGGA GGAGCAGGAA GAGGGGCGAG AGCGCAGCAG GCGGGCAGCG GCAGTCAAAG    2940

CCACGCAGAC ACTACAGGCC AATGAGTCGG CCAGTGACAT CCTCATCCTC CGGAGCCACG    3000

AGTCCAACGC CCCTGGGTCT GCCGGTGGCC AGGCCTCGGA GAAGCCAAGG GAAGGGACAG    3060

GGAAGTCACG AAGGGCACTA CCTTTTTCAG AAAAAAAAAA AAAAAAACAA AAAGCTT     3117
```

(2) INFORMATION FOR SEQ ID NO:7:

(i) SEQUENCE CHARACTERISTICS:
        (A) LENGTH: 3306 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:7:

```
GAATTCGGCA CGAGGTCAGT TTCCTGTGGA ACACAGAGGC TGCCTGTCCC ATTCAGACAA      60

CGACGGATAC AGACCAGGCT TGCTCTATAA GGGATCCCAA CAGTGGATTT GTGTTTAATC     120

TTAATCCGCT AAACAGTTCG CAAGGATATA ACGTCTCTGG CATTGGGAAG ATTTTTATGT     180

TTAATGTCTG CGGCACAATG CCTGTCTGTG GGACCATCCT GGGAAAACCT GCTTCTGGCT     240
```

```
GTGAGGCAGA AACCCAAACT GAAGAGCTCA AGAATTGGAA GCCAGCAAGG CCAGTCGGAA    300

TTGAGAAAAG CCTCCAGCTG TCCACAGAGG GCTTCATCAC TCTGACCTAC AAAGGGCCTC    360

TCTCTGCCAA AGGTACCGCT GATGCTTTTA TCGTCCGCTT TGTTTGCAAT GATGATGTTT    420

ACTCAGGGCC CCTCAAATTC CTGCATCAAG ATATCGACTC TGGGCAAGGG ATCCGAAACA    480

CTTACTTTGA GTTTGAAACC GCGTTGGCCT GTGTTCCTTC TCCAGTGGAC TGCCAAGTCA    540

CCGACCTGGC TGGAAATGAG TACGACCTGA CTGGCCTAAG CACAGTCAGG AAACCTTGGA    600

CGGCTGTTGA CACCTCTGTC GATGGGAGAA AGAGGACTTT CTATTTGAGC GTTTGCAATC    660

CTCTCCCTTA CATTCCTGGA TGCCAGGGCA GCGCAGTGGG GTCTTGCTTA GTGTCAGAAG    720

GCAATAGCTG GAATCTGGGT GTGGTGCAGA TGAGTCCCCA AGCCGCGGCG AATGGATCTT    780

TGAGCATCAT GTATGTCAAC GGTGACAAGT GTGGGAACCA GCGCTTCTCC ACCAGGATCA    840

CGTTTGAGTG TGCTCAGATA TCGGGCTCAC CAGCATTTCA GCTTCAGGAT GGTTGTGAGT    900

ACGTGTTTAT CTGGAGAACT GTGGAAGCCT GTCCCGTTGT CAGAGTGGAA GGGGACAACT    960

GTGAGGTGAA AGACCCAAGG CATGGCAACT TGTATGACCT GAAGCCCCTG GGCCTCAACG   1020

ACACCATCGT GAGCGCTGGC GAATACACTT ATTACTTCCG GGTCTGTGGG AAGCTTTCCT   1080

CAGACGTCTG CCCCACAAGT GACAAGTCCA AGGTGGTCTC CTCATGTCAG GAAAAGCGGG   1140

AACCGCAGGG ATTTCACAAA GTGGCAGGTC TCCTGACTCA GAAGCTAACT TATGAAAATG   1200

GCTTGTTAAA AATGAACTTC ACGGGGGGG ACACTTGCCA TAAGGTTTAT CAGCGCTCCA    1260

CAGCCATCTT CTTCTACTGT GACCGCGGCA CCCAGCGGCC AGTATTTCTA AAGGAGACTT   1320

CAGATTGTTC CTACTTGTTT GAGTGGCGAA CGCAGTATGC CTGCCCACCT TTCGATCTGA   1380

CTGAATGTTC ATTCAAAGAT GGGGCTGGCA ACTCCTTCGA CCTCTCGTCC CTGTCAAGGT   1440

ACAGTGACAA CTGGGAAGCC ATCACTGGGA CGGGGACCC GGAGCACTAC CTCATCAATG    1500

TCTGCAAGTC TCTGGCCCCG CAGGCTGGCA CTGAGCCGTG CCCTCCAGAA GCAGCCGCGT   1560

GTCTGCTGGG TGGCTCCAAG CCCGTGAACC TCGGCAGGGT AAGGGACGGA CCTCAGTGGA   1620

GAGATGGCAT AATTGTCCTG AAATACGTTG ATGGCGACTT ATGTCCAGAT GGGATTCGGA   1680

AAAAGTCAAC CACCATCCGA TTCACCTGCA GCGAGAGCCA AGTGAACTCC AGGCCCATGT   1740

TCATCAGCGC CGTGGAGGAC TGTGAGTACA CCTTTGCCTG GCCCACAGCC ACAGCCTGTC   1800

CCATGAAGAG CAACGAGCAT GATGACTGCC AGGTCACCAA CCCAAGCACA GGACACCTGT   1860

TTGATCTGAG CTCCTTAAGT GGCAGGGCGG GATTCACAGC TGCTTACAGC GAGAAGGGGT   1920

TGGTTTACAT GAGCATCTGT GGGGAGAATG AAAACTGCCC TCCTGGCGTG GGGGCCTGCT   1980

TTGGACAGAC CAGGATTAGC GTGGGCAAGG CCAACAAGAG GCTGAGATAC GTGGACCAGG   2040

TCCTGCAGCT GGTGTACAAG GATGGGTCCC CTTGTCCCTC CAAATCCGGC CTGAGCTATA   2100

AGAGTGTGAT CAGTTTCGTG TGCAGGCCTG AGGCCGGGCC AACCAATAGG CCCATGCTCA   2160

TCTCCCTGGA CAAGCAGACA TGCACTCTCT TCTTCTCCTG GCACACGCCG CTGGCCTGCG   2220

AGCAAGCGAC CGAATGTTCC GTGAGGAATG GAAGCTCTAT TGTTGACTTG TCTCCCCTTA   2280

TTCATCGCAC TGGTGGTTAT GAGGCTTATG ATGAGAGTGA GGATGATGCC TCCGATACCA   2340

ACCCTGATTT CTACATCAAT ATTTGTCAGC CACTAAATCC CATGCACGGA GTGCCCTGTC   2400

CTGCCGGAGC CGCTGTGTGC AAAGTTCCTA TTGATGGTCC CCCCATAGAT ATCGGCCGGG   2460

TAGCAGGACC ACCAATACTC AATCCAATAG CAAATGAGAT TTACTTGAAT TTTGAAAGCA   2520

GTACTCCTTG CCAGGAATTC AGTTGTAAAT AAAAATTGAAC CTGCTCAACA GCTGAGGGAG   2580

ACTAGAAATG ATGGGTCCAT ATCCTGGTGC ATTGTCATAC AATTCAAACA ATGGTGCAGC   2640
```

-continued

```
TACCAGCTTG TAATTTTTAG GGACTGCAAA CAAGGCTTTT TCTTGAAGCT GAACCAGAAA    2700

CAACTTCTTA TGTTCCTTAG GCTTTGTAAT ATGTGCAGGA ATATATGGAT ACTGAGGAGG    2760

TTCAAAATTT GGTCTCCACC AGTTACCAAT GCAATCGTCA ATGACCCAGT CTTGCAAAAC    2820

TCCATCCTGA CGACCCAGTA TCTCTGTCAT TAAGCGTTTT AGTCCTTCAA CTTCATCTTC    2880

TCCTGGGTTA AGTTCACCAC CAGGTAGTTT GAAGAAAGTT GTTCCCAGCT GCAGCAGTAA    2940

CACATGGGGT AGCCGGTGCT CATGTACAAT CAGAACCCCT TCTACAGTCC TCCTCATTCC    3000

AATTTTATCA AATTCTTCCC TCATGCGCTG AAATCTGGCT GCAACAGAGC TGTCCTTCTC    3060

GTAGAGGGGC TCTTTTGTAC CAAAAGTATA ATTGGTAAGA GGGTACAGGT TGATGGTGCG    3120

CTCCAGGGTG AGGGGCTTCG TCTGCTGGAT GTACTTGTTG CCGAACTGAG TGACCCCCCG    3180

GGGCCAGCCG GTCTGCGAGC GATTGGGCGG TACCACAGAC ATGCTGGCGA GCTCCGGCGC    3240

TGACGGCGAG CAGAAAGTGG CAGGCAGGGT AGACTTTCCC CGTGCGGGAA GCCTCGTGCC    3300

GAATTC                                                               3306
```

(2) INFORMATION FOR SEQ ID NO:8:

(i) SEQUENCE CHARACTERISTICS:
        (A) LENGTH: 4218 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:8:

```
GAATTCGGCA CGAGAATGGA TCAACCTCAA CAACACGTTA AAGCTAGACG AAAGAAGTAA      60

TACACAGTGT ATGAGTCTCA CATGAAATAC CCGGATGTAA ATCCAAAGAA ACAGGAAGCA     120

GATTGGTGGT TGCCAGGGAC AAGGGCGGTG GGAGGAGAAA ATGGAGAGTA ACGGGACTTT     180

ACTTTTGGAG TGATGAGAAT GTTTTGGAGC TAGATAGAAG TGGTGGTTGT ACACCATTGT     240

GGATGTACTA CCACTTAATT GTTCACTTAA AAAGTTAATT TATGTGAATT GCATCTTAAT     300

TAAAAACAAG GATAACATTC CAACTCCTGG ACATTATCCT TCCTTTCCAT TTGATGTCAG     360

GCCCGTGTTA GAATTCTCAT CCGGTTTGGT CACTGCACTT AAGATGTGGA GAAATTAGGA     420

CGCACAGTTA AGAGGAAGGA TAACACTGAT TAAGGTAGTG CTTTTCTAGG TTTCCCCTAA     480

ACAATTTAAC AGATGGATAG TGGCACCACT TACGAGATGG AAAAACCAGC GGAAGGAAGA     540

TTTGGGGGAG AAGTTAAGTT TGTCTTGGGC CTGTGTTTTG CAACCTGAGT GTAAAAGACA     600

TATGTTAAGT CTTCAGTGGC GAAACACTAA AACTAGAAAT GGATCAGAAT TTTATCTTTG     660

GATGTGACTT CTCAAGGATG GTCTTGTCAC TTCAGTGCCT GGTCAAATGA CAAGATGGGC     720

AATCTTTTCC TGAAGGTCCA AGCACCTGAA CGTGGCAGGG TGACCCGATT CCGATTTGCT     780

TAGAACAATC CTAGTTCATG CCTATTGTCC CTCATGTAAT TAATATCACT CTCAAAATGT     840

CTCATTTTGT GCAATAAATT CTGCAACGTG ATGGCGCGAC TCTCGCGGCC CGAGCGGCCG     900

GACCTTGTCT TCGAGGAAGA GGACCTCCCC TATGAGGAGG AAATCATGCG GAACCAATTC     960

TCTGTCAAAT GCTGGCTTCA CTACATCGAG TTCAAACAGG CGCCCCGAA GCCCAGGCTC    1020

AATCAGCTAT ACGAGCGGGC ACTCAAGCTG CTGCCCTGCA GCTACAAACT CTGGTACCGA    1080

TACCTGAAGG CGCGTCGGGC ACAGGTGAAG CATCGCTGTG TGACCGACCC TGCCTATGAA    1140

GATGTCAACA ACTGTCATGA GAGGGCCTTT GTGTTCATGC ACAAGATGCC TCGTCTGTGG    1200

CTAGATTACT GCCAGTTCCT CATGGACCAG GGGCGCGTCA CACACACCCG CCGCACCTTC    1260
```

```
GACCGTGCCC TCCGGGCACT GCCCATCACG CAGCACTCTC GAATTTGGCC CCTGTATCTG   1320

CGCTTCCTGC GCTCACACCC ACTGCCTGAG ACAGCTGTGC GAGGCTATCG GCGCTTCCTC   1380

AAGCTGAGTC CTGAGAGTGC AGAGGAGTAC ATTGAGTACC TCAAGTCAAG TGACCGGCTG   1440

GATGAGGCCG CCCAGCGCCT GGCCACCGTG GTGAACGACG AGCGTTTCGT GTCTAAGGCC   1500

GGCAAGTCCA ACTACCAGCT GTGGCACGAG CTGTGCGACC TCATCTCCCA GAATCCGGAC   1560

AAGGTACAGT CCCTCAATGT GGACGCCATC ATCCGCGGGG GCCTCACCCG CTTCACCGAC   1620

CAGCTGGGCA AGCTCTGGTG TTCTCTCGCC GACTACTACA TCCGCAGCGG CCATTTCGAG   1680

AAGGCTCGGG ACGTGTACGA GGAGGCCATC CGGACAGTGA TGACCGTGCG GGACTTCACA   1740

CAGGTGTTTG ACAGCTACGC CCAGTTCGAG GAGAGCATGA TCGCTGCAAA GATGGAGACC   1800

GCCTCGGAGC TGGGGCGCGA GGAGGAGGAT GATGTGGACC TGGAGCTGCG CCTGGCCCGC   1860

TTCGAGCAGC TCATCAGCCG GCGGCCCCTG CTCCTCAACA GCGTCTTGCT GCGCCAAAAC   1920

CCACACCACG TGCACGAGTG GCACAAGCGT GTCGCCCTGC ACCAGGGCCG CCCCCGGGAG   1980

ATCATCAACA CCTACACAGA GGCTGTGCAG ACGGTGGACC CCTTCAAGGC CACAGGCAAG   2040

CCCCACACTC TGTGGGTGGC GTTTGCCAAG TTTTATGAGG ACAACGGACA GCTGGACGAT   2100

GCCCGTGTCA TCCTGGAGAA GGCCACCAAG GTGAACTTCA GCAGGTGGA TGACCTGGCA   2160

AGCGTGTGGT GTCAGTGCGG AGAGCTGGAG CTCCGACACG AGAACTACGA TGAGGCCTTG   2220

CGGCTGCTGC GAAAGGCCAC GGCGCTGCCT GCCCGCCGGG CCGAGTACTT TGATGGTTCA   2280

GAGCCCGTGC AGAACCGCGT GTACAAGTCA CTGAAGGTCT GGTCCATGCT CGCCGACCTG   2340

GAGGAGAGCC TCGGCACCTT CCAGTCCACC AAGGCCGTGT ACGACCGCAT CCTGGACCTG   2400

CGTATCGCAA CACCCCAGAT CGTCATCAAC TATGCCATGT TCCTGGAGGA GCACAAGTAC   2460

TTCGAGGAGA GCTTCAAGGC GTACGAGCGC GGCATCTCGC TGTTCAAGTG GCCCAACGTG   2520

TCCGACATCT GGAGCACCTA CCTGACCAAA TTCATTGCCC GCTATGGGGG CCGCAAGCTG   2580

GAGCGGGCAC GGGACCTGTT TGAACAGGCT CTGGACGGCT GCCCCCCAAA ATATGCCAAG   2640

ACCTTGTACC TGCTGTACGC ACAGCTGGAG GAGGAGTGGG GCCTGGCCCG GCATGCCATG   2700

GCCGTGTACG AGCGTGCCAC CAGGGCCGTG GAGCCCGCCC AGCAGTATGA CATGTTCAAC   2760

ATCTACATCA AGCGGGCGGC CGAGATCTAT GGGGTCACCC ACACCCGCGG CATCTACCAG   2820

AAGGCCATTG AGGTGCTGTC GGACGAGCAC GCGCGTGAGA TGTGCCTGCG GTTTGCAGAC   2880

ATGGAGTGCA AGCTCGGGGA GATTGACCGC GCCCGGGCCA TCTACAGCTT CTGCTCCCAG   2940

ATCTGTGACC CCCGGACGAC CGGCGCGTTC TGGCAGACGT GGAAGGACTT TGAGGTCCGG   3000

CATGGCAATG AGGACACCAT CAAGGAAATG CTGCGTATCC GGCGCAGCGT GCAGGCCACG   3060

TACAACACGC AGGTCAACTT CATGGCCTCG CAGATGCTCA AGGTCTCGGG CAGTGCCACG   3120

GGCACCGTGT CTGACCTGGC CCCTGGGCAG AGTGGCATGG ACGACATGAA GCTGCTGGAA   3180

CAGCGGGCAG AGCAGCTGGC GGCTGAGGCG GAGCGTGACC AGCCCTTGCG CGCCCAGAGC   3240

AAGATCCTGT TCGTGAGGAG TGACGCCTCC CGGGAGGAGC TGGCAGAGCT GGCACAGCAG   3300

GTCAACCCCG AGGAGATCCA GCTGGGCGAG GACGAGGACG AGGACGAGAT GGACCTGGAG   3360

CCCAACGAGG TTCGGCTGGA GCAGCAGAGC GTGCCAGCCG CAGTGTTTGG GAGCCTGAAG   3420

GAAGACTGAC CCGTCCCCTC GTGCCGAATT CGGCACGAGC AAGACCAGCC CCAGATCAT   3480

TTGCCTCAAA GGTTTTCCCT CGAAGTCACA AATGTTTCAA GGAATCTCAA ATTTTACAAA   3540

GTTTGAAGTG TGGGCATTGG TGGCCTGTGG CTGTGTCCTC TCTCTGTAGC TGTTTTCTCC   3600
```

-continued

```
CTACATCCCT GAAAGGAAGT TGAGCCTGCT CCTCCATCCG CAGACCTCCC TTTCCAGCGC    3660

CCAGGGCATG GGGTGCTGTG AGGGCAGCAT GCTAGGTGTG ACCGTGCTCC TGGCCTCCAG    3720

GCCCGTGTCC CTCTGTCCTC TAGCCCACTA AGGCCCTGGC CCATTTGTGC TAAACAGGCA    3780

GTCGGACCTA GAAAGAGCAG ACAATCTCTC TGGGTCACCA GTCTGGCTAG GAGCTGGTCT    3840

CCTGACTGGG ATCCAGGCCT TCTCCCCTGC CCATGTGAAT TCCCAGGGGC AGAGCCTGAA    3900

ATGTTGAACA CAGCACTGGC CAAAGAGATG TCACCGTGGG AACCGAGGCT CTCTTCTCCT    3960

CCTGCCTGCT TTCGTGGGTT CAGAGTAGCT GAGGCTTGTC TGAGAGGAGT TGGAGTGCTG    4020

GTTTTCACCC TGGTTGGTGT GCTTTGCTTT GAGGGCACTT AGAAAGCCCA GCCCAGCCCT    4080

TGCTCCTGCC CTGCACACAG CGGAGCGACT TTTCTAGGTA TGCTCTTGAT TTCTGCAGAA    4140

GCAGCAGGTG GCATGGAGCC AAGAGGAAGT GTGACTGAAA CTGTCCACTC ATAGCCCGGC    4200

TGCCGTATTG AGAGGGCT                                                  4218
```

(2) INFORMATION FOR SEQ ID NO:9:

(i) SEQUENCE CHARACTERISTICS:
        (A) LENGTH: 1187 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:9:

```
GAGCTCGCGC GCCTGCAGGT CGACACTAGT GGATCCAAAG AATTCGGCAC GAGGGAAACT      60

CAACGGTGTA CGAGTGGAGG ACAGGACAG AGCCCTCTGT GGTGGAACGA CCCCACCTCG      120

AGGAGCTTCC TGAGCAGGTG GCAGAAGATG CGATTGACTG GGGCGACTTT GGGGTAGAGG     180

CAGTGTCTGA GGGGACTGAC TCTGGCATCT CTGCCGAGGC TGCTGGAATC GACTGGGGCA     240

TCTTCCCGGA ATCAGATTCA AAGGATCCTG GAGGTGATGG GATAGACTGG GGAGACGATG     300

CTGTTGCTTT GCAGATCACA GTGCTGGAAG CAGGAACCCA GGCTCCAGAA GGTGTTGCCA     360

GGGGCCCAGA TGCCCTGACA CTGCTTGAAT ACACTGAGAC CCGGAATCAG TTCCTTGATG     420

AGCTCATGGA GCTTGAGATC TTCTTAGCCC AGAGAGCAGT GGAGTTGAGT GAGGAGGCAG     480

ATGTCCTGTC TGTGAGCCAG TTCCAGCTGG CTCCAGCCAT CCTGCAGGGC CAGACCAAAG     540

AGAAGATGGT TACCATGGTG TCAGTGCTGG AGGATCTGAT TGGCAAGCTT ACCAGTCTTC     600

AGCTGCAACA CCTGTTTATG ATCCTGGCCT CACCAAGGTA TGTGGACCGA GTGACTGAAT     660

TCCTCCAGCA AAAGCTGAAG CAGTCCCAGC TGCTGGCTTT GAAGAAAGAG CTGATGGTGC     720

AGAAGCAGCA GGAGGCACTT GAGGAGCAGG CGGCTCTGGA GCCTAAGCTG GACCTGCTAC     780

TGGAGAAGAC CAAGGAGCTG CAGAAGCTGA TTGAAGCTGA CATCTCCAAG AGGTACAGCG     840

GGCGCCCTGT GAACCTGATG GGAACCTCTC TGTGACACCC TCCGTGTTCT TGCCTGCCCA     900

TCTTCTCCGC TTTTGGGATG AAGATGATAG CCAGGGCTGT TGTTTTGGGG CCCTTCAAGG     960

CAAAAGACCA GGCTGACTGG AAGATGGAAA GCCACAGGAA GGAAGCGGCA CCTGATGGTG    1020

ATCTTGGCAC TCTCCATGTT CTCTACAAGA AGCTGTGGTG ATTGGCCCTG TGGTCTATCA    1080

GGCGAAAACC ACAGATTCTC CTTCTAGTTA GTATAGCGCA AAAGCTTCT CGAGAGTACT     1140

TCTAGAGCGG CCGCGGGCCC ATCGATTTTC CACCCGGGTG GGGTACC                  1187
```

(2) INFORMATION FOR SEQ ID NO:10:

(i) SEQUENCE CHARACTERISTICS:

(A) LENGTH: 3306 base pairs
(B) TYPE: nucleic acid
(C) STRANDEDNESS: double
(D) TOPOLOGY: linear (ii) MOLECULE TYPE: Genomic DNA (xi) SEQUENCE DESCRIPTION: SEQ ID NO:10:

```
CCCTCACTAA AGGGAACAAA AGCTGGAGCT CGCGCGCCTG CAGGTCGACA CTAGTGGATC    60
GAAAGTTCGT TACGCCAAGC TCGAAATTAA CTCTGGGCTG ACCCATAAAC ATTTGTCTGA   120
TCTAGGATAT AGTTGCGTTT CTTGCGGGCA GCAATCTGGA TGAGGCGGTT GAGGCACTGG   180
GTGGCCTGCT GGATCAGGAC ATCCCAGCGG CCAGCATAGT TCCGCTGCCG GCGTAGGCCC   240
ATCACCCGCA TCTTATCCAT GATGGCATTG GTACCCAGGA TGTTGTACTT CTTGGAAGGG   300
TTGGAGGCTG CATGTTTGAT GGCCCATGTG GTCTTGCCAG CAGCAGGCAG GCCCACCATC   360
ATCAGAATCT CACATTCTGC CTTGCTCTTT GGTCCAACGG TGCCCCGGAT ACGCTCACTA   420
AGGGGAAGGT GCTGGATGAA GGTAAACCCC GGGAGGACAG AACAGTAGGG CTCTGCTCTC   480
TGTCCGAAGT TGAACTCCAC TGCGCAATTC TTCACCAGGA CATGAGGATA GAGGGCCTGA   540
CCCCCCAAGG CTTCCTTCTG GATTCGGAAA GCAATGCCCA TCCACTTTCC ATTCTTGGTA   600
AAAGACAGTT CCACGTCATT TCCACATTCA AAATCCGCAA AGCAGCCAAT CACCGGAGAG   660
CTCTGCGGTG CTAGGAGAGC GGCTGGGCCC GCAGACTGGG GGGAAAGCTC CGCAGCCGCA   720
GTGGGCCCCA GGATCAGGCC CCGCGTGGCC TGGAGAAGCC CAGTCTGGGC TGGAGCGGGA   780
GCTGGACAGT GTGGCCTTGC GTTCGCCCCC GGGAGCGCTG CGAGTGTCGC GGCCTCGGGT   840
GGATTTGCTG AGCACCAATA CCTCACGGTT GCCAACCTGG GGTTTTAGCT CCCTTGGTTT   900
TAATCCCCTA GGGGCGGGTG GGGCACGGG  AGGAAGGATG GGCCAGCTGG GTGCAATCCT   960
GCTGTAAGCC AGCCATTCCT TGATTTCTTA GAATTAACTA AACGGTCGCG CCGGAGGCCG  1020
CGGGGGCCGG AGCGGAGCAG CCGCGGCTGA GGTTCCCGAG TCGGCCGCTC GGGGCTGCGC  1080
TCCGCCGCCG GGACCCCGGC TCTGGCCGC  GCCGGCTCCG GCCTCCGGGG GGGCCGGGC   1140
CGCCGGGACA TGGTGCCAGT CGCACCCCTT CCCCGCCGCC GCTGAGCTCG CCGGCCGCGC  1200
CCGGGCTGGG ACGTCCGAGC GGGAAGATGT TTTCCGCCCT GAAGAAGCTG GTGGGGTCGG  1260
ACCAGGCCCC GGGCCGGGAC AAGAACATCC CCGCCGGGCT GCAGTCCATG AACCAGGCGT  1320
TGCAGAGGCG CTTCGCCAAG GGGGTGCAGT ACAACATGAA GATAGTGATC CGGGGAGACA  1380
GGAACACGGG CAAGACAGCG CTGTGGCACC GCCTGCAGGG CCGGCCGTTC GTGGAGGAGT  1440
ACATCCCCAC ACAGGAGATC CAGGTCACCA GCATCCACTG GAGCTACAAG ACCACGGATG  1500
ACATCGTGAA GGTTGAAGTC TGGGATGTAG TAGACAAAGG AAAATGCAAA AAGCGAGGCG  1560
ACGGCTTAAA GATGGAGAAC GACCCCAGG  AGNCGGAGTC TGAAATGGCC CTGGATGCTG  1620
AGTTCCTGGA CGTGTACAAG AACTGCAACG GGTGGTCAT  GATGTTGAC  ATTACCAAGC  1680
AGTGGACCTT CAATTACATT CTCCGGGAGC TTCCAAAAGT GCCCACCCAC GTGCCAGTGT  1740
GCGTGCTGGG GAACTACCGG GACATGGGCG AGCACCGAGT CATCCTGCCG GACGACGTGC  1800
GTGACTTCAT CGACAACCTG GACAGACCTC CAGGTTCCTC CTACTTCCGC TATGCTGAGT  1860
CTTCCATGAA GAACAGCTTC GGCCTAAAGT ACCTTCATAA GTTCTTCAAT ATCCCATTTT  1920
TGCAGCTTCA GAGGGAGACG CTGTTGCGGC AGCTGGAGAC GAACCAGCTG ACATGGACG   1980
CCACGCTGGA GGAGCTGTCG GTGCAGCAGG AGACGGAGGA CCAGAACTAC GGCATCTTCC  2040
TGGAGATGAT GGAGGCTCGC AGCCGTGGCC ATGCGTCCCC ACTGGCGGCC AACGGGCAGA  2100
```

```
GCCCATCCCC GGGCTCCCAG TCACCAGTCC TGCCTGCACC CGCTGTGTCC ACGGGGAGCT    2160

CCAGCCCCGG CACACCCCAG CCCGCCCCAC AGCTGCCCCT CAATGCTGCC CCACCATCCT    2220

CTGTGCCCCC TGTACCACCC TCAGAGGCCC TGCCCCCACC TGCGTGCCCC TCAGCCCCCG    2280

CCCCACGGCG CAGCATCATC TCTAGGCTGT TTGGGACGTC ACCTGCCACC GAGGCAGCCC    2340

CTCCACCTCC AGAGCCAGTC CCGGCCGCAC AGGGCCCAGC AACGGTCCAG AGTGTGGAGG    2400

ACTTTGTTCC TGACGACCGC CTGGACCGCA GCTTCCTGGA AGACACAACC CCCGCCAGGG    2460

ACGAGAAGAA GGTGGGGGCC AAGGCTGCCC AGCAGGACAG TGACAGTGAT GGGGAGGCCC    2520

TGGGCGGCAA CCCGATGGTG GCAGGGTTCC AGGACGATGT GGACCTCGAA GACCAGCCAC    2580

GTGGGAGTCC CCCGCTGCCT GCAGGCCCCG TCCCCAGTCA AGACATCACT CTTTCGAGTG    2640

AGGAGGAAGC AGAAGTGGCA GCTCCCACAA AAGGCCCTGC CCCAGCTCCC CAGCAGTGCT    2700

CAGAGCCAGA GACCAAGTGG TCCTCCATAC CAGCTTCGAA GCCACGGAGG GGGACAGCTC    2760

CCACGAGGAC CGCAGCACCC CCCTGGCCAG GCGGTGTCTC TGTTCGCACA GGTCCGGAGA    2820

AGCGCAGCAG CACCAGGCCC CCTGCTGAGA TGGAGCCGGG GAAGGGTGAG CAGGCCTCCT    2880

CGTCGGAGAG TGACCCCGAG GGACCCATTG CTGCACAAAT GCTGTCCTTC GTCATGGATG    2940

ACCCCGACTT TGAGAGCGAG GGATCAGACA CACAGCGCAG GCGGATGAC TTTCCCGTGC    3000

GAGATGACCC CTCCGATGTG ACTGACGAGG ATGAGGGCCC TGCCGAGCCG CCCCCACCCC    3060

CCAAGCTCCC TCTCCCCGCC TTCAGACTGA AGAATGACTC GGACCTCTTC GGGCTGGGGC    3120

TGGAGGAGGC CGGACCCAAG GAGAGCAGTG AGGAAGGTAA GGAGGGCAAA ACCCCCTCTA    3180

AGGAGAAGAA AAAAAAACA AAAAGCTTCT CGAGAGTACT TCTAGAGCGG CCGCGGGCCC    3240

ATCGATTTTC CACCCGGGTG GGGTACCAGG TAAGTGTACC CAATTCGCCC TATAGTGAGT    3300

CGTATT                                                              3306
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

```
TGCGGGGCCA GAGTGGGCTG                                                  20
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

```
GCAGTCCTGG CCTGCGGATG                                                  20
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

```
GTCGACAGGA GAATTGGTTC                                                    20

(2) INFORMATION FOR SEQ ID NO:14:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:14:

GCCTGGGTTC GGTGCGGGAC                                                    20

(2) INFORMATION FOR SEQ ID NO:15:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:15:

TGGTCGGGTG TTTGTGAGTG                                                    20

(2) INFORMATION FOR SEQ ID NO:16:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:16:

CCTCTTCCGT CTCCTCAGTG                                                    20

(2) INFORMATION FOR SEQ ID NO:17:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:17:

GGATTGCTAG TCTCACAGAC                                                    20

(2) INFORMATION FOR SEQ ID NO:18:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:18:

TTAAGGGTGG CTGAAGGGAC                                                    20

(2) INFORMATION FOR SEQ ID NO:19:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:19:

ACCTTCCCTC CCTGTCACAG                                                    20
```

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:20:

TGGTCGGGTG TTTGTGAGTG                                              20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:21:

ACACCATTCC AGAAATTCAG                                              20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:22:

AAACTGCAGG TGGCTGAGTC                                              20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:23:

GTCCTAATGT TTTCAGGGAG                                              20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:24:

AAAACCTATG GTTACAATTC                                              20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:25:

TCCTAGACAT GGTTCAAGTG                                              20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:26:

GATATAATTA GTTCTCCATC                                               20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:27:

ATGCCTGTTC CAGGCTGCAC                                               20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

GGACGGCGAC CTCCACCCAC                                               20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:29:

GGGCTCCTCC GACGCCTGAG                                               20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:30:

AGTCTAGCCC TGGCCTTGAC                                               20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:31:

GTCACTGGGG ACTCCGGCAG                                               20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:32:

CAGCTTTCCC TGGGCACATG                          20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:33:

CACAGCTGTC TCAAGCCCAG                          20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:34:

ACTGTTCCCC CTACATGATG                          20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:35:

ATCATATCCT CTTGCTGGTC                          20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:36:

GTTCCCAGAG CTTGTCTGTG                          20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:37:

GTTTGGCAGA CTCATAGTTG                          20

(2) INFORMATION FOR SEQ ID NO:38:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (xi) SEQUENCE DESCRIPTION: SEQ ID NO:38:

TAGCAGGGAG CCATGACCTG                                                    20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:39:

CTTGGCGCCA GAAGCGAGAG                                                    20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:40:

CCTCTCTCTC TCTCTCTCTC                                                    20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:41:

TCCCCGCTGA TTCCGCCAAG                                                    20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:42:

CTTTTTGAAT TCGGCACGAG                                                    20

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:43:

CCCCTGGTCC GCACCAGTTC                                                    20

(2) INFORMATION FOR SEQ ID NO:44:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:44:

GAGAAGGGTC GGGGCGGCAG                                                    20

(2) INFORMATION FOR SEQ ID NO:45:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:45:

AAATCACATC GCGTCAACAC                                                    20

(2) INFORMATION FOR SEQ ID NO:46:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:46:

TAAGAGAGTC ATAGTTACTC                                                    20

(2) INFORMATION FOR SEQ ID NO:47:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:47:

GCTCTAGAAG TACTCTCGAG                                                    20

(2) INFORMATION FOR SEQ ID NO:48:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:48:

ACTCTGGCCA TCAGGAGATC                                                    20

(2) INFORMATION FOR SEQ ID NO:49:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:49:

CAGGCGTTGT AGATGTTCTG                                                    20

(2) INFORMATION FOR SEQ ID NO:50:

(i) SEQUENCE CHARACTERISTICS:

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:50:

AGTGGCAGGC AGAAGTAATG                                              20

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:51:

GGTTGGAGAA CTGGATGTAG                                              20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:52:

CTATTCAGAT GCAACGCCAG                                              20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:53:

CCATGGCACA CAGAGCAGAC                                              20

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:54:

GCTACCATGC AGAGACACAG                                              20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:55:

CAGGCTGACA AGAAAATCAG                                              20

(2) INFORMATION FOR SEQ ID NO:56:

(i) SEQUENCE CHARACTERISTICS:
        (A) LENGTH: 20 base pairs (B) TYPE: nucleic acid
        (C) STRANDEDNESS: single
        (D) TOPOLOGY: linear (xi) SEQUENCE DESCRIPTION: SEQ ID NO:56:

GGCACGCATA GAGGAGAGAC                                           20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:57:

TGGGTGATGC CTTTGCTGAC                                           20

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:58:

AAAACAAGAT CAAGGTGATG                                           20

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:59:

TTGCCCACAT TGCTATGGTG                                           20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:60:

GACCAAGATC AGAAGTAGAG                                           20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:61:

CCCCTGGGCC AATGATGTTG                                           20

(2) INFORMATION FOR SEQ ID NO:62:

(i) SEQUENCE CHARACTERISTICS:
        (A) LENGTH: 19 base pairs
        (B) TYPE: nucleic acid (C) STRANDEDNESS: single
        (D) TOPOLOGY: linear (xi) SEQUENCE DESCRIPTION: SEQ ID NO:62:

TCTTCCCACC ATAGCAATG                                                        19

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:63:

TGGTCTTGGT GACCAATGTG                                                       20

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:64:

ACACCTCGGT GACCCCTGTG                                                       20

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:65:

TCTCCAAGTT CGGCACAGTG                                                       20

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:66:

ACATGGGCTG CACTCACGAC                                                       20

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:67:

GATCCTCTGA ACCTGCAGAG                                                       20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single (D) TOPOLOGY: linear (xi) SEQUENCE DESCRIPTION: SEQ ID NO:68:

GGAAATGAGG TGGGGCGATC                                              20

(2) INFORMATION FOR SEQ ID NO:69:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:69:

CTTTGCCTTG GACAAGGATG                                              20

(2) INFORMATION FOR SEQ ID NO:70:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:70:

GCACCTGCCA TTGGGGGTAG                                              20

(2) INFORMATION FOR SEQ ID NO:71:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:71:

GGTGGAAGCC ATTGACGGTG                                              20

(2) INFORMATION FOR SEQ ID NO:72:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:72:

TGCGTCTCTC GTCGCTGCTG                                              20

(2) INFORMATION FOR SEQ ID NO:73:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:73:

GCGGAAACTC TGTGGTGCTG                                              20

(2) INFORMATION FOR SEQ ID NO:74:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:74:

AGGATTGCCT TCCTCTACTG                                             20

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:75:

TGTCTGTTTC ACCAGGGCAG                                             20

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:76:

CCAGTGCCTC TATGCATGTC                                             20

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:77:

AGGAAGCCCA CGCACACCAC                                             20

(2) INFORMATION FOR SEQ ID NO:78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:78:

CCCTTTGTTC CCTGATCTTC                                             20

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:79:

CGCTCGGGAT CCAGGTCATC                                             20

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:80:

TCGAGGTTCA GAGCGTAGTG                                        20

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:81:

TCTTGGATCT CTGGCACCTC                                        20

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:82:

CCATCAGAGT GAAGGAGGAG                                        20

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:83:

CCATCTTCCA CTGGTCAGAG                                        20

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:84:

CTCCTTCTCT TGGATCTCTG                                        20

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:85:

TTACTTCAGC ACTGTTAGTC                                        20

(2) INFORMATION FOR SEQ ID NO:86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:86:

AGGGAGGTAG CTCAAAGCTC                                              20

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:87:

TGGGTCCACA GTTCGCACAG                                              20

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:88:

CAACTCTGTG ATGGCTCCAG                                              20

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:89:

AGCAGGGTTC TGTTCAAGAC                                              20

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:90:

CCATTGGGTG CTAGTCTCTC                                              20

(2) INFORMATION FOR SEQ ID NO:91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:91:

CAGCCATGCT GTCCCAGCAG                                              20

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:92:

```
CTGGACCTGA GGTAGCGCTG                                                    20

(2) INFORMATION FOR SEQ ID NO:93:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:93:

ATAACCACCC TGAGGCACTG                                                    20

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:94:

CCTGCAGGTC GACACTAGTG                                                    20

(2) INFORMATION FOR SEQ ID NO:95:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:95:

AATTGGAATG AGGAGGACTG                                                    20

(2) INFORMATION FOR SEQ ID NO:96:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:96:

GCTCTAGAAG TACTCTCGAG                                                    20

(2) INFORMATION FOR SEQ ID NO:97:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:97:

ATTGTATGAC AATGCACCAG                                                    20

(2) INFORMATION FOR SEQ ID NO:98:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:98:

TCCACAGAGG GCTTCATCAC                                                    20
```

(2) INFORMATION FOR SEQ ID NO:99:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:99:

```
CCTGACTGGC CTAAGCACAG                                              20
```

(2) INFORMATION FOR SEQ ID NO:100:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:100:

```
AAGCCTCATA ACCACCAGTG                                              20
```

(2) INFORMATION FOR SEQ ID NO:101:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:101:

```
TGTCAACGGT GACAAGTGTG                                              20
```

(2) INFORMATION FOR SEQ ID NO:102:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:102:

```
TTGTACACCA GCTGCAGGTC                                              20
```

(2) INFORMATION FOR SEQ ID NO:103:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:103:

```
GGGTGTGGTG CAGATGAGTC                                              20
```

(2) INFORMATION FOR SEQ ID NO:104:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:104:

```
ATCACACTCT TATAGCTCAG                                              20
```

(2) INFORMATION FOR SEQ ID NO:105:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:105:

GTGGGAAGCT TTCCTCAGAC                                               20

(2) INFORMATION FOR SEQ ID NO:106:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:106:

TGATGAACAT GGGCCTGGAG                                               20

(2) INFORMATION FOR SEQ ID NO:107:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:107:

CATTGTGGAT GTACTACCAC                                               20

(2) INFORMATION FOR SEQ ID NO:108:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:108:

TGTGTTTTGC AACCTGAGTG                                               20

(2) INFORMATION FOR SEQ ID NO:109:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:109:

ATAGTGGCAC CACTTACGAG                                               20

(2) INFORMATION FOR SEQ ID NO:110:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:110:

AATTCTGCAA CGTGATGGCG                                               20

(2) INFORMATION FOR SEQ ID NO:111:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:111:

CACAAGATGC CTCGTCTGTG                                               20

(2) INFORMATION FOR SEQ ID NO:112:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:112:

AATCCGGACA AGGTACAGTC                                               20

(2) INFORMATION FOR SEQ ID NO:113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:113:

GCACGAGTGG CACAAGCGTG                                               20

(2) INFORMATION FOR SEQ ID NO:114:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:114:

GCAAGCGTGT GGTGTCAGTG                                               20

(2) INFORMATION FOR SEQ ID NO:115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:115:

TGTTTGAACA GGCTCTGGAC                                               20

(2) INFORMATION FOR SEQ ID NO:116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:116:

CGGCATGGCA ATGAGGACAC                                               20

(2) INFORMATION FOR SEQ ID NO:117:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:117:

AGGACGAGAT GGACCTCCAG                                          20

(2) INFORMATION FOR SEQ ID NO:118:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:118:

CCCTCTGTCC TCTAGCCCAC                                          20

(2) INFORMATION FOR SEQ ID NO:119:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:119:

TCTTGAGGGG ACTGACTCTG                                          20

(2) INFORMATION FOR SEQ ID NO:120:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:120:

TGAGTGAGGA GGCAGATGTC                                          20

(2) INFORMATION FOR SEQ ID NO:121:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:121:

TGGCTTTGAA GAAAGAGCTG                                          20

(2) INFORMATION FOR SEQ ID NO:122:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:122:

GCAAAAGACC AGGCTGACTG                                          20

(2) INFORMATION FOR SEQ ID NO:123:
```

```
      (i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:123:

TGCAGCTCCT TGGTCTTCTC                                                20

(2) INFORMATION FOR SEQ ID NO:124:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:124:

GATTCACAGT CCCAAGGCTC                                                20

(2) INFORMATION FOR SEQ ID NO:125:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:125:

ATCTGGATGA GGCGGTTGAG                                                20

(2) INFORMATION FOR SEQ ID NO:126:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:126:

GGTCACTCTC CGACGAGGAG                                                20

(2) INFORMATION FOR SEQ ID NO:127:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:127:

GGATCCAAAG TTCGTCTCTG                                                20

(2) INFORMATION FOR SEQ ID NO:128:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:128:

CGCTGTGTGT CTGATCCCTC                                                20

(2) INFORMATION FOR SEQ ID NO:129:

(i) SEQUENCE CHARACTERISTICS:
```

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:129:

ATGAAGGTAA ACCCCGGGAG                                            20

(2) INFORMATION FOR SEQ ID NO:130:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:130:

TGGTCTCTGG CTCTGAGCAC                                            20

(2) INFORMATION FOR SEQ ID NO:131:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:131:

GCCTGGAGAA GCCCAGTCTG                                            20

(2) INFORMATION FOR SEQ ID NO:132:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:132:

CACACTCTGG ACCGTTGCTG                                            20

(2) INFORMATION FOR SEQ ID NO:133:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:133:

AAAGCTCCGC AGCCGCAGTG                                            20

(2) INFORMATION FOR SEQ ID NO:134:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:134:

TCTTCCAGGA AGCTGCGGTC                                            20

(2) INFORMATION FOR SEQ ID NO:135:

(i) SEQUENCE CHARACTERISTICS:
        (A) LENGTH: 20 base pairs (B) TYPE: nucleic acid
        (C) STRANDEDNESS: single
        (D) TOPOLOGY: linear (xi) SEQUENCE DESCRIPTION: SEQ ID NO:135:

GATGGTGGGG CAGCATTGAG                                            20

(2) INFORMATION FOR SEQ ID NO:136:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:136:

GTCACCAGTG GTGCCTGCAG                                            20

(2) INFORMATION FOR SEQ ID NO:137:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:137:

ACCTCACGGT TGCCAACCTG                                            20

(2) INFORMATION FOR SEQ ID NO:138:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:138:

CGCAACAGCG TCTCCCTCTG                                            20

(2) INFORMATION FOR SEQ ID NO:139:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:139:

AGTACCTTCA TAAGTTCTTC                                            20

(2) INFORMATION FOR SEQ ID NO:140:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:140:

TCCCAGACTT CAACCTTCAC                                            20

(2) INFORMATION FOR SEQ ID NO:141:

(i) SEQUENCE CHARACTERISTICS:
        (A) LENGTH: 20 base pairs
        (B) TYPE: nucleic acid (C) STRANDEDNESS: single
            (D) TOPOLOGY: linear (xi) SEQUENCE DESCRIPTION: SEQ ID NO:141:

AAACATCTTC CCGGTCGGAC                                                     20

(2) INFORMATION FOR SEQ ID NO:142:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:142:

GCTGAGCACC TTTACCTCAC                                                     20

(2) INFORMATION FOR SEQ ID NO:143:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:143:

GACGTCCGTC CGGGAAGATG                                                     20

(2) INFORMATION FOR SEQ ID NO:144:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:144:

ACACAGGAGA TGCAGGTCAC                                                     20

(2) INFORMATION FOR SEQ ID NO:145:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:145:

GAGTCTTCCA TGAAGAACAG                                                     20

(2) INFORMATION FOR SEQ ID NO:146:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:146:

GCAGTGAGGA AGGTAAGGAG                                                     20

(2) INFORMATION FOR SEQ ID NO:147:

(i) SEQUENCE CHARACTERISTICS:
            (A) LENGTH: 4047 base pairs
            (B) TYPE: nucleic acid
            (C) STRANDEDNESS: double (D) TOPOLOGY: linear (ii) MOLECULE TYPE: Genomic DNA (ix) FEATURE:
        (A) NAME/KEY: Coding Sequence
        (B) LOCATION: 378...1799
        (D) OTHER INFORMATION:

(xi) SEQUENCE DESCRIPTION: SEQ ID NO:147:

```
GGATCCAAAG GACGCCCCCG CCGACAGGAG AATTGGTTCC CGGGCCCGCG GCGATGCCCC      60

CCCGGTAGCT CGGGCCCGTG GTCGGGTGTT TGTGAGTGTT TCTATGTGGG AGAAGGAGGA     120

GGAGGAGGAA GAAGAAGCAA CGATTTGTCT TCTCGGCTGG TCTCCCCCCG GCTCTACATG     180

TTCCCCGCAC TGAGGAGACG GAAGAGGAGC CGTAGCCGCC CCCCCTCCCG GCCCGGATTA     240

TAGTCTCTCG CCACAGCGGC CTCGGCCTCC CCTTGGATTC AGACGCCGAT TCGCCCAGTG     300

TTTGGGAAAT GGGAAGTAAT GACAGCTGGC ACCTGAACTA AGTACTTTTA TAGGCAACAC     360

CATTCCAGAA ATTCAGG ATG AAT GGG GAT ATG CCC CAT GTC CCC ATT ACT        410
                   Met Asn Gly Asp Met Pro His Val Pro Ile Thr
                    1               5                      10

ACT CTT GCG GGG ATT GCT AGT CTC ACA GAC CTC CTG AAC CAG CTG CCT       458
Thr Leu Ala Gly Ile Ala Ser Leu Thr Asp Leu Leu Asn Gln Leu Pro
             15                  20                  25

CTT CCA TCT CCT TTA CCT GCT ACA ACT ACA AAG AGC CTT CTC TTT AAT       506
Leu Pro Ser Pro Leu Pro Ala Thr Thr Thr Lys Ser Leu Leu Phe Asn
         30                  35                  40

GCA CGA ATA GCA GAA GAG GTG AAC TGC CTT TTG GCT TGT AGG GAT GAC       554
Ala Arg Ile Ala Glu Glu Val Asn Cys Leu Leu Ala Cys Arg Asp Asp
     45                  50                  55

AAT TTG GTT TCA CAG CTT GTC CAT AGC CTC AAC CAG GTA TCA ACA GAT       602
Asn Leu Val Ser Gln Leu Val His Ser Leu Asn Gln Val Ser Thr Asp
 60                  65                  70                  75

CAC ATA GAG TTG AAA GAT AAC CTT GGC AGT GAT GAC CCA GAA GGT GAC       650
His Ile Glu Leu Lys Asp Asn Leu Gly Ser Asp Asp Pro Glu Gly Asp
                 80                  85                  90

ATA CCA GTC TTG TTG CAG GCC GTC CTG GCA AGG AGT CCT AAT GTT TTC       698
Ile Pro Val Leu Leu Gln Ala Val Leu Ala Arg Ser Pro Asn Val Phe
             95                 100                 105

AGG GAG AAA AGC ATG CAG AAC AGA TAT GTA CAA AGT GGA ATG ATG ATG       746
Arg Glu Lys Ser Met Gln Asn Arg Tyr Val Gln Ser Gly Met Met Met
         110                 115                 120

TCT CAG TAT AAA CTT TCT CAG AAT TCC ATG CAC AGT AGT CCT GCA TCT       794
Ser Gln Tyr Lys Leu Ser Gln Asn Ser Met His Ser Ser Pro Ala Ser
     125                 130                 135

TCC AAT TAT CAA CAA ACC ACT ATC TCA CAT AGC CCC TCC AGC CGG TTT       842
Ser Asn Tyr Gln Gln Thr Thr Ile Ser His Ser Pro Ser Ser Arg Phe
140                 145                 150                 155

GTG CCA CCA CAG ACA AGC TCT GGG AAC AGA TTT ATG CCA CAG CAA AAT       890
Val Pro Pro Gln Thr Ser Ser Gly Asn Arg Phe Met Pro Gln Gln Asn
                160                 165                 170

AGC CCA GTG CCT AGT CCA TAC GCC CCA CAA AGC CCT GCA GGA TAC ATG       938
Ser Pro Val Pro Ser Pro Tyr Ala Pro Gln Ser Pro Ala Gly Tyr Met
            175                 180                 185

CCA TAT TCC CAT CCT TCA AGT TAC ACA ACA CAT CCA CAG ATG CAA CAA       986
Pro Tyr Ser His Pro Ser Ser Tyr Thr Thr His Pro Gln Met Gln Gln
        190                 195                 200

GCA TCG GTA TCA AGT CCC ATT GTT GCA GGT GGT TTG AGA AAC ATA CAT      1034
Ala Ser Val Ser Ser Pro Ile Val Ala Gly Gly Leu Arg Asn Ile His
    205                 210                 215
```

```
GAT AAT AAA GTT TCT GGT CCG TTG TCT GGC AAT TCA GCT AAT CAT CAT   1082
Asp Asn Lys Val Ser Gly Pro Leu Ser Gly Asn Ser Ala Asn His His
220             225             230             235

GCT GAT AAT CCT AGA CAT GGT TCA AGT GAG GAC TAC CTA CAC ATG GTG   1130
Ala Asp Asn Pro Arg His Gly Ser Ser Glu Asp Tyr Leu His Met Val
            240             245             250

CAC AGG CTA AGT AGT GAC GAT GGA GAT TCT TCA ACA ATG AGG AAT GCT   1178
His Arg Leu Ser Ser Asp Asp Gly Asp Ser Ser Thr Met Arg Asn Ala
                255             260             265

GCA TCT TTT CCC TTG AGA TCT CCA CAG CCA GTA TGC TCC CCT GCT GGA   1226
Ala Ser Phe Pro Leu Arg Ser Pro Gln Pro Val Cys Ser Pro Ala Gly
        270             275             280

AGT GAA GGA ACT CCT AAA GGC TCA AGA CCA CCT TTA ATC CTA CAA TCT   1274
Ser Glu Gly Thr Pro Lys Gly Ser Arg Pro Pro Leu Ile Leu Gln Ser
        285             290             295

CAG TCT CTA CCT TGT TCA TCA CCT CGA GAT GTT CCA CCA GAT ATC TTG   1322
Gln Ser Leu Pro Cys Ser Ser Pro Arg Asp Val Pro Pro Asp Ile Leu
300             305             310             315

CTA GAT TCT CCA GAA AGA AAA CAA AAG AAG CAG AAG AAA ATG AAA TTA   1370
Leu Asp Ser Pro Glu Arg Lys Gln Lys Lys Gln Lys Lys Met Lys Leu
                320             325             330

GGC AAG GAT GAA AAA GAG CAG AGT GAG AAA GCG GCA ATG TAT GAT ATA   1418
Gly Lys Asp Glu Lys Glu Gln Ser Glu Lys Ala Ala Met Tyr Asp Ile
            335             340             345

ATT AGT TCT CCA TCC AAG GAC TCT ACT AAA CTT ACA TTA AGA CTT TCT   1466
Ile Ser Ser Pro Ser Lys Asp Ser Thr Lys Leu Thr Leu Arg Leu Ser
        350             355             360

CGT GTA AGG TCT TCA GAC ATG GAC CAG CAA GAG GAT ATG ATT TCT GGT   1514
Arg Val Arg Ser Ser Asp Met Asp Gln Gln Glu Asp Met Ile Ser Gly
        365             370             375

GTG GAA AAT AGC AAT GTT TCA GAA AAT GAT ATT CCT TTT AAT GTG CAG   1562
Val Glu Asn Ser Asn Val Ser Glu Asn Asp Ile Pro Phe Asn Val Gln
380             385             390             395

TAC CCA GGA CAG ACT TCA AAA ACA CCC ATT ACT CCA CAA GAT ATA AAC   1610
Tyr Pro Gly Gln Thr Ser Lys Thr Pro Ile Thr Pro Gln Asp Ile Asn
                400             405             410

CGC CCA CTA AAT GCT GCT CAA TGT TTG TCG CAG CAA GAA CAA ACA GCA   1658
Arg Pro Leu Asn Ala Ala Gln Cys Leu Ser Gln Gln Glu Gln Thr Ala
            415             420             425

TTC CTT CCA GCA AAT CAA GTG CCT GTT TTA CAA CAG AAC ACT TCA GTT   1706
Phe Leu Pro Ala Asn Gln Val Pro Val Leu Gln Gln Asn Thr Ser Val
        430             435             440

GCT GCA AAA CAA CCC CAG ACC AAT AGT CAC AAA ACC TTG GTG CAG CCT   1754
Ala Ala Lys Gln Pro Gln Thr Asn Ser His Lys Thr Leu Val Gln Pro
        445             450             455

GGA ACA GGC ATA GAG GTC TCA GCA GAG CTG CCC AAG GAC AAG ACC TAAGA 1804
Gly Thr Gly Ile Glu Val Ser Ala Glu Leu Pro Lys Asp Lys Thr
460             465             470

TCCAGCAGGG AACTATGTAG TCACCCCGAG AGGCCCAGCT CTCTCCGTGA GCTCTGGGCC  1864

TAGGGTGGGG GTGGTTGTTG GTTCTGCGCG CACTGTTCCC CCTACATGAT GGGTCCATCC  1924

CAGTTGGCTT CTCTCACTCG CTTCCTCCTG TGGAGAAGCC TGTCCAGGTG TCACTGCCTC  1984

CAGGAAGCTG TCTCTGATTT CTCCAGTTGA ACAGTGAGAT TTGCCACACC TCACATGCAT  2044

CGCTCTTGTC CCTGGAATTG TAACCATAGG TTTTCCTGTC TCCTGGAGGA CAAGGATGAG  2104

GGCTTTCCAC TTGAGTCTCC CTGGTGGAGC CCAGCTCCTG ACATACCTGG TAAAAGTTCT  2164

CAAGAGAAGA ACATGGAGGA GGAATGTGGA TAACAACCCT GGCTGCCTGT GTGTTCCAAG  2224

CTAGGAAGAT GTAATGTCCC CACAAACGGG GTAAATGGCT TGCCTGCGTC ACAGCTGTCT  2284
```

-continued

```
CAAGCCCAGG CCCTGGGCGC CAGCCCAAGC CCAAGGACTA GGTCCAGAGC CACACAGCGC    2344

CAGGCCACAT CCGCCTCACC TGGGACCCTT TGTGGGGTAC AGTCTCCGGC CCCACCCAGA    2404

CCTCCTGAAG GAGAGACCCC ATGGCAAGGA CTCAGCCACC TGCAGTTTCA TAAGCCCCCA    2464

GTGGGTTCCT AGGCATGAAG ACCACCGGTT AGAGGCTGAA CTGGCAGGAA CCTGTCTCCA    2524

GCCCCTTCTC ACCCCAGCCG GGCCCTGCCT CAGAGGCAGC ACCCAGGACG TGGCCATGAC    2584

CCGTGGACTC CACTCAATCC CTCTTCTCCA GGAGCCATGC AAAGTGTCAG CCAGCCAGGC    2644

CCCTGGAAGG CAGTCATCAC CTCTTAAGGC ATTGTGGGTG TCGGTCCTGC AACTGCCAGG    2704

TGCAGCACAC GACCCGTGTC CGGTGTTCGA TAGCAGGGAG CCATGACCTG GCAACGATTC    2764

CACGCTCAAA GGGGCACCCG GGGGCCCTG GGTCGGGCG GATCAGCTTT CCCTGGGCAC      2824

ATCTGCCTCA TTCCAGATCT CCAGGGCTCA TGTCTGTGAC AGGGAGGGAA GGCTCTGCCC    2884

TGGCCTTCCG TCAGCTCTGC CAGTGCAGGC TGGGCAGCCT GGGCTTTAGA GCTGGCTTCT    2944

GCCCACACTT TCTCCGTGAA AGGAAAACAA CTATGAGTCT GCCAAACGCA TCTCAGATGC    3004

GTTTTAAAAA ATTCTGGTCC CCGCTCTCTG TCCCATCATC CGCCTCGGGG ACTTCCTCTC    3064

TCCGTGGTTC TCACCCCATA CTCTGTCACT GCCACATTTT CACCTGGGCC TGGCCTTTGT    3124

CTCCACCTGA AACTCCTGAA AATCTTGAAA TGGATTTCTA GGTCACTGGG GACTCCGGCA    3184

GCACATTCGG CTTCAGAATA AAGGGCGCCC GCGGTCCCCC AGCACCTCCC CAAGCCACAC    3244

CCCTAGCTTC CCTCCCTATC CCTGCAGCCT GAGGGTCCCT TCAGCCACCC TTAAGTCCCC    3304

ACCTGGGCTC CTGCCCCGCC CCTGGCTAGC AGCGCCTTCT CCACCGGGGC CCCCTCTGCT    3364

CACAGAGCCC CCTCACCTCC CTGGGGATGA GGGGCCAGGC CATGACCCTG AAAGTCTAGC    3424

CCTGGCCTTG ACCTCCCAGG AGCGCCCTCC CCGCCCTCTC CCGGCCCCGG CCCCGTCCTC    3484

TGCTGCTGGC CTCTGGGTCG TGCCCCGCAG ACTGAGCTGC GCTTGGGGGT CCTGGCGGCC    3544

TGGGCCGTCC CGCACCGAAC CCAGGCGGTC GGAGCCCGGC GGGAAGGCGC GAGGTCCTTC    3604

TGGGGGCTCC TCCGACGCCT GAGGGCGCTG CTTCCCCGCG GCCGCCCCGG GTTTCTGCGG    3664

AGCCGGGGCC TCCGCTCTCG GGTGACCCGG TGAGACCCCC GGGGAGGCCG CTGGGGAGGC    3724

GCGGGCTCTG CTCCCGGGTC CCAAACGCAC TGGCTGCCCC TCAGGAGGGA CGGCGACCTC    3784

CACCCACGGC GCTGGCGCCC GCACGGCCGC TCCTCCCGCT CCCGCAGCCT GGACGCCTCC    3844

CGAGGCCGCC CCGCCGGGCC CCACGCGCGG CCCCATCCGC AGGCCAGGAC TGCCTTCCCG    3904

GAGCTGGCGG CCCCCAGCCT GGAGGAGCCG GCCCCAGACG CCCTCCCAGC CCTCCCCAGC    3964

CCACTCTGGC CCCGCAGCCC CCGCCTGGTC CGAGTGCGGG TCTCTGGCCC CGGCCTTTCC    4024

CGGGGAAGGA AAGCAAAAAG CTT                                            4047
```

(2) INFORMATION FOR SEQ ID NO:148:

(i) SEQUENCE CHARACTERISTICS:
        (A) LENGTH: 474 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:148:

```
Met Asn Gly Asp Met Pro His Val Pro Ile Thr Thr Leu Ala Gly Ile
 1               5                  10                  15
```

-continued

```
Ala Ser Leu Thr Asp Leu Leu Asn Gln Leu Pro Leu Pro Ser Pro Leu
             20                  25                  30
Pro Ala Thr Thr Thr Lys Ser Leu Leu Phe Asn Ala Arg Ile Ala Glu
         35                  40                  45
Glu Val Asn Cys Leu Leu Ala Cys Arg Asp Asp Asn Leu Val Ser Gln
     50                  55                  60
Leu Val His Ser Leu Asn Gln Val Ser Thr Asp His Ile Glu Leu Lys
 65                  70                  75                  80
Asp Asn Leu Gly Ser Asp Asp Pro Glu Gly Asp Ile Pro Val Leu Leu
                 85                  90                  95
Gln Ala Val Leu Ala Arg Ser Pro Asn Val Phe Arg Glu Lys Ser Met
            100                 105                 110
Gln Asn Arg Tyr Val Gln Ser Gly Met Met Met Ser Gln Tyr Lys Leu
            115                 120                 125
Ser Gln Asn Ser Met His Ser Ser Pro Ala Ser Ser Asn Tyr Gln Gln
        130                 135                 140
Thr Thr Ile Ser His Ser Pro Ser Arg Phe Val Pro Pro Gln Thr
145                 150                 155                 160
Ser Ser Gly Asn Arg Phe Met Pro Gln Gln Asn Ser Pro Val Pro Ser
                165                 170                 175
Pro Tyr Ala Pro Gln Ser Pro Ala Gly Tyr Met Pro Tyr Ser His Pro
            180                 185                 190
Ser Ser Tyr Thr Thr His Pro Gln Met Gln Gln Ala Ser Val Ser Ser
        195                 200                 205
Pro Ile Val Ala Gly Gly Leu Arg Asn Ile His Asp Asn Lys Val Ser
210                 215                 220
Gly Pro Leu Ser Gly Asn Ser Ala Asn His His Ala Asp Asn Pro Arg
225                 230                 235                 240
His Gly Ser Ser Glu Asp Tyr Leu His Met Val His Arg Leu Ser Ser
                245                 250                 255
Asp Asp Gly Asp Ser Ser Thr Met Arg Asn Ala Ala Ser Phe Pro Leu
            260                 265                 270
Arg Ser Pro Gln Pro Val Cys Ser Pro Ala Gly Ser Glu Gly Thr Pro
        275                 280                 285
Lys Gly Ser Arg Pro Pro Leu Ile Leu Gln Ser Gln Ser Leu Pro Cys
290                 295                 300
Ser Ser Pro Arg Asp Val Pro Pro Asp Ile Leu Leu Asp Ser Pro Glu
305                 310                 315                 320
Arg Lys Gln Lys Lys Gln Lys Lys Met Lys Leu Gly Lys Asp Glu Lys
            325                 330                 335
Glu Gln Ser Glu Lys Ala Ala Met Tyr Asp Ile Ile Ser Ser Pro Ser
        340                 345                 350
Lys Asp Ser Thr Lys Leu Thr Leu Arg Leu Ser Arg Val Arg Ser Ser
    355                 360                 365
Asp Met Asp Gln Gln Glu Asp Met Ile Ser Gly Val Glu Asn Ser Asn
370                 375                 380
Val Ser Glu Asn Asp Ile Pro Phe Asn Val Gln Tyr Pro Gly Gln Thr
385                 390                 395                 400
Ser Lys Thr Pro Ile Thr Pro Gln Asp Ile Asn Arg Pro Leu Asn Ala
            405                 410                 415
Ala Gln Cys Leu Ser Gln Gln Glu Gln Thr Ala Phe Leu Pro Ala Asn
        420                 425                 430
Gln Val Pro Val Leu Gln Gln Asn Thr Ser Val Ala Ala Lys Gln Pro
```

```
              435                 440                 445
    Gln Thr Asn Ser His Lys Thr Leu Val Gln Pro Gly Thr Gly Ile Glu
            450                 455                 460

Val Ser Ala Glu Leu Pro Lys Asp Lys Thr
    465                 470

(2) INFORMATION FOR SEQ ID NO:149:

(i) SEQUENCE CHARACTERISTICS:
        (A) LENGTH: 2998 base pairs
        (B) TYPE: nucleic acid
        (C) STRANDEDNESS: double
        (D) TOPOLOGY: linear (ii) MOLECULE TYPE: Genomic DNA (ix) FEATURE:
        (A) NAME/KEY: Coding Sequence
        (B) LOCATION: 26...799
        (D) OTHER INFORMATION:

(xi) SEQUENCE DESCRIPTION: SEQ ID NO:149:

AAGCTTTTTG AATTCGGCAC GAGAT GCT ACA CAG GCT ATA TTT GAA ATA CTG         52
                           Ala Thr Gln Ala Ile Phe Glu Ile Leu
                            1               5

GAG AAA TCC TGG TTG CCC CAG AAT TGT ACA CTG GTT GAT ATG AAG ATT        100
Glu Lys Ser Trp Leu Pro Gln Asn Cys Thr Leu Val Asp Met Lys Ile
10              15                  20                  25

GAA TTT GGT GTT GAT GTA ACC ACC AAA GAA ATT GTT CTT GCT GAT GTT        148
Glu Phe Gly Val Asp Val Thr Thr Lys Glu Ile Val Leu Ala Asp Val
                30                  35                  40

ATT GAC AAT GAT TCC TGG AGA CTC TGG CCA TCA GGA GAT CGA AGC CAA        196
Ile Asp Asn Asp Ser Trp Arg Leu Trp Pro Ser Gly Asp Arg Ser Gln
            45                  50                  55

CAG AAA GAC AAA CAG TCT TAT CGG GAC CTC AAA GAA GTA ACT CCT GAA        244
Gln Lys Asp Lys Gln Ser Tyr Arg Asp Leu Lys Glu Val Thr Pro Glu
        60                  65                  70

GGG CTC CAA ATG GTA AAG AAA AAC TTT GAG TGG GTT GCA GAG AGA GTA        292
Gly Leu Gln Met Val Lys Lys Asn Phe Glu Trp Val Ala Glu Arg Val
    75                  80                  85

GAG TTG CTT TTG AAA TCA GAA AGT CAG TGC AGG GTT GTA GTG TTG ATG        340
Glu Leu Leu Leu Lys Ser Glu Ser Gln Cys Arg Val Val Val Leu Met
90                  95                  100                 105

GGC TCT ACT TCT GAT CTT GGT CAC TGT GAA AAA ATC AAG AAG GCC TGT        388
Gly Ser Thr Ser Asp Leu Gly His Cys Glu Lys Ile Lys Lys Ala Cys
                110                 115                 120

GGA AAT TTT GGC ATT CCA TGT GAA CTT CGA GTA ACA TCT GCG CAT AAA        436
Gly Asn Phe Gly Ile Pro Cys Glu Leu Arg Val Thr Ser Ala His Lys
            125                 130                 135

GGA CCA GAT GAA ACT CTG AGG ATT AAA GCT GAG TAT GAA GGG GAT GGC        484
Gly Pro Asp Glu Thr Leu Arg Ile Lys Ala Glu Tyr Glu Gly Asp Gly
        140                 145                 150

ATT CCT ACT GTA TTT GTG GCA GTG GCA GGC AGA AGT AAT GGT TTG GGA        532
Ile Pro Thr Val Phe Val Ala Val Ala Gly Arg Ser Asn Gly Leu Gly
    155                 160                 165

CCA GTG ATG TCT GGG AAC ACT GCA TAT CCA GTT ATC AGC TGT CCT CCC        580
Pro Val Met Ser Gly Asn Thr Ala Tyr Pro Val Ile Ser Cys Pro Pro
170                 175                 180                 185

CTC ACA CCA GAC TGG GGA GTT CAG GAT GTG TGG TCT TCT CTT CGA CTA        628
Leu Thr Pro Asp Trp Gly Val Gln Asp Val Trp Ser Ser Leu Arg Leu
                190                 195                 200

CCC AGT GGT CTT GGC TGT TCA ACC GTA CTT TCT CCA GAA GGA TCA GCT        676
```

-continued

```
Pro Ser Gly Leu Gly Cys Ser Thr Val Leu Ser Pro Glu Gly Ser Ala
            205                 210                 215

CAA TTT GCT GCT CAG ATA TTT GGG TTA AGC AAC CAT TTG GTA TGG AGC       724
Gln Phe Ala Ala Gln Ile Phe Gly Leu Ser Asn His Leu Val Trp Ser
            220                 225                 230

AAA CTG CGA GCA AGC ATT TTG AAC ACA TGG ATT TCC TTG AAG CAG GCT       772
Lys Leu Arg Ala Ser Ile Leu Asn Thr Trp Ile Ser Leu Lys Gln Ala
            235                 240                 245

GAC AAG AAA ATC AGA GAA TGT AAT TTA TAAGAAAGAA TGCCATTGAA TTTTTTA     826
Asp Lys Lys Ile Arg Glu Cys Asn Leu
250                 255

GGGGAAAAAC TACAAATTTC TAATTTAGCT GAAGGAAAAT CAAGCAAGAT GAAAAGGTAA      886

TTTTAAATTA GAGAACACAA ATAAAATGTA TTAGTGAATA AATGGTGAGG GTAGGCCTAT      946

TCAGATGCAA GGCCAGCAAT GGGGCTCCCC ATTATCCCCA CCCCTTTGGT CCCAGTCCCC     1006

TTCTCTGCAA TGGGCACGCA TAGAGGAGAC ACAAAGGGTA TTAGACGCAA CATCATTGGC     1066

CCAGGGGAGT CCGAGAAGAG CTGCCATTGG CTGACAGGGC ATTTTCAGGC TCTGTCATTG     1126

GTCAGGGAGC ACACCCCAGC CTGAAGAGTG ATGCCATTGG CCAGGGAGTG GTTTTGTCAT     1186

AGCCGTTGGC TGTGAAGTGG AAGGAAAAGA TCTGGGAATG AAGCCCTGTG CCAGGAAGA      1246

TAGACAGGGC AGCAACTTCT GGGCCTCCAG GCCCTCTTCC CACCATAGCA ATGTGGGCAA     1306

AACTGGTGTC AGGCCCCAGC CAGAAAAGG AGCCCAAGCC AGAGGGCAAG TGACAAAGGA     1366

TGTACCATGT CCAATCTCCC ACACCCTGGG GCTGCCCTTC CAATGTCTT TCTTGATAGC     1426

CAAGTTGGGC TGGGAGCAGC TCACTGCTCC TCTAGCCAGG AGGGTTTCTC AGCTCCTGGA     1486

GGCCGCAGCT TGATGTTGAA CTGCTGCAGG GTCTGCTCCA GCTGTTTCTG GTTCCCAGCA     1546

AAGTAGGCGG ACACAGCATT GTGGAAGAGC AGCAGCTGCT TGTGCATCAC CTTGATCTTG     1606

TTTTCTTCCA GGAACTTGAG CTTGATGGCC ACATCTCCCC GCAGCTTCTC ATACTTGTCC     1666

CGATGGGCCT GGAAAGTGGC CTGGGCACTC TCAAGTCGAC CACGTGTCCC TGCATCCCGG     1726

GGGCCTAGAC TCAGCTCCTC TAAGTCTGTT CGGTAGGCAT CATATTCCAG CCTGGCAGCC     1786

TCATACTGTT TCACAGTCAT GAGCGTGTCT TCCATGGTCT TGGTGACCAA TGTGTTGATG     1846

CTAGAGACAA AGAAGTTCAC GGCTCCTAGC AGCGTTTCCC CATTCTTGCA TAGTAGTTTC     1906

TGTGTCTCTG CATTGTAGCC AAATTCCTCC TGAAGCTCTG GGGACTTCTG GCTGAGGTCA     1966

GCAAAGGCAT CACCCAGTGC ATGCTGGGTC TGCAGCAGGC TGTAGAGGTG GGCTGTCAGT     2026

GCCCGGCCCA GCTGCAGGAC ACTCTCATAC TTGCGCTTCG TCTCACGCAG CAACTCAATC     2086

TGCAGCTCTA GCTCCAGGAT TCCGGCGCCT CCACTCCGTC CCCCGCGGGT CTGCTCTGTG     2146

TGCCATGGAC GGCATTGTCC CAGATATAGC CGTTGGTACA AAGCGGGGAT CTGACGAGCT     2206

TTTCTCTACT TGTGTCACTA ACGGACCGTT TATCATGAGC AGCAACTCGG CTTCTGCAGC     2266

AAACGGAAAT GACAGCAAGA AGTTCAAAGG TGACAGCCGA AGTGCAGGCG TCCCCTCTAG     2326

AGTGATCCAC ATCCGGAAGC TCCCCATCGA CGTCACGGAG GGGAAGTCA TCTCCCTGGG     2386

GCTGCCCTTT GGAAGGTCA CCAACCTCCT GATGCTGAAG GGAAAAACC AGGCCTTCAT     2446

CGAGATGAAC ACGGAGGAGG CTGCCAATAC CATGGTGAAC TACTACACCT CGGTGACCCC     2506

TGTGCTGCGC GGCCAGCCCA TCTACATCCA GTTCTCCAAC CACAAGGAGC TGAAGACCGA     2566

CAGCTCTCCC AACCAGGCGC GGGCCCAGGC GGCCCTGCAG GCGGTGAACT CGGTCCAGTC     2626

GGGGAACCTG GCCTTGGCTG CCTCGGCGGC GGCCGTGGAT GCAGGGATGG CGATGGCCGG     2686

GCAGAGCCCC GTGCTCAGGA TCATCGTGGA GAACCTCTTC TACCCTGTGA CCCTGGATGT     2746
```

```
GCTGCACCAG ATTTTCTCCA AGTTCGGCAC AGTGTTGAAG ATCATCACCT TCACCAAGAA      2806

CAACCAGTTC CAGGCCCTGC TGCAGTATGC GGACCCCGTG AGCGCCCAGC ACGCCAAGCT      2866

GTCGCTGGAC GGGCAGAACA TCTACAACGC CTGCTGCACG CTGCGCATCG ACTTTTCCAA      2926

GCTCACCAGC CTCAACGTCA AGTACAACAA TGACAAGAGC CGTGACTACC TCGTGCCGAA      2986

TTCTTTGGAT CC                                                         2998
```

(2) INFORMATION FOR SEQ ID NO:150:

(i) SEQUENCE CHARACTERISTICS:
        (A) LENGTH: 258 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:150:

```
Ala Thr Gln Ala Ile Phe Glu Ile Leu Glu Lys Ser Trp Leu Pro Gln
  1               5                  10                  15

Asn Cys Thr Leu Val Asp Met Lys Ile Glu Phe Gly Val Asp Val Thr
                 20                  25                  30

Thr Lys Glu Ile Val Leu Ala Asp Val Ile Asp Asn Asp Ser Trp Arg
             35                  40                  45

Leu Trp Pro Ser Gly Asp Arg Ser Gln Gln Lys Asp Lys Gln Ser Tyr
 50                  55                  60

Arg Asp Leu Lys Glu Val Thr Pro Glu Gly Leu Gln Met Val Lys Lys
 65                  70                  75                  80

Asn Phe Glu Trp Val Ala Glu Arg Val Glu Leu Leu Lys Ser Glu
                 85                  90                  95

Ser Gln Cys Arg Val Val Leu Met Gly Ser Thr Ser Asp Leu Gly
                100                 105                 110

His Cys Glu Lys Ile Lys Lys Ala Cys Gly Asn Phe Gly Ile Pro Cys
                115                 120                 125

Glu Leu Arg Val Thr Ser Ala His Lys Gly Pro Asp Glu Thr Leu Arg
    130                 135                 140

Ile Lys Ala Glu Tyr Glu Gly Asp Gly Ile Pro Thr Val Phe Val Ala
145                 150                 155                 160

Val Ala Gly Arg Ser Asn Gly Leu Gly Pro Val Met Ser Gly Asn Thr
                165                 170                 175

Ala Tyr Pro Val Ile Ser Cys Pro Pro Leu Thr Pro Asp Trp Gly Val
                180                 185                 190

Gln Asp Val Trp Ser Ser Leu Arg Leu Pro Ser Gly Leu Gly Cys Ser
                195                 200                 205

Thr Val Leu Ser Pro Glu Gly Ser Ala Gln Phe Ala Ala Gln Ile Phe
    210                 215                 220

Gly Leu Ser Asn His Leu Val Trp Ser Lys Leu Arg Ala Ser Ile Leu
225                 230                 235                 240

Asn Thr Trp Ile Ser Leu Lys Gln Ala Asp Lys Lys Ile Arg Glu Cys
                245                 250                 255

Asn Leu
```

(2) INFORMATION FOR SEQ ID NO:151:

(i) SEQUENCE CHARACTERISTICS:

(A) LENGTH: 1038 amino acids
(B) TYPE: amino acid
(C) STRANDEDNESS: single
(D) TOPOLOGY: linear (xi) SEQUENCE DESCRIPTION: SEQ ID NO:151:

```
Ile Gln Arg Phe Gly Thr Ser Gly His Ile Met Asn Leu Gln Ala Gln
 1               5                  10                  15

Pro Lys Ala Gln Asn Lys Arg Lys Cys Leu Phe Gly Gly Gln Glu
            20                  25                  30

Pro Ala Pro Lys Glu Gln Pro Pro Leu Gln Pro Gln Gln Ser
        35                  40                  45

Ile Arg Val Lys Glu Glu Gln Tyr Leu Gly His Glu Gly Pro Gly Gly
50                  55                  60

Ala Val Ser Thr Ser Gln Pro Val Glu Leu Pro Pro Ser Ser Leu
65                  70                  75                  80

Ala Leu Leu Asn Ser Val Val Tyr Gly Pro Glu Arg Thr Ser Ala Ala
                85                  90                  95

Met Leu Ser Gln Gln Val Ala Ser Val Lys Trp Pro Asn Ser Val Met
                100                 105                 110

Ala Pro Gly Arg Gly Pro Glu Arg Gly Gly Gly Gly Val Ser Asp
            115                 120                 125

Ser Ser Trp Gln Gln Gln Pro Gly Gln Pro Pro His Ser Thr Trp
    130                 135                 140

Asn Cys His Ser Leu Ser Leu Tyr Ser Ala Thr Lys Gly Ser Pro His
145                 150                 155                 160

Pro Gly Val Gly Val Pro Thr Tyr Tyr Asn His Pro Glu Ala Leu Lys
                165                 170                 175

Arg Glu Lys Ala Gly Gly Pro Gln Leu Asp Arg Tyr Val Arg Pro Met
                180                 185                 190

Met Pro Gln Lys Val Gln Leu Glu Val Gly Arg Pro Gln Ala Pro Leu
            195                 200                 205

Asn Ser Phe His Ala Ala Lys Lys Pro Pro Asn Gln Ser Leu Pro Leu
            210                 215                 220

Gln Pro Phe Gln Leu Ala Phe Gly His Gln Val Asn Arg Gln Val Phe
225                 230                 235                 240

Arg Gln Gly Pro Pro Pro Asn Pro Val Ala Ala Phe Pro Pro Gln
                245                 250                 255

Lys Gln Gln Gln Gln Gln Pro Gln Gln Gln Gln Gln Gln Gln
            260                 265                 270

Ala Ala Leu Pro Gln Met Pro Leu Phe Glu Asn Phe Tyr Ser Met Pro
            275                 280                 285

Gln Gln Pro Ser Gln Gln Pro Gln Asp Phe Gly Leu Gln Pro Ala Gly
            290                 295                 300

Pro Leu Gly Gln Ser His Leu Ala His His Ser Met Ala Pro Tyr Pro
305                 310                 315                 320

Phe Pro Pro Asn Pro Asp Met Asn Pro Glu Leu Arg Lys Ala Leu Leu
                325                 330                 335

Gln Asp Ser Ala Pro Gln Pro Ala Leu Pro Gln Val Gln Ile Pro Phe
            340                 345                 350

Pro Arg Arg Ser Arg Arg Leu Ser Lys Glu Gly Ile Leu Pro Pro Ser
            355                 360                 365

Ala Leu Asp Gly Ala Gly Thr Gln Pro Gly Gln Glu Ala Thr Gly Asn
            370                 375                 380
```

```
Leu Phe Leu His His Trp Pro Leu Gln Gln Pro Pro Gly Ser Leu
385                 390                 395                 400

Gly Gln Pro His Pro Glu Ala Leu Gly Phe Pro Leu Glu Leu Arg Glu
            405                 410                 415

Ser Gln Leu Leu Pro Asp Gly Glu Arg Leu Ala Pro Asn Gly Arg Glu
            420                 425                 430

Arg Glu Ala Pro Ala Met Gly Ser Glu Glu Gly Met Arg Ala Val Ser
            435                 440                 445

Thr Gly Asp Cys Gly Gln Val Leu Arg Gly Gly Val Ile Gln Ser Thr
            450                 455                 460

Arg Arg Arg Arg Arg Ala Ser Gln Glu Ala Asn Leu Leu Thr Leu Ala
465                 470                 475                 480

Gln Lys Ala Val Glu Leu Ala Ser Leu Gln Asn Ala Lys Asp Gly Ser
            485                 490                 495

Gly Ser Glu Glu Lys Arg Lys Ser Val Leu Ala Ser Thr Thr Lys Cys
            500                 505                 510

Gly Val Glu Phe Ser Glu Pro Ser Leu Ala Thr Lys Arg Ala Arg Glu
            515                 520                 525

Asp Ser Gly Met Val Pro Leu Ile Ile Pro Val Ser Val Pro Val Arg
530                 535                 540

Thr Val Asp Pro Thr Glu Ala Ala Gln Ala Gly Gly Leu Asp Glu Asp
545                 550                 555                 560

Gly Lys Gly Leu Glu Gln Asn Pro Ala Glu His Lys Pro Ser Val Ile
            565                 570                 575

Val Thr Arg Arg Arg Ser Thr Arg Ile Pro Gly Thr Asp Ala Gln Ala
            580                 585                 590

Gln Ala Glu Asp Met Asn Val Lys Leu Glu Gly Glu Pro Ser Val Arg
            595                 600                 605

Lys Pro Lys Gln Arg Pro Arg Pro Glu Pro Leu Ile Ile Pro Thr Lys
            610                 615                 620

Ala Gly Thr Phe Ile Ala Pro Pro Val Tyr Ser Asn Ile Thr Pro Tyr
625                 630                 635                 640

Gln Ser His Leu Arg Ser Pro Val Arg Leu Ala Asp His Pro Ser Glu
            645                 650                 655

Arg Ser Phe Glu Leu Pro Pro Tyr Thr Pro Pro Ile Leu Ser Pro
            660                 665                 670

Val Arg Glu Gly Ser Gly Leu Tyr Phe Asn Ala Ile Ile Ser Thr Ser
            675                 680                 685

Thr Ile Pro Ala Pro Pro Ile Thr Pro Lys Ser Ala His Arg Thr
690                 695                 700

Leu Leu Arg Thr Asn Ser Ala Glu Val Thr Pro Val Leu Ser Val
705                 710                 715                 720

Met Gly Glu Ala Thr Pro Val Ser Ile Glu Pro Arg Ile Asn Val Gly
            725                 730                 735

Ser Arg Phe Gln Ala Glu Ile Pro Leu Met Arg Asp Arg Ala Leu Ala
            740                 745                 750

Ala Ala Asp Pro His Lys Ala Asp Leu Val Trp Gln Pro Trp Glu Asp
            755                 760                 765

Leu Glu Ser Ser Arg Glu Lys Gln Arg Gln Val Glu Asp Leu Leu Thr
            770                 775                 780

Ala Ala Cys Ser Ser Ile Phe Pro Gly Ala Gly Thr Asn Gln Glu Leu
785                 790                 795                 800

Ala Leu His Cys Leu His Glu Ser Arg Gly Asp Ile Leu Glu Thr Leu
```

-continued

```
                805                 810                 815
Asn Lys Leu Leu Leu Lys Lys Pro Leu Arg Pro His Asn His Pro Leu
                820                 825                 830
Ala Thr Tyr His Tyr Thr Gly Ser Asp Gln Trp Lys Met Ala Glu Arg
                835                 840                 845
Lys Leu Phe Asn Lys Gly Ile Ala Ile Tyr Lys Lys Asp Phe Phe Leu
                850                 855                 860
Val Gln Lys Leu Ile Gln Thr Lys Thr Val Ala Gln Cys Val Glu Phe
865                 870                 875                 880
Tyr Tyr Thr Tyr Lys Lys Gln Val Lys Ile Gly Arg Asn Gly Thr Leu
                885                 890                 895
Thr Phe Gly Asp Val Asp Thr Ser Asp Glu Lys Ser Ala Gln Glu Glu
                900                 905                 910
Val Glu Val Asp Ile Lys Thr Ser Gln Lys Phe Pro Arg Val Pro Leu
                915                 920                 925
Pro Arg Arg Glu Ser Pro Ser Glu Glu Arg Leu Glu Pro Lys Arg Glu
                930                 935                 940
Val Lys Glu Pro Arg Lys Glu Gly Glu Glu Val Pro Glu Ile Gln
945                 950                 955                 960
Glu Lys Glu Glu Gln Glu Glu Gly Arg Glu Arg Ser Arg Arg Ala Ala
                965                 970                 975
Ala Val Lys Ala Thr Gln Thr Leu Gln Ala Asn Glu Ser Ala Ser Asp
                980                 985                 990
Ile Leu Ile Leu Arg Ser His Glu Ser Asn Ala Pro Gly Ser Ala Gly
                995                 1000                1005
Gly Gln Ala Ser Glu Lys Pro Arg Glu Gly Thr Gly Lys Ser Arg Arg
                1010                1015                1020
Ala Leu Pro Phe Ser Glu Lys Lys Lys Lys Gln Lys Ala
1025                1030                1035
```

(2) INFORMATION FOR SEQ ID NO:152:

(i) SEQUENCE CHARACTERISTICS:
        (A) LENGTH: 849 amino acids
        (B) TYPE: amino acid
        (C) STRANDEDNESS: single
        (D) TOPOLOGY: linear (xi) SEQUENCE DESCRIPTION: SEQ ID NO:152:

```
Ile Arg His Glu Val Ser Phe Leu Trp Asn Thr Glu Ala Ala Cys Pro
1               5                   10                  15
Ile Gln Thr Thr Thr Asp Thr Asp Gln Ala Cys Ser Ile Arg Asp Pro
                20                  25                  30
Asn Ser Gly Phe Val Phe Asn Leu Asn Pro Leu Asn Ser Ser Gln Gly
                35                  40                  45
Tyr Asn Val Ser Gly Ile Gly Lys Ile Phe Met Phe Asn Val Cys Gly
50                  55                  60
Thr Met Pro Val Cys Gly Thr Ile Leu Gly Lys Pro Ala Ser Gly Cys
65                  70                  75                  80
Glu Ala Glu Thr Gln Thr Glu Glu Leu Lys Asn Trp Lys Pro Ala Arg
                85                  90                  95
Pro Val Gly Ile Glu Lys Ser Leu Gln Leu Ser Thr Glu Gly Phe Ile
                100                 105                 110
Thr Leu Thr Tyr Lys Gly Pro Leu Ser Ala Lys Gly Thr Ala Asp Ala
                115                 120                 125
```

-continued

```
Phe Ile Val Arg Phe Val Cys Asn Asp Asp Val Tyr Ser Gly Pro Leu
    130                 135                 140

Lys Phe Leu His Gln Asp Ile Asp Ser Gly Gln Gly Ile Arg Asn Thr
145                 150                 155                 160

Tyr Phe Glu Phe Glu Thr Ala Leu Ala Cys Val Pro Ser Pro Val Asp
                165                 170                 175

Cys Gln Val Thr Asp Leu Ala Gly Asn Glu Tyr Asp Leu Thr Gly Leu
                180                 185                 190

Ser Thr Val Arg Lys Pro Trp Thr Ala Val Asp Thr Ser Val Asp Gly
        195                 200                 205

Arg Lys Arg Thr Phe Tyr Leu Ser Val Cys Asn Pro Leu Pro Tyr Ile
    210                 215                 220

Pro Gly Cys Gln Gly Ser Ala Val Gly Ser Cys Leu Val Ser Glu Gly
225                 230                 235                 240

Asn Ser Trp Asn Leu Gly Val Val Gln Met Ser Pro Gln Ala Ala Ala
                245                 250                 255

Asn Gly Ser Leu Ser Ile Met Tyr Val Asn Gly Asp Lys Cys Gly Asn
                260                 265                 270

Gln Arg Phe Ser Thr Arg Ile Thr Phe Glu Cys Ala Gln Ile Ser Gly
        275                 280                 285

Ser Pro Ala Phe Gln Leu Gln Asp Gly Cys Glu Tyr Val Phe Ile Trp
    290                 295                 300

Arg Thr Val Glu Ala Cys Pro Val Arg Val Glu Gly Asp Asn Cys
305                 310                 315                 320

Glu Val Lys Asp Pro Arg His Gly Asn Leu Tyr Asp Leu Lys Pro Leu
                325                 330                 335

Gly Leu Asn Asp Thr Ile Val Ser Ala Gly Glu Tyr Thr Tyr Tyr Phe
                340                 345                 350

Arg Val Cys Gly Lys Leu Ser Ser Asp Val Cys Pro Thr Ser Asp Lys
        355                 360                 365

Ser Lys Val Val Ser Ser Cys Gln Glu Lys Arg Glu Pro Gln Gly Phe
    370                 375                 380

His Lys Val Ala Gly Leu Leu Thr Gln Lys Leu Thr Tyr Glu Asn Gly
385                 390                 395                 400

Leu Leu Lys Met Asn Phe Thr Gly Gly Asp Thr Cys His Lys Val Tyr
                405                 410                 415

Gln Arg Ser Thr Ala Ile Phe Phe Tyr Cys Asp Arg Gly Thr Gln Arg
                420                 425                 430

Pro Val Phe Leu Lys Glu Thr Ser Asp Cys Ser Tyr Leu Phe Glu Trp
        435                 440                 445

Arg Thr Gln Tyr Ala Cys Pro Pro Phe Asp Leu Thr Glu Cys Ser Phe
    450                 455                 460

Lys Asp Gly Ala Gly Asn Ser Phe Asp Leu Ser Ser Leu Ser Arg Tyr
465                 470                 475                 480

Ser Asp Asn Trp Glu Ala Ile Thr Gly Thr Gly Asp Pro Glu His Tyr
                485                 490                 495

Leu Ile Asn Val Cys Lys Ser Leu Ala Pro Gln Ala Gly Thr Glu Pro
                500                 505                 510

Cys Pro Pro Glu Ala Ala Ala Cys Leu Leu Gly Gly Ser Lys Pro Val
        515                 520                 525

Asn Leu Gly Arg Val Arg Asp Gly Pro Gln Trp Arg Asp Gly Ile Ile
    530                 535                 540

Val Leu Lys Tyr Val Asp Gly Asp Leu Cys Pro Asp Gly Ile Arg Lys
```

```
                545                 550                 555                 560
Lys Ser Thr Thr Ile Arg Phe Thr Cys Ser Glu Ser Gln Val Asn Ser
                    565                 570                 575

Arg Pro Met Phe Ile Ser Ala Val Glu Asp Cys Glu Tyr Thr Phe Ala
                580                 585                 590

Trp Pro Thr Ala Thr Ala Cys Pro Met Lys Ser Asn Glu His Asp Asp
                595                 600                 605

Cys Gln Val Thr Asn Pro Ser Thr Gly His Leu Phe Asp Leu Ser Ser
                610                 615                 620

Leu Ser Gly Arg Ala Gly Phe Thr Ala Ala Tyr Ser Glu Lys Gly Leu
625                 630                 635                 640

Val Tyr Met Ser Ile Cys Gly Glu Asn Glu Asn Cys Pro Pro Gly Val
                    645                 650                 655

Gly Ala Cys Phe Gly Gln Thr Arg Ile Ser Val Gly Lys Ala Asn Lys
                    660                 665                 670

Arg Leu Arg Tyr Val Asp Gln Val Leu Gln Leu Val Tyr Lys Asp Gly
                    675                 680                 685

Ser Pro Cys Pro Ser Lys Ser Gly Leu Ser Tyr Lys Ser Val Ile Ser
                690                 695                 700

Phe Val Cys Arg Pro Glu Ala Gly Pro Thr Asn Arg Pro Met Leu Ile
705                 710                 715                 720

Ser Leu Asp Lys Gln Thr Cys Thr Leu Phe Phe Ser Trp His Thr Pro
                    725                 730                 735

Leu Ala Cys Glu Gln Ala Thr Glu Cys Ser Val Arg Asn Gly Ser Ser
                    740                 745                 750

Ile Val Asp Leu Ser Pro Leu Ile His Arg Thr Gly Gly Tyr Glu Ala
                    755                 760                 765

Tyr Asp Glu Ser Glu Asp Asp Ala Ser Asp Thr Asn Pro Asp Phe Tyr
                770                 775                 780

Ile Asn Ile Cys Gln Pro Leu Asn Pro Met His Gly Val Pro Cys Pro
785                 790                 795                 800

Ala Gly Ala Ala Val Cys Lys Val Pro Ile Asp Gly Pro Pro Ile Asp
                    805                 810                 815

Ile Gly Arg Val Ala Gly Pro Pro Ile Leu Asn Pro Ile Ala Asn Glu
                    820                 825                 830

Ile Tyr Leu Asn Phe Glu Ser Ser Thr Pro Cys Gln Glu Phe Ser Cys
                    835                 840                 845

Lys (2) INFORMATION FOR SEQ ID NO:153:

(i) SEQUENCE CHARACTERISTICS:
        (A) LENGTH: 852 amino acids
        (B) TYPE: amino acid
        (C) STRANDEDNESS: single
        (D) TOPOLOGY: linear (xi) SEQUENCE DESCRIPTION: SEQ ID NO:153:

Met Ala Arg Leu Ser Arg Pro Glu Arg Pro Asp Leu Val Phe Glu Glu
1               5                   10                  15

Glu Asp Leu Pro Tyr Glu Glu Glu Ile Met Arg Asn Gln Phe Ser Val
                20                  25                  30

Lys Cys Trp Leu His Tyr Ile Glu Phe Lys Gln Gly Ala Pro Lys Pro
                35                  40                  45

Arg Leu Asn Gln Leu Tyr Glu Arg Ala Leu Lys Leu Leu Pro Cys Ser
```

-continued

```
                50                    55                    60
Tyr Lys Leu Trp Tyr Arg Tyr Leu Lys Ala Arg Arg Ala Gln Val Lys
 65                  70                  75                  80
His Arg Cys Val Thr Asp Pro Ala Tyr Glu Asp Val Asn Asn Cys His
                85                  90                  95
Glu Arg Ala Phe Val Phe Met His Lys Met Pro Arg Leu Trp Leu Asp
                100                 105                 110
Tyr Cys Gln Phe Leu Met Asp Gln Gly Arg Val Thr His Thr Arg Arg
                115                 120                 125
Thr Phe Asp Arg Ala Leu Arg Ala Leu Pro Ile Thr Gln His Ser Arg
130                 135                 140
Ile Trp Pro Leu Tyr Leu Arg Phe Leu Arg Ser His Pro Leu Pro Glu
145                 150                 155                 160
Thr Ala Val Arg Gly Tyr Arg Arg Phe Leu Lys Leu Ser Pro Glu Ser
                165                 170                 175
Ala Glu Glu Tyr Ile Glu Tyr Leu Lys Ser Ser Asp Arg Leu Asp Glu
                180                 185                 190
Ala Ala Gln Arg Leu Ala Thr Val Val Asn Asp Glu Arg Phe Val Ser
                195                 200                 205
Lys Ala Gly Lys Ser Asn Tyr Gln Leu Trp His Glu Leu Cys Asp Leu
210                 215                 220
Ile Ser Gln Asn Pro Asp Lys Val Gln Ser Leu Asn Val Asp Ala Ile
225                 230                 235                 240
Ile Arg Gly Gly Leu Thr Arg Phe Thr Asp Gln Leu Gly Lys Leu Trp
                245                 250                 255
Cys Ser Leu Ala Asp Tyr Tyr Ile Arg Ser Gly His Phe Glu Lys Ala
                260                 265                 270
Arg Asp Val Tyr Glu Glu Ala Ile Arg Thr Val Met Thr Val Arg Asp
                275                 280                 285
Phe Thr Gln Val Phe Asp Ser Tyr Ala Gln Phe Glu Glu Ser Met Ile
                290                 295                 300
Ala Ala Lys Met Glu Thr Ala Ser Glu Leu Gly Arg Glu Glu Glu Asp
305                 310                 315                 320
Asp Val Asp Leu Glu Leu Arg Leu Ala Arg Phe Glu Gln Leu Ile Ser
                325                 330                 335
Arg Arg Pro Leu Leu Leu Asn Ser Val Leu Leu Arg Gln Asn Pro His
                340                 345                 350
His Val His Glu Trp His Lys Arg Val Ala Leu His Gln Gly Arg Pro
                355                 360                 365
Arg Glu Ile Ile Asn Thr Tyr Thr Glu Ala Val Gln Thr Val Asp Pro
                370                 375                 380
Phe Lys Ala Thr Gly Lys Pro His Thr Leu Trp Val Ala Phe Ala Lys
385                 390                 395                 400
Phe Tyr Glu Asp Asn Gly Gln Leu Asp Asp Ala Arg Val Ile Leu Glu
                405                 410                 415
Lys Ala Thr Lys Val Asn Phe Lys Gln Val Asp Asp Leu Ala Ser Val
                420                 425                 430
Trp Cys Gln Cys Gly Glu Leu Glu Leu Arg His Glu Asn Tyr Asp Glu
                435                 440                 445
Ala Leu Arg Leu Leu Arg Lys Ala Thr Ala Leu Pro Ala Arg Arg Ala
                450                 455                 460
Glu Tyr Phe Asp Gly Ser Glu Pro Val Gln Asn Arg Val Tyr Lys Ser
465                 470                 475                 480
```

-continued

```
Leu Lys Val Trp Ser Met Leu Ala Asp Leu Glu Glu Ser Leu Gly Thr
                485                 490                 495
Phe Gln Ser Thr Lys Ala Val Tyr Asp Arg Ile Leu Asp Leu Arg Ile
            500                 505                 510
Ala Thr Pro Gln Ile Val Ile Asn Tyr Ala Met Phe Leu Glu Glu His
        515                 520                 525
Lys Tyr Phe Glu Glu Ser Phe Lys Ala Tyr Glu Arg Gly Ile Ser Leu
    530                 535                 540
Phe Lys Trp Pro Asn Val Ser Asp Ile Trp Ser Thr Tyr Leu Thr Lys
545                 550                 555                 560
Phe Ile Ala Arg Tyr Gly Gly Arg Lys Leu Glu Arg Ala Arg Asp Leu
                565                 570                 575
Phe Glu Gln Ala Leu Asp Gly Cys Pro Pro Lys Tyr Ala Lys Thr Leu
            580                 585                 590
Tyr Leu Leu Tyr Ala Gln Leu Glu Glu Trp Gly Leu Ala Arg His
        595                 600                 605
Ala Met Ala Val Tyr Glu Arg Ala Thr Arg Ala Val Glu Pro Ala Gln
    610                 615                 620
Gln Tyr Asp Met Phe Asn Ile Tyr Ile Lys Arg Ala Ala Glu Ile Tyr
625                 630                 635                 640
Gly Val Thr His Thr Arg Gly Ile Tyr Gln Lys Ala Ile Glu Val Leu
                645                 650                 655
Ser Asp Glu His Ala Arg Glu Met Cys Leu Arg Phe Ala Asp Met Glu
            660                 665                 670
Cys Lys Leu Gly Glu Ile Asp Arg Ala Arg Ala Ile Tyr Ser Phe Cys
        675                 680                 685
Ser Gln Ile Cys Asp Pro Arg Thr Thr Gly Ala Phe Trp Gln Thr Trp
    690                 695                 700
Lys Asp Phe Glu Val Arg His Gly Asn Glu Asp Thr Ile Lys Glu Met
705                 710                 715                 720
Leu Arg Ile Arg Arg Ser Val Gln Ala Thr Tyr Asn Thr Gln Val Asn
                725                 730                 735
Phe Met Ala Ser Gln Met Leu Lys Val Ser Gly Ser Ala Thr Gly Thr
            740                 745                 750
Val Ser Asp Leu Ala Pro Gly Gln Ser Gly Met Asp Asp Met Lys Leu
        755                 760                 765
Leu Glu Gln Arg Ala Glu Gln Leu Ala Ala Glu Ala Glu Arg Asp Gln
    770                 775                 780
Pro Leu Arg Ala Gln Ser Lys Ile Leu Phe Val Arg Ser Asp Ala Ser
785                 790                 795                 800
Arg Glu Glu Leu Ala Glu Leu Ala Gln Gln Val Asn Pro Glu Glu Ile
                805                 810                 815
Gln Leu Gly Glu Asp Glu Asp Glu Asp Met Asp Leu Glu Pro Asn
            820                 825                 830
Glu Val Arg Leu Glu Gln Gln Ser Val Pro Ala Ala Val Phe Gly Ser
        835                 840                 845
Leu Lys Glu Asp
    850
```

(2) INFORMATION FOR SEQ ID NO:154:

(i) SEQUENCE CHARACTERISTICS:
        (A) LENGTH: 693 amino acids
        (B) TYPE: amino acid

```
        (C) STRANDEDNESS: single
        (D) TOPOLOGY: linear (xi) SEQUENCE DESCRIPTION: SEQ ID NO:154:

Met Phe Ser Ala Leu Lys Lys Leu Val Gly Ser Asp Gln Ala Pro Gly
 1               5                  10                  15

Arg Asp Lys Asn Ile Pro Ala Gly Leu Gln Ser Met Asn Gln Ala Leu
             20                  25                  30

Gln Arg Arg Phe Ala Lys Gly Val Gln Tyr Asn Met Lys Ile Val Ile
         35                  40                  45

Arg Gly Asp Arg Asn Thr Gly Lys Thr Ala Leu Trp His Arg Leu Gln
     50                  55                  60

Gly Arg Pro Phe Val Glu Glu Tyr Ile Pro Thr Gln Glu Ile Gln Val
 65                  70                  75                  80

Thr Ser Ile His Trp Ser Tyr Lys Thr Thr Asp Ile Val Lys Val
                 85                  90                  95

Glu Val Trp Asp Val Val Asp Lys Gly Lys Cys Lys Lys Arg Gly Asp
                100                 105                 110

Gly Leu Lys Met Glu Asn Asp Pro Gln Glu Xaa Glu Ser Glu Met Ala
             115                 120                 125

Leu Asp Ala Glu Phe Leu Asp Val Tyr Lys Asn Cys Asn Gly Val Val
         130                 135                 140

Met Met Phe Asp Ile Thr Lys Gln Trp Thr Phe Asn Tyr Ile Leu Arg
145                 150                 155                 160

Glu Leu Pro Lys Val Pro Thr His Val Pro Val Cys Val Leu Gly Asn
                165                 170                 175

Tyr Arg Asp Met Gly Glu His Arg Val Ile Leu Pro Asp Asp Val Arg
             180                 185                 190

Asp Phe Ile Asp Asn Leu Asp Arg Pro Pro Gly Ser Ser Tyr Phe Arg
         195                 200                 205

Tyr Ala Glu Ser Ser Met Lys Asn Ser Phe Gly Leu Lys Tyr Leu His
     210                 215                 220

Lys Phe Phe Asn Ile Pro Phe Leu Gln Leu Gln Arg Glu Thr Leu Leu
225                 230                 235                 240

Arg Gln Leu Glu Thr Asn Gln Leu Asp Met Asp Ala Thr Leu Glu Glu
                245                 250                 255

Leu Ser Val Gln Gln Glu Thr Glu Asp Gln Asn Tyr Gly Ile Phe Leu
             260                 265                 270

Glu Met Met Glu Ala Arg Ser Arg Gly His Ala Ser Pro Leu Ala Ala
         275                 280                 285

Asn Gly Gln Ser Pro Ser Pro Gly Ser Gln Ser Pro Val Leu Pro Ala
     290                 295                 300

Pro Ala Val Ser Thr Gly Ser Ser Ser Pro Gly Thr Pro Gln Pro Ala
305                 310                 315                 320

Pro Gln Leu Pro Leu Asn Ala Ala Pro Ser Ser Val Pro Pro Val
                325                 330                 335

Pro Pro Ser Glu Ala Leu Pro Pro Ala Cys Pro Ser Ala Pro Ala
             340                 345                 350

Pro Arg Arg Ser Ile Ile Ser Arg Leu Phe Gly Thr Ser Pro Ala Thr
         355                 360                 365

Glu Ala Ala Pro Pro Pro Glu Pro Val Pro Ala Ala Gln Gly Pro
     370                 375                 380

Ala Thr Val Gln Ser Val Glu Asp Phe Val Pro Asp Asp Arg Leu Asp
385                 390                 395                 400
```

-continued

```
Arg Ser Phe Leu Glu Asp Thr Thr Pro Ala Arg Asp Glu Lys Lys Val
            405                 410                 415
Gly Ala Lys Ala Ala Gln Gln Asp Ser Asp Ser Asp Gly Glu Ala Leu
            420                 425                 430
Gly Gly Asn Pro Met Val Ala Gly Phe Gln Asp Asp Val Asp Leu Glu
            435                 440                 445
Asp Gln Pro Arg Gly Ser Pro Pro Leu Pro Ala Gly Pro Val Pro Ser
        450             455                 460
Gln Asp Ile Thr Leu Ser Ser Glu Glu Glu Ala Glu Val Ala Ala Pro
465             470                 475                 480
Thr Lys Gly Pro Ala Pro Ala Pro Gln Gln Cys Ser Glu Pro Glu Thr
            485                 490                 495
Lys Trp Ser Ser Ile Pro Ala Ser Lys Pro Arg Arg Gly Thr Ala Pro
            500                 505                 510
Thr Arg Thr Ala Ala Pro Pro Trp Pro Gly Gly Val Ser Val Arg Thr
            515                 520                 525
Gly Pro Glu Lys Arg Ser Ser Thr Arg Pro Pro Ala Glu Met Glu Pro
    530                 535                 540
Gly Lys Gly Glu Gln Ala Ser Ser Ser Glu Ser Asp Pro Glu Gly Pro
545                 550                 555                 560
Ile Ala Ala Gln Met Leu Ser Phe Val Met Asp Asp Pro Asp Phe Glu
                565                 570                 575
Ser Glu Gly Ser Asp Thr Gln Arg Arg Ala Asp Asp Phe Pro Val Arg
            580                 585                 590
Asp Asp Pro Ser Asp Val Thr Asp Glu Asp Glu Gly Pro Ala Glu Pro
        595                 600                 605
Pro Pro Pro Pro Lys Leu Pro Leu Pro Ala Phe Arg Leu Lys Asn Asp
    610                 615                 620
Ser Asp Leu Phe Gly Leu Gly Leu Glu Glu Ala Gly Pro Lys Glu Ser
625                 630                 635                 640
Ser Glu Glu Gly Lys Glu Gly Lys Thr Pro Ser Lys Glu Lys Lys Lys
                645                 650                 655
Lys Thr Lys Ser Phe Ser Arg Val Leu Leu Glu Arg Pro Arg Ala His
                660                 665                 670
Arg Phe Ser Thr Arg Val Gly Tyr Gln Val Ser Val Pro Asn Ser Pro
            675                 680                 685
Tyr Ser Glu Ser Tyr
            690
```

TUMOR NECROSIS FACTOR RECEPTOR RELEASING ENZYME

CROSS-REFERENCE TO RELATED APPLICATIONS

This application is a continuation-in-part of patent application Ser. No. 08/964,747, filed Nov. 5, 1997, which is a continuation-in-part of Provisional Patent Application No. 60/030,761, filed Nov. 6, 1996.

FIELD OF THE INVENTION

This invention relates to the purification and characterization of factors that substantially alter tumor necrosis factor (TNF) receptor (TNF-R) releasing enzyme (TRRE) activity, and methods of use thereof. Modulation of TRRE levels indirectly modulates effective levels of TNF. The invention further relates to methods of treatment of pathological conditions caused or exacerbated by altered levels or activity of TNF such as inflammatory conditions including autoimmune diseases, infections, septic shock, obesity, cachexia, and conditions that are associated with decreased effective levels or activity of TNF such as cancer.

BACKGROUND OF THE INVENTION

Tumor necrosis factor (TNF or TNF-α) and lymphotoxin (LT or TNF-β) are related cytokines that share 40 percent amino acid (AA) sequence homology. Old (1987) *Nature* 330:602–603. These cytokines are released mainly by macrophages, monocytes and natural killer (NK) cells in response to broad immune reactions. Gorton and Galli (1990) *Nature* 346:274–276; and Dubravec et al. (1990) *Proc. Natl. Acad. Sci. USA* 87:6758–6761. Although initially discovered as agents inducing hemorrhagic necrosis of tumors, these cytokines have been shown to have essential roles in both the inductive and effector phases of immune reactions and inflammation. The two cytokines cause a broad spectrum of effects on cells in vitro and tissues in vivo, including: (i) vascular thrombosis and tumor necrosis; (ii) inflammation; (iii) activation of macrophages and neutrophils; (iv) leukocytosis; (v) apoptosis; and (vi) shock. Beretz et al. (1990) *Biorheology* 27:455–460; Driscoll (1994) *Exp. Lung Res.* 20:473–490; Ferrante (1992) *Immunol. Ser.* 57:417–436; Golstein et al. (1991) *Immunol. Rev.* 121:29–65; and van der Poll and Lowry (1995) *Shock* 3:1–12. For a review of the mechanism of action of TNF, see Massague (1996) *Cell* 85:947–950. TNF has been associated with a variety of disease states including various forms of cancer, arthritis, psoriasis, endotoxic shock, sepsis, autoimmune diseases, infections, obesity, and cachexia. Attempts have been made to alter the course of a disease by treating the patient with TNF inhibitors. These attempts have met with varying degrees of success. For example, oxpentifylline did not alter the course of Crohn's disease, a chronic inflammatory bowel disease. Bauditz et al. (1997) *Gut* 40:470–4. However, the TNF inhibitor dexanabinol provided protection against TNF following traumatic brain injury. Shohami et al. (1997) *J. Neuroimmun.* 72:169–77.

Cachexia is pathological weight loss generally associated with anorexia, weakness, anemia, asthenia, and loss of body lipid stores and skeletal muscle protein. This state often accompanies burns, trauma, infection, and neoplastic diseases. Lawson et al. (1982) *Annu. Rev. Nutr.* 2:277–301; Argiles et al. (1988) *Mol. Cell. Biochem.* 81:3–17; and Ogiwara et al. (1994) *J. Surg. Oncol.* 57:129–133. TNF concentrations are elevated in many patients with cachexia. Scuderi et al. (1986) *Lancet* 2:1364–65; Grau et al. (1987) *Science* 237:1210–1212; and Waage et al. (1986) *Scand. J Immunol.* 24:739–743. TNF inhibits collagen αI gene expression and wound healing in a murine model of cachexia. Buck et al. (1996) *Am. J. Pathol.* 149:195–204. In septicemia (the invasion of bacteria into the bloodstream), increased endotoxin concentrations may raise TNF levels, causing cachexia. Beutler et al. (1985) *Science* 229:869–871; Tracey et al. (1987) *Nature* 330:662–664; and Michie et al. (1988) *New Engl. J. Med* 318:1481–1486. During cachexia, the loss of white adipose tissue is caused by the decreased activity of lipoprotein lipase (LPL); TNF lowers the activity of this enzyme. Price et al. (1986) *Arch. Biochem. Biophys.* 251:738–746; Cornelius et al. (1988) *Biochem. J.* 249:765–769; Fried et al. (1989) *J. Lipid. Res.* 30:1917–1923; Semb et al. (1987) *J. Biol. Chem.* 262:8390–8394; and Evans et al. (1988) *Biochem. J.* 256:1055–1058. Fat tissue loss is also associated with an increase in lipase activity and inhibition of glucose transport; TNF is also linked to both of these changes. Kawakami et al. (1987) *J. Biochem.* 331–338; Feingold et al. (1992) *Endocrinology* 130:10–16; and Hauner et al. (1995) *Diabetologia* 38:764–771. TNF mediates hypertriglyceridaemia associated with cachexia. Dessi et al. (1995) *Br. J Cancer* 72:1138–43. TNF also participates in the protein wasting, loss of skeletal muscle and loss of nitrogen associated with cachexia. Costelli et al. (1993) *J. Clin. Invest.* 92:2783–2789; Flores et al. (1989) *J. Clin. Invest.* 83:1614–1622; Goodman (1991) *Am. J. Physiol.* 260:E727–730; Zamir et al. (1992) *Arch. Surg.* 127:170–174; Llovera et al. (1993) *J. Natl. Cancer Inst. USA* 85:1334–1339; and Garcia-Martinez et al. (1993) *FEBS Lett.* 323:211–214.

Cachexia is also associated with TNF expression in cancer patients. TNF is linked to the three factors contributing to body weight control: intake, expenditure, and storage of energy. Administration of either TNF or IL-1, for example, induces a decrease in food intake. Rothwell (1993) *Int. J. Obesity* 17:S98-S101; Arbos et al. (1992) *Mol. Cell. Biochem.* 1 12:53–59; Fargeas et al. (1993) *Gastroenterology* 104:377–383; Plata-Salaman et al. (1994) *Am. J. Physiol.* 266:R1711–1715; Schwartz et al. (1995) *Am. J. Physiol.* 269:R949–957; and Oliff et al. (1987) *Cell* 50:555–563. Interestingly, TNF may have key roles in both extremes of weight problems. Abnormalities in its activity may lead to obesity; changes in its production result in the opposite effect, cachexia. Argilés et al. (1997) *FASEB J.* 11:743–751.

TNF has additional, related roles. It is involved in thermogenesis, particularly nonshivering thermogenesis in brown adipose tissue (BAT), a tissue with an elevated level in cachexia. Nicholls (1983) *Biosci. Rep.* 3:431–441; Rothwell (1993) *Int. J. Obesity* 17:S98–S101; Bianchi et al. (1989) *Horm. Metab. Res.* 21:1 1; and Oudart et al. (1995) *Can. J. Physiol. Pharmacol.* 73:1625–1631. TNF has also been implicated in non-insulin-dependent (type II) diabetes. Hotamisligil et al. (1995) *J. Clin. Invest.* 95:2409–2415; Arner (1996) *Diabetes Metab.* 13:S85–S86; Spiegelman et al. (1993) *Cell* 73:625–627; Saghizadeh et al. (1996) *J. Clin. Invest.* 97:1111–16; and Hofmann et al. (1994) *Endocrinology* 134:264–270.

These data help explain how TNF mediates the opposite effects of obesity and cachexia. TNF has functional similarities to leptin, which has been proposed to be an "adipostat." Zhang et al. (1994) *Nature* 372:425–432; Phillips et al. (1996) *Nature Genet.* 13:18–19; and Madej et al. (1995) *FEBS Lett.* 373:13–18. Like leptin, TNF is expressed and secreted by adipocytes and can travel to the brain. TNF administration also results in an increase in circulating leptin concentrations. Grunfeld et al. (1996) *J. Clin. Invest.* 97:2152–57. It is possible to reconcile the participation of TNF in obesity and cachexia. TNF can be considered one of many signals coming from adipose tissue that participate in the feedback mechanism that informs the hypothalamic center about the state of the adipocyte energy depot. TNF probably counteracts excessive energy intake and is able to stimulate thermogenesis either directly or by increasing sympathetic activity. TNF released by adipose tissue will also stimulate lipolysis, decrease LPL activity, decrease the expression of the glucose transporter GLUT4, and inhibit lipogenesis in the adipocyte, thus contributing to the maintenance (but not increased fat deposition) of the adipose tissue mass. In cachexia, however, the situation is different. A high production of TNF by activated macrophages (as a result of a tumor or an infection) contributes to anorexia, increased thermogenesis, and adipose tissue dissolution. However, a pathological state can be created where there is an excess of TNF informing the brain that adipose tissue needs dissolution. The two situations can thus be reconciled: in cachexia there is a pathological overproduction of TNF; in obesity, the physiological action of TNF as a signal to control food intake and energy expenditure is impaired. Argilés et al. (1997). *FASEB J.* 11:743–751.

Attempts have been made to ameliorate the untoward effects of TNF by treatment with monoclonal antibodies to TNF or with other proteins that bind TNF, such as modified TNF receptors. Patients with sepsis or septic shock have been treated with anti-TNF antibodies. Neither coagulation nor the fibrinolytic system was affected by an anti-TNF antibody in a study of patients with sepsis or septic shock. Satal et al. (1996) *Shock* 6:233–7. Some improvement in the clinical and histopathologic signs of Crohn's disease were afforded by treatment with anti-TNF antibodies. Neurath et al. (1997) *Eur. J. Immun.* 27:1743–50; van Deventer et al. (1997) *Pharm. World Sci.* 19:55–9; van Hogezand et al. (1997) *Scand. J. Gastro.* 223:105–7; and Stack et al. (1997) *Lancet* 349:521–4. In the treatment of experimental autoimmune encephalitis (EAE), an animal model of the human disease multiple sclerosis (MS), treatment with TNF-R fusion protein prevents the disease and the accompanying demyelination, suggesting the possible use of this treatment in MS patients. Klinkert et al. (1997) *J. Neuroimmun.* 72:163–8.

Regulation of TNF expression is being tested in treatment of endotoxic shock. Mohler et al. (1994) *Nature* 370:218–220. Modulation of TNF-R activity is also being approached by the use of peptides that bind intracellularly to the receptor or other component in the process to prevent receptor shedding. PCT patent publications: WO 95/31544, WO 95/33051; and WO 96/01642. Modulation of TNF-R activity is also postulated to be possible by binding of peptides to the TNF-R and interfering with signal transduction induced by TNF. European Patent Application EP 568 925.

Human TNF and LT mediate their biological activities, both on cells and tissues, by binding specifically to two distinct, although related, glycoprotein plasma membrane receptors of 55 kDa and 75 kDa (p55 and p75 TNF-R, respectively). Holtmann and Wallach (1987) *J. Immunol.* 139:151–153. The two receptors share 28 percent amino acid (AA) sequence homology in their extracellular domains, which are composed of four repeating cysteine-rich regions. Tartaglia and Goeddel (1992) *Immunol. Today* 13:151–153. However, the receptors lack significant AA sequence homology in their intracellular domains. Dembic et al. (1990) *Cytokine* 2:231–237. Due to this dissimilarity, they may transduce different signals and, in turn, exercise diverse functions.

Recent studies have shown that most of the known cellular TNF responses, including cytotoxicity and induction of several genes, may be attributed to p55 TNF-R activation. Engelmann et al. (1990) *J. Biol. Chem.* 265:1531–1536; Shalaby et al. (1990) *J. Exp. Med.* 172:1517–1520; and Tartaglia et al. (1991) *Proc. Natl. Acad. Sci. USA* 88:9292–9296. In addition, the p55 receptor controls early acute graft-versus-host disease. Speiser et al. (1997) *J. Immun.* 158:5185–90. In contrast, information regarding the biological activities of p75 TNF-R is limited. This receptor shares some activities with p55 TNF-R and specifically participates in regulating proliferation of and secretion of cytokines by T cells. Shalaby et al. (1990); and Gehr et al. (1992) *J. Immunol.* 149:911–917. Both belong to an ever-increasing family of membrane receptors including low-affinity nerve growth factor receptor (LNGF-R), FAS antigen, CD27, CD30 (Ki-1), CD40 (gp50) and OX 40. Cosman (1994) *Stem Cells* (Dayt.) 12:440–455; Meakin and Shooter (1992) *Trends Neurosci.* 15:323–331; Grell et al. (1994) *Euro. J. Immunol.* 24:2563–2566; Moller et al. (1994) *Int. J. Cancer* 57:371–377; Hintzen et al. (1994) *J. Immunol.* 152:1762–1773; Smith et al. (1993) *Cell* 73:1349–1360; Corcoran et al. (1994) *Eur. J. Biochem.* 223:831–840; and Baum et al. (1994) *EMBO J.* 13:3992–4001.

All of these receptors share a repetitive pattern of cysteine-rich domains in their extracellular regions. In accord with the pleiotropic activities of TNF and LT, most human cells express low levels (2,000 to 10,000 receptors/cell) of both TNF-Rs simultaneously. Brockhaus et al. (1990) *Proc. Natl. Acad. Sci.* USA 87:3127–3131. Expression of TNF-R on both lymphoid and non-lymphoid cells may be up and down-regulated by many different agents, such as bacterial lipopolysaccharide (LPS), phorbol myristate acetate (PMA; a protein kinase C activator), interleukin-1 (IL-1), interferon-gamma (IFN-γ) and IL-2. Gatanaga et al. (1991) *Cell Immunol.* 138:1–10; Yui et al. (1994) *Placenta* 15:819–835; and Dett et al. (1991) *J. Immunol.* 146:1522–1526. Although expressed in different proportions, each receptor binds TNF and LT with equally high affinity. Brockhaus et al. (1990); and Loetscher et al. (1990) *J. Biol. Chem.* 265:20131–20138. Initial studies showed that the complexes of human TNF and TNF-R are formed on the cell membrane, internalized wholly, and then either degraded or recycled. Armitage (1994) *Curr. Opin. Immunol.* 6:407–413; and Fiers (1991) *FEBS Lett.* 285:199–212.

TNF binding proteins (TNF-BP) were originally identified in the serum and urine of febrile patients, individuals with renal failure, cancer patients, and even certain healthy individuals. Seckinger et al. (1988) *J. Exp. Med.* 167:1511–1516; Engelmann et al. (1989) *J. Biol. Chem.* 264:11974–11980; Seckinger et al. (1989) *J. Biol. Chem.* 264:11966–11973; Peetre et al. (1988) *Eur. J. Haematol.* 41:414–419; Olsson et al. (1989) *Eur. J. Haematol.* 42:270–275; Gatanaga et al. (1990a) *Lymphokine Res.* 9:225–229; and Gatanaga et al. (1990b) *Proc. Natl. Acad. Sci USA* 87:8781–8784. In fact, human brain and ovarian tumors produced high serum levels of TNF-BP. Gatanaga et al. (1990a); and Gatanaga et al. (1990b). These molecules were subsequently purified, characterized, and cloned by different laboratories. Gatanaga et al. (1990b); Olsson et al. (1989); Schall et al. (1990) *Cell* 61:361–370; Nophar et al. (1990) *EMBO J.* 9:3269–3278; Himmler et al. (1990) *DNA Cell Biol.* 9:705–715; Loetscher et al. (1990) *Cell*

61:351–359; and Smith et al. (1990) *Science* 248:1019–1023. These proteins have been suggested for use in treating endotoxic shock. Mohler et al. (1993) *J. Immunol.* 151:1548–1561; Porat et al. (1995) *Crit. Care Med.* 23:1080–1089; Fisher et al. (1996) *N. Engl. J. Med.* 334:1697–1702; Fenner (1995) *Z. Rheumatol.* 54:158–164; and Jin et al. (1994) *J. Infect. Dis.* 170:1323–1326.

Human TNF-BP consist of 30 kDa and 40 kDa proteins found to be identical to the N-terminal extracellular domains of p55 and p75 TNF-R, respectively. The 30 kDa and 40 kDa TNF-BP are thus also termed p55 and p75 sTNF-R, respectively. Studies of these proteins have been facilitated by the availability of human recombinant 30 kDa and 40 kDa TNF-BP and antibodies which specifically recognize each form and allow quantitation by immunoassay. Heller et al. (1990) *Proc. Natl. Acad. Sci. USA* 87:6151–6155; U.S. Pat. No. 5,395,760; EP 418,014; and Grosen et al. (1993) *Gynecol. Oncol.* 50:68–77. X-ray structural studies have demonstrated that a TNF trimer binds with three soluble TNF-R (sTNF-R) molecules and the complex can no longer interact with TNF-R. Banner et al. (1993) *Cell* 73:431–445. The binding of the trimer and sTNF-R, however, is reversible and these reactants are not altered as a result of complex formation. At high molar ratios of sTNF-R to TNF, both recombinant and native human sTNF-R are potent inhibitors of TNF/LT biological activity in vitro as well as in vivo. Gatanaga et al. (1990b); Ashkenazi et al. (1991) *Proc. Natl. Acad. Sci. USA* 88:10535–10539; Lesslaur et al. (1991) *Eur. J. Immunol.* 21:2883–2886; Olsson et al. (1992) *Eur. J. Haematol.* 48:1–9; and Kohno et al. (1990) *Proc. Natl. Acad Sci. USA* 87:8331–8335.

Increased levels of TNF-R are also associated with clinical sepsis (septic peritonitis), HIV-1 infection, and other inflammatory conditions. Kalinkovich et al. (1995) *J. Interferon and Cyto. Res.* 15:749–757; Calvano et al. (1996) *Arch. Surg.* 131:434–437; and Ertel et al. (1994) Arch. Surg. 129:1330–1337. Sepsis, and septic shock affect thousands of patients every year and there is essentially no cure. This lethal syndrome is caused primarily by lipopolysaccharides (LPS) of Gram-negative bacteria and superantigens of Gram-positive bacteria. Clinical symptoms are initiated primarily by the release of endogenous mediators, such as TNF, from activated lymphoid cells into the bloodstream. TNF induces production of a cascade of other cytokines, including IL-1, IFN-γ, IL-8, and IL-6. These cytokines, along with other factors, promote the clinical symptoms of shock. Recombinant human sTNF-R is currently being tested in clinical trials to block TNF/LT activity in patients with septic shock and other conditions in which TNF and LT are thought to be pathogenic. Van Zee et al. (1992) *Proc. Natl. Acad. Sci. USA* 89:4845–4849. Balb/c mice, the primary animal model, and multiple techniques have been used to test the effects of TNF modulators and other treatments on septic peritonitis. Jin et al. (1994) *J. Infect. Dis.* 170:1323–1326; Mohler et al. (1993) *J. Immunol.* 151:1548–1561; Porat et al. (1995) *Crit. Care Med* 23:1080–1089; and Echtenacher et al. (1996) *Nature* 381:75–77. LPS-induced shock has been shown to be ameliorated by FR167653, a dual inhibitor of IL-1 and TNF production. Yamamoto et al. (1997) *Eur. J. Pharmacol.* 327:169–174.

While low levels of sTNF-R have been identified in the sera of normal individuals, high levels have been found in the sera of patients with chronic inflammation, infection, renal failure and various forms of cancer. Aderka et al. (1992) *Lymphokine Cytokine Res.* 11:157–159; Olsson et al. (1993) *Eur. Cytokine Netw.* 4:169–180; Diez-Ruiz et al. (1995) *Eur. J. Haematol.* 54:1–8; van Deuren (1994) *Eur. J. Clin. Microbiol. Infect. Dis.* 13 Suppl. 1:S12–6; Lambert et al. (1994) *Nephrol. Dial. Transplant.* 9:1791–1796; Halwachs et al. (1994) *Clin. Investig.* 72:473–476; Gatanaga et al. (1990a); and Gatanaga et al. (1990b). Serum levels of sTNF-R rise within minutes and remain high for 7 to 8 hours after the intravenous injection of human recombinant TNF or IL-2 into human cancer patients. Aderka et al. (1991) *Cancer Res.* 51:5602–5607; and Miles et al. (1992) *Br. J. Cancer* 66:1195–1199. It has also been observed that serum sTNF-R levels are chronically elevated in cancer patients and may remain at high levels for years. Grosen et al. (1993). It is clear that sTNF-R are natural inhibitors of these cytokines and regulate their biological activity post secretion. Fusion proteins consisting of a sTNF-R linked to a portion of the human IgG1 have also been developed for treating rheumatoid arthritis and septic shock. Moreland et al. (1997) *N. Eng. J. Med.* 337:141–7; Abraham et al. (1997) *JAMA* 277:1531–8.

New evidence has yielded information on cellular regulation of secreted cytokines. The evidence indicates that cells release molecules which resemble or contain the binding site of the specific membrane receptors. Massague and Pandiella (1993) *Annu. Rev. Biochem.* 62:515–541; and Rose-John and Heinrich (1994) *Biochem. J.* 300:281–290. These soluble forms specifically bind and, in the appropriate molar ratios, inactivate the cytokine by steric inhibition. Therefore, this may be a general phenomenon responsible for the regulation of cytokines and membrane antigens.

In addition to TNF-R, various types of membrane molecules have both soluble and membrane forms, including (i) cytokine receptors, e.g., IL-1R, IL-2R, IL-4R, IL-5R, IL-6R, IL-7R, IL-9R, granulocyte-colony stimulating factor-R (G-CSF-R), granulocyte-macrophage-colony stimulating factor-R (GM-CSF-R), transforming growth factor-β-R (TGFβ-R), platelet-derived growth factor-R (PDGF-R), and epidermal growth factor-R (EGF-R); (ii) growth factors, e.g., TNF-(pro-TNF-α), TGF-α, and CSF-1; (iii) adhesion molecules, e.g., intracellular adhesion molecule-1 (ICAM-1/CD54) and vascular cell membrane adhesion molecule (VCAM-1/CD106); (iv) TNF-R/NGF-R superfamily, e.g., LNGF-R, CD27, CD30, and CD40; and (v) other membrane proteins, e.g. transferrin receptor, CD14 (receptor for LPS and LPS binding protein), CD16 (FcγRIII), and CD23 (low-affinity receptor for IgE). Colotta et al. (1993) *Science* 261:472–475; Baran et al. (1988) *J. Immunol.* 141:539–546; Mosley et al. (1989) *Cell* 59:335–348; Takaki et al. (1990) *EMBO J.* 9:4367–4374; Novick et al. (1989) *J. Exp. Med.* 170:1409–1414; Goodwin et al. (1990) *Cell* 60:941–95 1; Renauld et al. (1992) *Proc. Natl. Acad. Sci. USA* 89:5690–5694; Fukunaga et al. (1990) *Proc. Natl. Acad. Sci. USA* 87:8702–8706; Raines et al. (1991) *Proc. Natl. Acad Sci. USA* 88:8203–8207; Lopez-Casillas et al. (1991) *Cell* 67:785–795; Tiesman and Hart (1993) *J. Biol. Chem.* 268:9621–9628; Khire et al. (1990) *Febs. Lett.* 272:69–72; Kriegler et al. (1988) *Cell* 53:45–53; Pandiella and Massague (1991) *Proc. Natl. Acad Sci. USA* 88:1726–1730; Stein et al. (1991) *Oncogene* 6:601–605; Seth et al. (1991) *Lancet* 338:83–84; Hahne et al. (1994) *Eur. J. Immunol.* 24:421–428; Zupan et al. (1989) *J. Biol. Chem.* 264:11714–11720; Loenen et al. (1992) *Eur. J. Immunol.* 22:447–455; Latza et al. (1995) *Am. J. Pathol.* 146:463–471; Chitambar (1991) *Blood* 78:2444–2450; Landmann et al. (1992) *J. Leukoc. Biol.* 52:323–330; Huizinga et al. (1988) *Nature* 333:667–669; and Alderson et al. (1992) *J. Immunol.* 149:1252–1257.

In vitro studies with various types of cells have revealed that there are two mechanisms involved in the production of soluble receptors and cell surface antigens. One involves translation from alternatively spliced mRNAs lacking transmembrane and cytoplasmic regions, which is responsible for the production of soluble IL-4R, IL-5R, IL-7R, IL-9R, G-CSF-R, and GM-CSF-R. Rose-John and Heinrich (1994); and Colotta et al. (1993). The other mechanism involves proteolytic cleavage of the intact membrane receptors and antigens, known as shedding. Proteolysis appears to be involved in the production of soluble LNGF-R, TNF-R, CD27, CD30, IL-1R, IL-6R, TGFβ-R, PDGF-R, and CD14 (Id.).

Both soluble p55 and p75 TNF-R do not appear to be generated from processed mRNA, since only full length receptor mRNA has been detected in human cells in vitro. Gatanaga et al. (1991). Carboxyl-terminal sequencing of the human soluble p55 TNF-R indicates that a cleavage site may exist between Asn 172 and Val 173. Gullberg et al. (1992) *Eur. J. Cell. Biol.* 58:307–312. This evidence is supported by the finding that human TNF-R with the mutation at Asn 172 and Val 173 was not released as effectively as native TNF-R on COS-1 cells transduced with cDNA of human TNF-R. Gullberg et al. (1992). The cytoplasmic portion of TNF-R does not appear to play an important role in releasing the soluble receptor forms from transduced COS-1 cells. COS-1 cells release sTNF-R even when transduced with cDNA of human p55 TNF-R which expresses only the extracellular domain but not the cytoplasmic domain. (Id.) sTNF-R shedding is not affected by dexamethasone, gold sodium thiomalate, or prostaglandin E2. Seitz et al. (1997) *J. Rheumatology* 24:1471–6. Collectively, these data support the concept that human sTNF-R are produced by proteolytic cleavage of membrane TNF-R protein.

PMA is an extremely strong and rapid inducer of TRRE and, indirectly, TNF-R. Basically, PMA is a powerful stimulator of protein kinase C which is anchored inside the cell membrane once activated. Data suggest that (i) TRRE is stored in the cytoplasm very close to the cell membrane ready to be secreted through the protein kinase C cascade by PMA stimulation; (ii) TRRE is a peripheral (or extrinsic) membrane protein which is dissociated from the membrane through the change of interactions with other proteins or with any phospholipid by stimulated protein kinase C; or (iii) TRRE is an integral (or intrinsic) membrane protein which is cleaved and secreted to be an active form after its cytoplasmic portion interacts directly or indirectly with protein kinase C.

TRRE induction by PMA does not require de novo protein synthesis, RNA synthesis and transmission inside the cytoplasm, but only membrane internalization and movement. This is compatible with the data that TRRE was released very quickly by PMA stimulation and halted once PMA was removed. With PMA stimulation, however, TRRE synthesis begins at the same time as TRRE release. After the initial release, TRRE accumulates inside the cell or on the cell surface within 2 hours ready to be secreted by the next stimulation. Evidence for direct cleavage of TNF-R is that the shedding of sTNF-R occurs very quickly (5 minutes), with maximal shedding within 30 minutes.

In addition to PMA, shedding of sTNF-R has been known to be enhanced by several cytokines including TNF, IL-1, IL-6, IL-10 and IFN, leukocyte migration enhancement factors including formyl-methionyl-leucyl-phenylalanine (fMLP) and C5a, and calcium ionophore. Gatanaga (1993) *Lymphokine Res.* 12:249–253; Porteu (1994) *J. Biol. Chem.* 269:2834–2840; van der Poll (1995) *J. Immunol.* 155:5397–5401; Porteu et al. (1991); and Porteu and Natah (1990) *J. Exp. Med.* 172:599–607. IL-10 and epinephrine induce TRRE in the human monocyte cell line THP-1.

IL-10 is a potent inhibitor of monocyte- and macrophage-functions. Moore (1993) *Annu. Rev. Immunol.* 11:165–190. IL-10 has anti-inflammatory activity on monocytes and inhibits the release of pro-inflammatory cytokines including TNF and IL-1. Bogdan et al. (1991) *J. Exp. Med.* 174:1549–1555; Fiorentino et al. (1991) *J. Immunol.* 147:3815–3822; de Waal Malefyt et al. (1991) *J. Exp. Med.* 174:1209–1220; Katsikis et al. (1994) *J. Exp. Med.* 179:1517–1527; Joyce et al. (1994) *Eur. J. Immunol.* 24:2699–2705; and Simon et al. (1994) *Proc. Natl. Acad Sci. USA* 91:8562–8566. Elevated levels of IL-10 have been detected in plasma of patients with sepsis, and after administration of LPS to animals. Marchant et al. (1994) *Lancet* 343:707–708; Derkx et al. (1995) *J. Infect. Dis.* 171:229–232; Durez et al. (1993) *J. Exp. Med* 177:551–555; and Marchant et al. (1994) *Eur. J. Immunol.* 24:1167–1171. In vivo, IL-10 has also been shown to protect mice against endotoxin shock. Gerard et al. (1993) *J. Exp. Med.* 177:547–550; and Howard et al. (1993) *J. Exp. Med.* 177:1205–1208. IL-10 leads to increased levels of mRNA for p75 TNF-R, increased release of soluble p75 TNF-R and a concomitant reduction of surface expression of p75 TNF-R on monocytes. Joyce et al. (1994). Thus, IL-10 may be considered to reduce the pro-inflammatory potential of TNF by (i) inhibiting the release of TNF itself, and (ii) down-regulating surface TNF-R expression while (iii) increasing production of sTNF-R capable of neutralizing TNF cytotoxicity. Joyce et al. (1994); and Leeuwenberg et al. (1994) *J. Immunol.* 152:4036–4043. The data presented herein that IL-10 may induce TRRE activity are consistent with these findings and indicate a newly revealed function of IL-10 as an anti-inflammatory cytokine.

In stressful situations, including endotoxic shock, serum levels of catecholamines and glucocorticoids are elevated chiefly from adrenal medulla and adrenal cortex, respectively, in response to high serum level of adrenocorticotropic hormone (ACTH) throughout the whole body system. TNF also has been implicated in the early metabolic events following stressful situations, and infusion of recombinant TNF in dogs was associated with increase of serum levels of catecholamines, glucocorticoids and glucagon. Tracey et al. (1987) *Surg. Gynecol. Obstet.* 164:415–422. As a local phenomenon, epinephrine and norepinephrine are found in macrophages which express β-adrenergic receptors and these endogenous catecholamines seem to regulate LPS-induced TNF production in an autocrine fashion in vitro. Hjemdahl et al. (1990) *Br. J. Clin. Pharmacol.* 30:673–682; Hjemdahl et al. (1990) *Br. J. Clin. Pharmacol.* 30:673–682; Talmadge et al. (1993) *Int. J. Immunopharmacol.* 15:219–228; and Spengler et al. (1994) *J. Immunol.* 152:3024–3031. Exogenous epinephrine and isoproterenol, a specific adrenergic agonist, inhibit the production of TNF from human blood and THP-1 cells stimulated by LPS. Hu et al. (1991) *J. Neuroimmunol.* 31:35–42; and Severn (1992) *J. Immunol.* 148:3441–3445.

While epinephrine may be an important endogenous inhibitor of TNF production, especially in sepsis, epinephrine also decreases the number of TNF-R on macrophages. Bermudez et al. (1990) *Lymphokine Res.* 9:137–145. It has been shown that in trauma patients both p55 and p75 TNF-R levels were significantly elevated along with high serum level of epinephrine within 1 hour of injury. Tan et al. (1993) *J. Trauma* 34:634–638. These findings are in agreement with the data that epinephrine induced TRRE activity and may lead to the increase of sTNF-R.

In addition to epinephrine, insulin and glucagon have the function to down-regulate TNF-R. Bermudez et al. (1990).

Many inflammatory cytokines besides IL-10 may influence the shedding of sTNF-R including TNF, IL-1, IL-6, and IFN for up-regulation and IL-4 for down-regulation. van der Poll et al. (1995); Gatanaga et al. (1993); and Joyce et al. (1994).

Two reports describe the involvement of a metalloprotease in the production of sTNF-R by utilizing a specific metalloprotease inhibitor, TNF-α protease inhibitor (TAPI). TAPI blocks the shedding of soluble p75 and p55 TNF-R, respectively. Crowe et al. (1995); and Mullberg et al. (1995). Moreover, the processing of pro-TNF on the cell membrane was reported to be dependent on a matrix metalloprotease (MMP)-like enzyme. Gearing et al. (1994); and Gearing et al. (1995). MMPs are a family of structurally related matrix-degrading enzymes that play a major role in tissue remodeling and repair associated with development and inflammation. Matrisian (1990) *Trends Genet.* 6:121–125; Woessner (1991) *FASEB J.* 5:2145–2154; and Birkedal-Hansen et al. (1993) *Crit. Rev. Oral Biol. Med.* 4:197–250. Pathological expression of MMPs is associated with tumor invasiveness, osteoarthritis, atherosclerosis, and pulmonary emphysema. Mignatti et al. (1986) *Cell* 47:487–498; Khokha (1989) *Science* 243:947–950; Dean et al. (1989) *J. Clin. Invest.* 84:678–685; Henney et al. (1991) *Proc. Natl. Acad. Sci. USA* 88:8154–8158; and Senior et al. (1989) *Am. Rev. Respir. Dis.* 139:1251–1256. MMPs are $Zn^{2+}$-dependent enzymes which have $Zn^{2+}$ in their catalytic domains. $Ca^{2+}$ stabilizes their tertiary structure significantly. Lowry et al. (1992) *Proteins* 12:42–48; and Lovejoy et al. (1994) *Science* 263:375–377. Thus, according to the similar metal dependency, at least one TRRE may be a part of the MMPs family of which 11 MMPs have been cloned.

The substrate-specificity of TRRE has been investigated using membrane receptors and antigens other than the two TNF-Rs. These receptors and antigens are expressed at sufficient levels on THP-1 cells to be detected by FACS analysis including (i) IL-1R, whose soluble form is known to be produced by proteolytic cleavage, (ii) CD30 (ki-1), which belongs to the same receptor family as TNF-R (TNF-R/NGF-R superfamily) and whose soluble form is produced presumably by a $Zn^{2+}$-dependent metalloprotease, (iii) CD54 (ICAM1), which belongs to immunoglobulin superfamily of adhesion molecules including VCAM-1 and is known to have a soluble form, and (iv) CD11b, which belongs to the integrin family of adhesion molecules and which has not been shown to have a soluble form. TRRE is apparently very specific to only the cleavage of both TNF-Rs and did not affect any other membrane receptors and antigens which have soluble forms.

Given the involvement of TNF in a variety of pathological conditions, it would be desirable to identify and characterize factors that modulate expression of sequences encoding TRREs and/or which modulate activity of TRREs. The present invention relates to identification and characterization of such factors, as well as to methods of modulating TRRE activity.

SUMMARY OF THE INVENTION

The invention encompasses a composition which modulates TRRE activity. In one embodiment, the composition increases TRRE activity. In another embodiment, the composition decreases TRRE activity. In one embodiment, the composition further comprises a physiologically acceptable buffer.

In one embodiment of the present invention, the composition is encoded by a nucleic acid of at least 15 contiguous nucleotides of clones 2-8, 2-9, 2-14, 2-15, P2-2, P2-10, P2-13, P2-14, and P2-15, which are represented by SEQ ID NOs:1 to 10, or a complementary strand thereof. In another embodiment, the composition is an RNA encoded by at least 15 contiguous nucleotides of a sequence presented in any of SEQ ID NOs. 1 to 10, or a complementary strand thereof. The invention also encompasses nucleic acids encoding the amino acid sequences of at least 5 contiguous amino acids of any of SEQ ID NOs:147 to 154. In another embodiment, the composition is a protein encoded by at least 10 contiguous codons of a nucleic acid sequence presented in any of SEQ ID NOs. 1 to 10, or a complementary strand thereof In another embodiment, the composition is an antisense nucleic acid that binds to a nucleic acid comprising at least 15 contiguous nucleotides of a nucleic acid sequence presented in any of SEQ ID NOs. 1 to 10, or a complementary strand thereof. In another embodiment, the composition is an antibody that binds to a protein encoded by at least 10 contiguous codons of any of SEQ ID NOs. 1 to 10, or a complementary strand thereof. In one embodiment, the composition further comprises a physiologically acceptable buffer.

In another embodiment, the invention encompasses a method of obtaining a composition which alters TRRE activity, comprising the steps of: introducing into a first cell with known TRRE activity clones from a library of a second cell with a different TRRE activity; selecting a first cell with altered TRRE activity; and isolating the clone from the first cell, wherein the clone encodes the composition. In one embodiment the method identifies clones which enhance TRRE activity, and in this case the TRRE activity of the first cell is higher than that of the second cell. In a variant of this method, the first and second cells are of the same cell type, and the change in TRRE activity can be caused by a change in the gene copy number; e.g., TRRE activity can increase if more copies of a gene encoding a factor that enhances expression of the TRRE are present, or TRRE activity can decrease if more copies of a gene encoding a factor which inhibits TRRE expression are present. In one embodiment the method identifies clones which decrease TRRE activity, and in this case the TRRE activity of the first cell is lower than that of the second cell. The invention further comprises a clone identified by this method.

In another embodiment, the invention encompasses a method of treating an individual having a disease associated with altered levels or activity of TNF comprising administering an amount of the composition which alters TRRE activity sufficient to indirectly or directly normalize said levels of TNF. In one embodiment, the disease is cancer. In various embodiments, the cancer is selected from the group consisting of astrocytoma, oligodendroglioma, ependymoma, medulloblastoma, primitive neural ectodermal tumor, pancreatic ductal adenocarcinoma, small and large cell lung adenocarcinomas, squamous cell carcinoma, bronchoalveolarcarcinoma, epithelial adenocarcinoma and liver metastases thereof, hepatoma, cholangiocarcinoma, ductal and lobular adenocarcinoma, squamous and adenocarcinomas of the uterine cervix, uterine and ovarian epithelial carcinomas, prostatic adenocarcinomas, transitional squamous cell bladder carcinoma, B and T cell lymphomas (nodular and diffuse), plasmacytoma, acute and chronic leukemias, malignant melanoma, soft tissue sarcomas, and leiomyosarcomas. In one embodiment the disease is cachexia. In another embodiment the disease is an inflammatory disorder. In one embodiment the disease is selected from the group consisting of autoimmune diseases, endotoxin shock, rheumatoid arthritis, trauma, infection and multiple sclerosis. In one embodiment the method of administration is selected from the group consisting of locally, parenterally, subcutaneously, intramuscularly, intraperitoneally, intracavity, intrathecally, and intravenously.

In another embodiment, the invention encompasses a method of measuring the TNF-receptor releasing (TRRE) activity of a test protein, comprising the steps of: obtaining cells that do not express significant amounts of TNF-R (TNF-R⁻ cells); manipulating the cells to express recombinant TNF-R (TNF-R⁺ cells); incubating the TNF-R⁺ cells in a suitable medium in the absence and presence of the protein; and measuring the level of soluble TNF-R in the cell supernatant, where the ratio of soluble TNF-R in the absence and presence of the protein is indicative of the TRRE activity of the protein. In another embodiment, the invention encompasses a protein with TRRE activity identified by this method.

In another embodiment, the invention encompasses a method of diagnosing a disease associated with altered levels or activity of the protein affecting TRRE activity, comprising the steps of: obtaining a biological sample from a patient; measuring activity of the protein in the sample; and comparing the activity to the activity of a control biological sample. In one embodiment the disease is cancer. In one embodiment the cancer is selected from the group consisting of glioblastoma, melanoma, neuroblastoma, adenocarcinoma, soft tissue sarcoma, leukemias, lymphomas and carcinoma. In one embodiment the cancer is carcinoma and is selected from the group consisting of astrocytoma, oligodendroglioma, ependymoma, medulloblastoma, primitive neural ectodermal tumor, pancreatic ductal adenocarcinoma, small and large cell lung adenocarcinomas, squamous cell carcinoma, bronchoalveolarcarcinoma, epithelial adenocarcinoma and liver metastases thereof, hepatoma, cholangiocarcinoma, ductal and lobular adenocarcinoma, squamous and adenocarcinomas of the uterine cervix, uterine and ovarian epithelial carcinomas, prostatic adenocarcinomas, transitional squamous cell bladder carcinoma, B and T cell lymphomas (nodular and diffuse), plasmacytoma, acute and chronic leukemias, malignant melanoma, soft tissue sarcomas, and leiomyosarcomas.

In another embodiment, the invention encompasses a method of treating a disease associated with elevated levels of soluble TNF receptor comprising administering an amount of an inhibitor of TNF receptor releasing enzyme effective to decrease the levels of soluble TNF receptor. In another embodiment, the disease is cancer. In another embodiment, the cancer is selected from the group consisting of astrocytoma, oligodendroglioma, ependymoma, medulloblastoma, primitive neural ectodermal tumor, pancreatic ductal adenocarcinoma, small and large cell lung adenocarcinomas, squamous cell carcinoma, bronchoalveolarcarcinoma, epithelial adenocarcinoma and liver metastases thereof, hepatoma, cholangiocarcinoma, ductal and lobular adenocarcinoma, squamous and adenocarcinomas of the uterine cervix, uterine and ovarian epithelial carcinomas, prostatic adenocarcinomas, transitional squamous cell bladder carcinoma, B and T cell lymphomas (nodular and diffuse), plasmacytoma, acute and chronic leukemias, malignant melanoma, soft tissue sarcomas, and leiomyosarcomas. In another embodiment, the inhibitor is selected from the group consisting of a metalloprotease inhibitor, an antibody that blocks the effective interaction between TNF receptor and TNF receptor releasing enzyme, a polynucleotide encoding said antibody, an antisense oligonucleotide specific for the gene encoding tumor necrosis receptor releasing enzyme, and a ribozyme specific for the gene encoding TNF receptor releasing enzyme. In another embodiment, the method further comprises the step of administering an amount of at least one cytokine effective to enhance an immune response against the cancer. In another embodiment, the cytokine is selected from the group consisting of interleukin 2, interleukin 4, granulocyte macrophage colony stimulating factor, and granulocyte colony stimulating factor. In another embodiment, the method further comprises the step of administering a chemotherapeutic agent. In another embodiment, the chemotherapeutic agent is selected from the group consisting of radioisotopes, vinca alkaloids, adriamycin, bleomycin sulfate, Carboplatin, cisplatin, cyclophosphamide, Cytarabine, Dacarbazine, Dactinomycin, Duanorubicin hydrochloride, Doxorubicin hydrochloride, Etoposide, fluorouracil, lomustine, mechlorethamine hydrochloride, melphalan, mercaptopurine, methotrexate, mitomycin, mitotane, pentostatin, pipobroman, procarbaze hydrochloride, streptozotocin, taxol, thioguanine, and uracil mustard.

DETAILED DESCRIPTION OF THE INVENTION

The invention encompasses factors which modulate tumor necrosis factor receptor (TNFR) releasing enzymatic (TRRE) activity. The invention encompasses factors which increase or decrease TRRE activity. Effective amounts of the compositions of the present invention are those that alter TRRE by at least about 10%, more preferably by at least about 25%, more preferably by at about 50%, and even more preferably by at least about 75%. The invention encompasses nucleic acid sequences that act as templates for RNAs or encode proteins that that substantially alter TRRE in a cell, and methods of use thereof, and methods of screening thereof. TNF is a major proinflammatory and immunomodulatory cytokine produced during immune responses. TNF also regulates the expression of IL-2R leading to enhanced T cell responses mediated by IL-2 and appears to be required for generating proliferative responses in mixed lymphocyte cultures. Additional studies have shown that CD8⁺, CTL and lymphokine activated killer cells are optimally induced with TNF, in combination with IL-2, suggesting the importance of this cytokine in regulating cytotoxic effector function. As discussed in detail above, TNF mediates its activity by binding to a TNF-R. Soluble TNF-Rs inhibit TNF activity by two methods: they decrease the available binding sites on a cell and bind to soluble TNF to decrease the local concentration. The present invention encompasses compositions and methods for modulating the level of soluble TNF-R by modulating the cleavage of TNF-R from the cell surface and thus indirectly modulating the effect of TNF.

Figure 6:
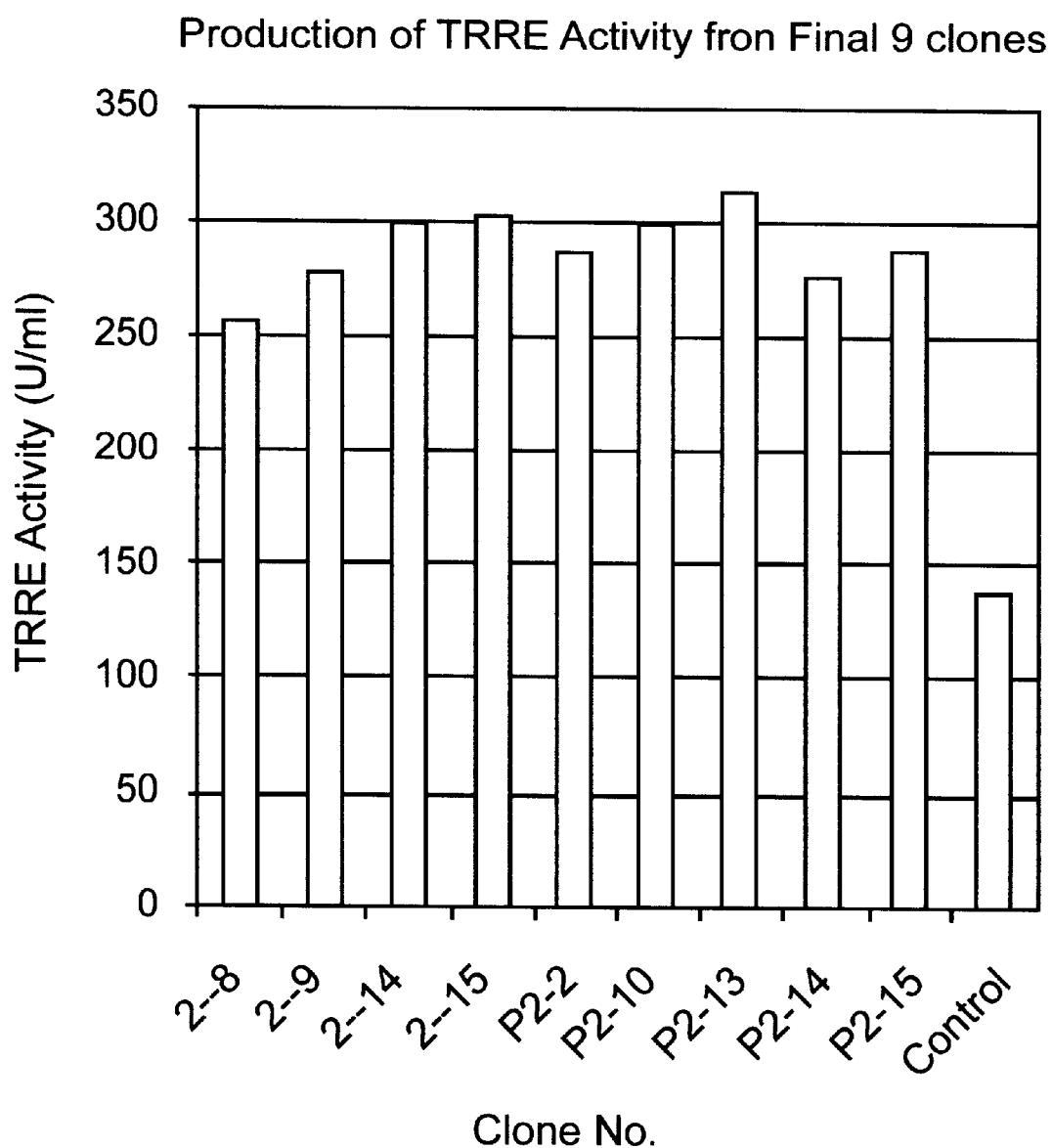
FIG. 6 is a graph depict the effect of various clones on TRRE activity in COS-1 cells.

Nucleic acid sequences of clones capable of enhancing TRRE activity are presented in SEQ ID NOs:1 to 10. The corresponding polypeptide sequences thereof are presented in SEQ ID NOs:147 to 154. These sequences were generated from clones designated 2-8, 2-9, 2-14, 2-15, P2-2, P2-10, P2-13, P2-14, and P2-15, each of which enhances 130%, as shown in FIG. 6. The clones were prepared from a library (Stratagene, La Jolla, Calif.) of Jurkat cells, which have a high TRRE activity, transformed into COS-1 cells, which normally lack TRRE activity, as described in Example 5. Jurkat library clones which produced high TRRE activity in COS-1 cells were isolated and sequenced. This method can also be used to obtain additional genes which enhance TRRE activity. In addition, in a method of obtain clones which reduce TRRE activity, a library of cells with reduced TRRE activity can be introduced into a cell with relatively higher TRRE activity. Those clones which reduce TRRE activity can be thus identified.

The sequences of SEQ ID NOs:1 to 10 were analyzed by a BLAST (Basic Local Alignment Search Tool) sequence analysis to determine if they were similar or identical to known genes. All these sequences were found to be novel, except that of clone 2-8 (sequence designation AIM3T3, SEQ ID NO:2), which is highly similarly to the *M. musculus* 45S pre-rRNA gene, clone 2-14 (sequence designation AIM4, SEQ ID NO:4), which is highly similar to human arfaptin 2, and clone P2-10 (sequence designation AIM7, SEQ ID NO:7), which is highly similar to the human insulin-like growth factor II receptor. In addition, the sequence of clone 2-15 (sequence designation AIM5, SEQ ID NO:5) is novel but has some similar to human eIF-5A transcription factor. None of these known genes has previously been linked to modulating TRRE activity.

In addition to using the Jurkat library (or similar library from a cell expressing high TRRE activity), an in vitro TRRE activity can be used to identify genes which enhance TRRE activity. Briefly, in this assay (described in detail in Example 1), a gene encoding a membrane-bound TNF receptor (TNF-R) is transformed into a cell which normally lacks this gene. These cells and controls are incubated with medium to be tested for TRRE activity. The supernatant is then collected and tested for solubilized TNF-R by ELISA. Mutants, variants, and derivatives of the polypeptides disclosed herein can be assayed for TRRE activity with this assay. In another embodiment, nucleic acids thought to encode proteins or RNAs that affect TRRE activity can be transformed into cells in this assay and tested for their effect on TRRE activity. This invention therefore encompasses polypeptides and genes identified by methods of obtaining polypeptides and genes that enhance TRRE activity.

This in vitro TRRE activity assay can also be used to identify factors which inhibit TRRE activity. Antibodies to proteins which enhance TRRE activity can be introduced into the cellular medium along with such proteins to determine if the antibodies block TRRE activity. Anti-sense RNAs to nucleic acids encoding TRRE activity can also be tested in this assay.

The terms "polypeptide", "peptide" and "protein" are used interchangeably herein to refer to polymers of amino acid residues of any length. The polymer can be linear or branched, it can comprise modified amino acids or amino acid analogs, and it can be interrupted or modified by chemical moieties other than amino acids. The terms also encompass an amino acid polymer that has been modified naturally or by chemical intervention; for example, disulfide bond formation, glycosylation, lipidation, acetylation, phosphorylation, or any other manipulation or modification, such as conjugation with a labeling or bioactive component. Unless stated or implied otherwise, the term TRRE includes any polypeptide monomer or polymer with TRRE enzymatic specificity, including the intact TRRE, and smaller and larger functionally equivalent polypeptides, as described herein. The present invention encompasses polypeptides encoded by at least 5, preferably at least 10, more preferably at least 15, contiguous amino acids encoded by any of SEQ ID NOs:1 to 10. The invention further encompasses polypeptides represented in SEQ ID NOs: 147 to 154, or functional fragments, variants and derivatives thereof capable of modulating TRRE activity in a cell.

A "fusion polypeptide" is a polypeptide comprising regions in a different position in the sequence than occurs in nature. The regions can normally exist in separate proteins and are brought together in the fusion polypeptide; they can normally exist in the same protein but are placed in a new arrangement in the fusion polypeptide; or they can be synthetically arranged. For instance, as described below, the invention encompasses recombinant proteins that are comprised of a functional portion of TRRE and an antibody. Methods of making these fusion proteins are known in the art and are described, for instance, in WO93/07286.

A "functionally equivalent fragment" of a TRRE polypeptide varies from the native sequence by addition(s), deletion(s), or substitution(s), or any combination thereof, while preserving at least one functional property of the fragment relevant to the context in which it is being used. A functionally equivalent fragment of a TRRE polypeptide typically has the ability to bind membrane bound TNF-R and enzymatically cleave TNF-R to provide soluble TNF-R. Amino acid substitutions, if present, are preferably conservative substitutions that do not deleteriously affect folding or functional properties of the peptide. Groups of functionally related amino acids within which conservative substitutions can be made are glycine/alanine; valine/isoleucine/leucine; asparagine/glutamine; aspartic acid/glutamic acid; serine/threonine/methionine; lysine/arginine; and phenylalanine/tyrosine/tryptophan. Polypeptides of this invention can be in glycosylated or unglycosylated form, can be modified post-translationally (e.g., removal of signal peptide, transmembrane or cytoplasmic regions, acetylation, and phosphorylation) or can be modified synthetically (e.g., by a labeling group).

Effective amounts of a polypeptides of the present invention can be administered to a subject or cell in order to modulate TRRE activity in the subject or cell. In addition, variants, mutants and derivatives of the polypeptides described herein can be tested for TRRE activity in an in vitro assay. Those which display high activity can then be administered to subjects. Alternatively, polynucleotides encoding these polypeptides, variants, mutants or derivatives can be introduced. In the case of TRRE genes in which the gene product is an RNA (e.g., an rRNA), it is preferable to administer a nucleic acid which is a DNA. Administration can be performed locally, parenterally, subcutaneously, intramuscularly, intraperitoneally, intracavity, intrathecally, and intravenously, or via any method known in the art. The preparation of pharmaceutical compositions that contain a polynucleotide or polypeptide as an active ingredient is conducted in accordance with generally accepted procedures for the preparation of pharmaceutical preparations. See, for example, *Remington's Pharmaceutical Sciences* 18th Edition (1990), E. W. Martin ed., Mack Publishing Co., PA. Depending on the intended use and mode of administration, it may be desirable to process the active ingredient further in the preparation of pharmaceutical compositions. Appropriate processing may include sterilizing, mixing with appropriate non-toxic and non-interfering components, dividing into dose units, and enclosing in a delivery device. Various methods of delivering proteins and nucleic acids into cells and individuals are known in the art.

In addition, the polypeptides and polynucleotides disclosed herein can be used to inhibit or decrease TRRE activity levels in a cell or subject, particularly a subject suffering from an indication characterized by excessive TNF activity. Such inhibitors include metalloprotease inhibitors, an antibody which blocks the effective interaction between TNF receptor and TRRE or a polynucleotide encoding such an antibody, an antisense oligonucleotide specific for a TRRE, and a ribozyme specific for a gene encoding TRRE. Antisense nucleic acids (e.g., antisense RNAs) include those complementary to the sequences of SEQ ID NOs:1 to 10. These can bind to the nucleic acids in a cell and prevent their expression. Alternatively, antisense nucleic acids can be constructed to bind to mRNAs encoded by these sequences to prevent their translation. Furthermore, the polypeptides described in SEQ ID NOs:147 to 154 can be used to generate antibodies. Administration of an effective amount of these antibodies to a cell or subject can reduce TRRE activity in that cell or subject. In addition to an inhibitor of TRRE activity, a subject can be treated with a cytokine such as IL-2, -4, GM-CSF, or GSF and/or a chemotherapeutic agent such as radioisotopes, vinca alkaloids, adriamycin, bleomycin sulfate, Carboplatin, cisplatin, cyclophosphamide, Cytarabine, Dacarbazine, Dactinomycin, Duanorubicin hydrochloride, Doxorubicin hydrochloride, Etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, taxol, thioguanine, and uracil mustard. Methods of administering these various agents are known in the art.

An "effective amount" in treatment is an amount sufficient to effect beneficial or desired clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

Subjects including those who are suspected of being at risk of a pathological effect of any neoplasia, particularly carcinoma, are suitable for treatment with the pharmaceutical compositions of this invention. Those with a history of cancer are especially suitable. Suitable subjects for therapy comprise two groups, which may be distinguished by clinical criteria. Patients with "advanced disease" or "high tumor burden" are those who bear a clinically measurable tumor. A clinically measurable tumor is one that can be detected on the basis of tumor mass (e.g., by palpation, CAT scan, or X-ray; positive biochemical or histopathological markers on their own are insufficient to identify this population). A pharmaceutical composition embodied in this invention is administered to these patients to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group". These are individuals who have had a history of cancer, but have been responsive to another mode of therapy. The prior therapy may have included (but is not restricted to) surgical resection, radiotherapy, and traditional chemotherapy. As a result, these individuals have no clinically measurable tumor. However, they are suspected of being at risk for progression of the disease, either near the original tumor site, or by metastases.

This adjuvant group can be further subdivided into high-risk and low-risk individuals. The subdivision is made on the basis of features observed before or after the initial treatment. These features are known in the clinical arts, and are suitably defined for each different cancer. Features typical of high risk subgroups are those in which the tumor has invaded neighboring tissues, or involvement of lymph nodes.

Another suitable group of subjects is those with a genetic predisposition to cancer but who have not yet evidenced clinical signs of cancer. For instance, women testing positive for a genetic mutation associated with breast cancer, but still of childbearing age, may wish to receive TRRE inhibitor treatment prophylactically to prevent the occurrence of cancer until it is suitable to perform preventive surgery.

Of course, crossovers between these two patient groups occur, and the pharmaceutical compositions of this invention can be administered at any time that is appropriate. For example, therapy can be conducted before or during traditional therapy of a patient with high tumor burden, and continued after the tumor becomes clinically undetectable. Therapy can be continued in a patient who initially fell in the adjuvant group, but is showing signs of recurrence. The attending physician can determine how or when the compositions of this invention are to be used.

As provided herein, treatment, diagnosis and monitoring of cancers includes any cancers known in the art. These include, but are not limited to, glioblastoma, melanoma, neuroblastoma, adenocarcinoma, soft tissue sarcoma, leukemias, lymphomas and carcinoma. The invention is particularly useful for treatment, diagnosis and monitoring of carcinomas. Carcinomas include, but are not limited to, astrocytoma, oligodendroglioma, ependymoma, medulloblastoma, primitive neural ectodermal tumor, pancreatic ductal adenocarcinoma, small and large cell lung adenocarcinomas, squamous cell carcinoma, bronchoalveolarcarcinoma, epithelial adenocarcinoma and liver metastases thereof, hepatoma, cholangiocarcinoma, ductal and lobular adenocarcinoma, squamous and adenocarcinomas of the uterine cervix, uterine and ovarian epithelial carcinomas, prostatic adenocarcinomas, transitional squamous cell bladder carcinoma, B and T cell lymphomas (nodular and diffuse), plasmacytoma, acute and chronic leukemias, malignant melanoma, soft tissue sarcomas and leiomyosarcomas.

Embodied in this invention are compositions comprising polynucleotides with a therapeutically relevant genetic sequence as an active ingredient. The polynucleotides can comprise a portion of a sequence shown in any SEQ ID NOs: 1 to 10 and/or a portion of any sequence encoding at least 5 contiguous amino acids, preferably at least 10, more preferably at least 15, even more preferably 20, of any of the amino acid sequences of SEQ ID NOs: 147 to 154. This portion can comprise at least 10, preferably at least 15, more preferably at least 20, and even more preferably at least 30 contiguous nucleotides of any of the sequences of SEQ ID NOs:1 to 10, or the complementary strand thereof, or any nucleotide which can encode at least 10 contiguous amino acids of any of SEQ ID NOs:147 to 154. The polynucleotide can be administered, for example, to augment or attenuate the natural level of expression of TRRE within a target cell.

A polynucleotide for enhancing or attenuating TRRE expression can be introduced into cells as part of any suitable delivery vehicle known in the art. The polynucleotide can be administered to cells or injected into a tissue site as naked DNA, preferably in a supercoiled configuration. It is generally preferred to administer the polynucleotide as part of a composition that enhances expression in the target cell. Components of the composition can include those that protect the polynucleotide until delivery to the cell, enhance binding to or localization near target cells, enhance uptake or endocytosis into cells, promote translocation of the polynucleotide across the membrane into the cytoplasm, or enhance transport of the polynucleotide inside the cell to the site of action.

In one example, the composition comprises one half of a ligand-receptor binding pair, the other of which is present on the surface of the target cell. This can promote localization near the cell surface, endocytosis into the cell, or homing to the cell in vivo, or any combination thereof. Suitable components for including in the composition include, but are not limited to, antibodies or antibody fragments specific for the target tissue (for example, a tumor-associated antigen), integrins and integrin ligands optionally specific for the target tissue, and ligands for cytokine receptors on the target tissue. Where the object is to decrease TNF-R levels on the target cell by enhancing TRRE expression, a particularly preferred ligand is TNF itself. In this way, the composition will be focused towards cells with the phenotype to be treated, in preference to other cell types and cells already treated effectively.

In another example, the composition comprises a delivery vehicle that protects the polynucleotide and enhances its delivery into the cell. One type of suitable vehicle is a liposome that either encapsulates the polynucleotide, or (in the case of cationic liposomes) binds it by charge association. Another type of suitable vehicle is the capsid or envelope of a virus, defective viral particle, or synthetic viral particle, encapsidating or enveloping the polynucleotide. Preferred amongst such virally related particles are those that are tropic for the target tissue type, and comprise polypeptides (such as the influenza hemagglutinin) that promote fusion and delivery of the polynucleotide. The composition can also optionally comprise genetic elements of a virus that promotes replication of the therapeutic polynucleotide and/or integration into the genome of the target cell. Suitable viral systems for use with this invention include adenovirus vectors, retroviral vectors, adeno-associated viral vectors, sindbis virus vectors, and the like. Preferred are vectors that comprise viral genetic elements required in cis for packaging, the genetic elements required for replication or integration of the therapeutic polynucleotide, but not other viral genetic elements. Such vectors can be produced by packaging systems in which viral elements required only in trans are supplied by a host cell or second virus. See, e.g., Flotte et al. WO 95/13365.

It is often preferable to combine several such components and strategies into the composition with the therapeutic polynucleotide. For example, a polynucleotide can be enveloped in an adenovirus vector that expresses a targeting molecule like TNF as part of the viral package. The vector might alternatively express a coupling molecule, such as an avidin binding site, that can then be coupled with biotin-TNF for purposes of targeting to the target cell.

The following examples are meant to illustrate, but not limit, the claimed invention.

EXAMPLE 1

In Vitro TRRE Assay System

The objective of this study was to establish an assay system that measures TRRE activity on the human TNF-R in its native conformation integrated into the cell surface membrane. The transfected COS-1 cell line was chosen for the assay system since no background of endogenous p75 TNF-R was observed. Attempts to study and characterize the enzyme responsible for sTNF-R release have been difficult because the presence of an active form of the proteolytic enzyme is indicated only indirectly by the generation of soluble receptors. Studies of release of other membrane bound proteins as well as TNF-R have been carried out by measuring the levels of soluble counterparts by ELISA or by FACS analysis for the presence or absence of the surface antigens. Therefore, the level of the enzyme itself has not yet been quantitated. We therefore devised a novel assay system to detect and quantitate TRRE. It was found that the level of soluble forms released into the medium depends on the level of expression of surface antigens on the membrane and the rate at which the cells can synthesize more and express these proteins on the membrane. In some studies, the enzyme levels and the kinetics of active enzyme formed have been correlated with the levels of soluble forms released and the kinetics of their release. We have now devised a more defined assay system to detect and also quantitate TRRE specifically and enzymes that cleave membrane receptor proteins in general.

Membrane-associated TNF-R was chosen as the substrate for TRRE instead of the recombinant TNF-R molecule, because the membrane-associated TNF-R simulates a more physiological microenvironment and substrate for the evaluation of TRRE activity. Membrane-associated TNF-R can also assist in alleviating nonspecific cleavage by other proteases which can occur in nonmembrane-associated forms. Since most human cells express only extremely low levels of both TNF-Rs, human p75 TNF-R-overexpressing cells were constructed by cDNA transfection into monkey COS-1 cells which do not express either TNF-Rs.

The cDNA of the human p75 TNF-R was cloned from a λgt10 cDNA library derived from human monocytic U-937 cells (Clontech Laboratories, Palo Alto, Calif.). The cDNA was then subcloned into the EcoRI site of the mammalian expression vector pCDNA3 (Invitrogen, San Diego, Calif.) which contains the neomycin-resistance gene for the selection of transfected cells in the presence of G418. This construct was transfected into COS-1 cells using the calcium phosphate-DNA precipitation method described by Chen and Okayama. 24 hours post transfection, the transfected cells were placed in 600 μg/ml G418 (GIBCO BRL Life Technologies, Gaithersburg, Md.) for the selection of neomycin-resistant clones. The resistant cells were pooled and named C75R. These cells expressed approximately 70,000 receptors/cell by Scatchard analysis.

Figure 1:
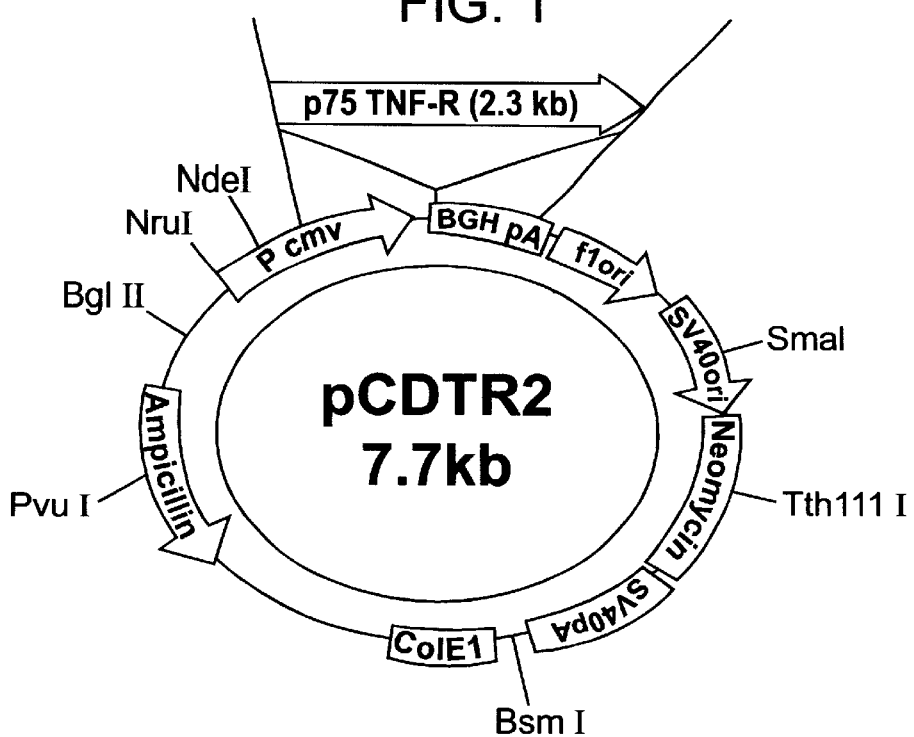
FIG. 1 is a schematic representation of plasmid pCDTR2 which expresses p75 TNF-R. PCMV stands for cytomegalovirus; BGHpA stands for bovine growth hormone polyadenylation signal.

The first 300 bp on both 5' and 3' ends of the cloned fragment was sequenced and compared to the reported cDNA sequence of human p75 TNF-R. The cloned sequence was a 2.3 kb fragment covering positions 58–2380 of the reported p75 TNF-R sequence, which encompasses the full length of the p75 TNF-R-coding sequence from positions 90–1475. The 2.3 kb p75 TNF-R cDNA was then subcloned into the multiple cloning site of the pCDNA3 eukaryotic expression vector. The orientation of the p75 TNF-R cDNA was verified by restriction endonuclease mapping. The final 7.7 kb construct, pCDTR2, carried the neomycin-resistance gene for the selection of transfected cells in G418, and the expression of the p75 TNF-R was driven by the cytomegalovirus promoter (FIG. 1). The pCDTR2 was then transfected into monkey kidney COS-1 cells using the calcium phosphate-DNA precipitation method. The selected clone in G418 medium, termed C75R, was identified and subcultured.

$^{125}$I was purchased from ICN Pharmaceuticals, Inc. (Costa Mesa, Calif.) and the human recombinant TNF was radiolabeled using the Chloramine-T method. To determine the level of p75 TNF-R expression on C75R cells, $2\times10^5$ cells/well were plated into a 24-well culture plate and incubated for 12 to 16 hours in 5% $CO_2$ at 37° C. They were then incubated with 2–30 ng $^{125}$I radiolabeled human recombinant TNF in the presence or absence of 100-fold excess of unlabeled human TNF at 4° C. for 2 hours. After three washes with ice-cold PBS, cells were lysed with 0.1N NaOH and radioactivity was determined in a Pharmacia Clini-gamma counter (Uppsala, Sweden). To determine the effect of TRRE on the surface levels of p75 TNF-R, cells were incubated with or without the TRRE-containing supernatant for 30 min at 37° C., and then the medium was aspirated before incubation with radiolabeled TNF.

Soluble p75 TNF-R was generated from C75R cells by incubation with TRRE-containing supernatant. After a 30 min incubation, the supernatant was collected and centrifugally concentrated with Centriprep-10 filter (10,000 MW cut-off membrane) (Amicon, Beverly, Mass.) and applied to 10% acrylamide SDS-PAGE. The proteins were then electrophoretically transferred to a polyvinylidene difluoride membrane (Immobilon) (Millipore, Bedford, Mass.). Immunostaining was performed using the biotin-streptavidin system (Amersham, Amersham, UK) and the peroxidase substrate kit DAB (Vector Laboratories, Burlingame, Calif.).

Figure 2:
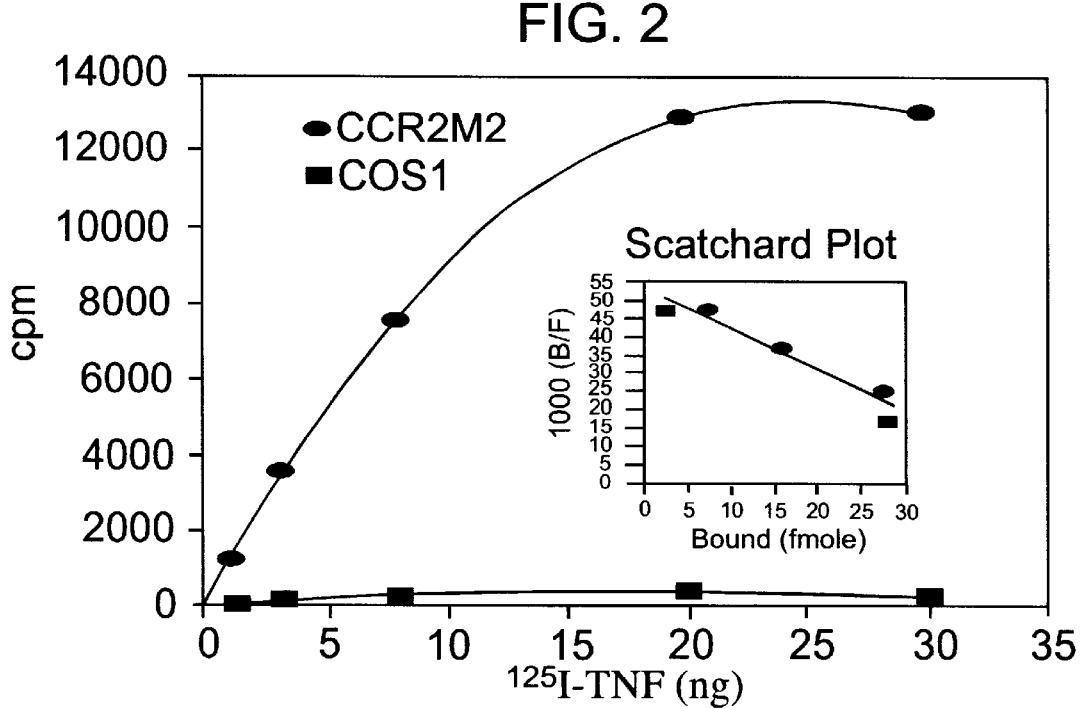
FIG. 2 is a graph depicting the results of measurement of p75 TNF-R on transfected COS-1 cells (C75R) by the method described herein. The results obtained with the C75R cells (●) is compared to that obtained with that from the parental COS-1 cells (■). The receptor number was calculated from a Scatchard plot (inset).

The results obtained are shown in FIG. 2, C75R had a very high level of specific binding of radiolabeled $^{125}$I-TNF, while parental COS-1 cells did not. The number of TNF-R expressed on C75R was determined to be 60,000–70,000 receptors/cell by Scatchard analysis (FIG. 2, inset). The level of TNF-R expression in this clone was 40 to 50 times higher than that of THP-1 cells. The Kd value calculated from the TNF binding assay of C75R was $5.6\times10^{-10}$ M. This Kd value was in close agreement to the values previously reported for native p75 TNF-R. Thus, transfected COS-1 cells expressed high levels of human p75 TNF-R in a form that appeared to be similar to native TNF-R.

In order to measure the effect of TRRE on membrane-bound TNF-R, the following experiment was performed. C75R cells were seeded at a density of $2\times10^5$ cells/well in a 24-well cell culture plate and incubated for 12 to 16 hours at 37° C. in 5% $CO_2$. The medium in the wells was aspirated, replaced with fresh medium alone or with TRRE medium, and incubated for 30 min at 37° C. Throughout the examples, the "TRRE-medium" was that collected by stimulation of THP-1 cells with PMA followed by incubation of the cells in fresh medium for 2 hours as described. After this incubation, the medium was replaced with fresh medium containing 30 ng/ml $^{125}$I-labeled TNF. After 2 hours at 4° C., the cells were lysed with 0.1 N NaOH and the level of bound radioactivity was measured. The level of specific binding of C75R by $^{125}$I-TNF was significantly decreased after incubation with TRRE. The radioactive count was 1,393 cpm on the cells incubated with TRRE compared to 10,567 cpm on the cells not treated with TRRE, a loss of 87% of binding capacity.

Figure 3:
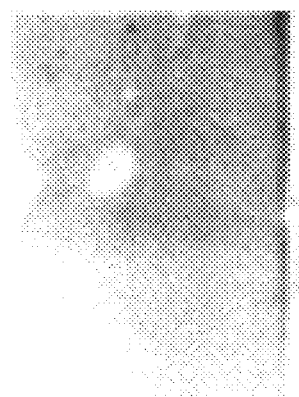
FIG. 3 depicts the results of Western Blot analysis of soluble receptors released from C75R cells by TRRE.

In order to determine the size of the p75 TNF-R cleared from C75R by TRRE, the following experiment was performed. $15\times10^6$ C75R cells were seeded in a 150 mm cell culture plate and incubated at 37° C. in 5% $CO_2$ for 12 to 16 hours. TRRE medium was incubated with C75R cells in the 150 mm plate for 30 min and the resulting supernatant was collected and centrifuged. The concentrated sample was applied to 10% acrylamide SDS-PAGE and electrophoretically transferred to a polyvinylidene difluoride membrane (Immobilon). Immunostaining resulted in a single band of 40 kDa, similar to the size found in biological fluids (FIG. 3).

The following method and assay were used throughout the Examples to measure TRRE activity. C75R cells and COS-1 cells were seeded into 24-well culture plates at a density of $2.5\times10^5$ cells/ml/well and incubated overnight (for 12 to 16 hours) in 5% $CO_2$ at 37° C. After aspirating the medium in the well, 300 µl of TRRE medium was incubated in each well of both the C75R and COS-1 plates for 30 min in 5% $CO_2$ at 37° C. (corresponding to A and C mentioned below, respectively). Simultaneously, C75R cells in 24-well plates were also incubated with 300 µl of fresh medium or buffer (corresponding to B mentioned below). The supernatants were collected, centrifuged, and then assayed for the concentration of soluble p75 TNF-R by ELISA as described above.

The following values were assigned and calculations made. A=(amount of soluble p75 TNF-R in a C75R plate treated with the TRRE containing sample); i.e. the total amount of sTNF-R in a C75R plate. B=(amount of soluble p75 TNF-R spontaneously released in a C75R plate treated with only medium or buffer containing the same reagent as the corresponding samples but without exogenous TRRE); i.e. the spontaneous release of sTNF-R from C75R cells. C=(amount of soluble p75 TNF-R in a COS-1 plate treated with the TRRE sample or the background level of soluble p75 TNF-R released by THP-1.); i.e. the degraded value of transferred (pre-existing) sTNF-R in the TRRE sample during 30 min incubation in a COS-1 plate. This corresponds to the background level of sTNF-R degraded in a C75R plate.

The net release of soluble p75 TNF-R produced only by TRRE activity existing in the initial sample is calculated as follows: (Net release of soluble p75 TNF-R only by TRRE)= A−B−C. We assigned the net release value of soluble p75 TNF-R as the amount of TRRE activity and defined 1 pg of soluble p75 TNF-R net release (A−B−C) as one unit (U) of TRRE activity.

Once the TRRE assay was devised, the time course of receptor shedding was assayed by the following method. TRRE-medium was incubated with C75R and COS-1 cells for varying lengths of time between 5 and 90 min. The supernatants were then collected and assayed for the level of soluble p75 TNF-R by ELISA and the net TRRE activity was calculated as described above. Detectable levels of soluble receptor were released by TRRE within 5 min and increased up to 30 min (FIG. 4A). Subsequent experiments with longer incubation times showed that the level of TRRE remained relatively constant after 30 min, presumably from the depletion of substrates (FIG. 4B). Therefore, 30 min was determined to be the optimal incubation time for this assay system.

The binding assay clearly showed that the parental COS-1 cells did not bind human $^{125}$I-TNF, whereas the transfected C75R cells showed strong specific binding. Scatchard analysis indicated receptor levels of 70,000 per cell which were 40 to 50 times higher than that typically found on other cell lines. This higher level of substrate allowed detection of TRRE activity with much more sensitivity than with other cell lines. The Kd value calculated from Scatchard analysis was $5.6 \times 10^{-10}$ M, similar to the values previously reported for the native human p75 TNF-R. Thus, the transfected cells provided the membrane form of the receptor in its native configuration, resulting in an excellent source of substrate.

When C75R cells were incubated with TRRE medium, soluble p75 TNF-R was released into the supernatant which was measurable by ELISA. The amount of receptors released corresponded to level of TRRE activity. As C75R cells were incubated with TRRE medium, another well of C75R cells was simultaneously incubated with medium or buffer alone to measure the level of spontaneous release by C75R. The spontaneous release can be due to an endogenous source of proteolytic enzyme, a homolog of the human TRRE of monkey origin. In addition, TRRE medium was incubated with the parent COS-1 cells to detect the level of soluble receptors that was pre-existing in the sample. For this purpose, rather than directly measuring the level of soluble receptors in the supernatant by ELISA, we incubated the sample with COS-1 cells because we found that after incubation for 30 min with COS-1 cells, significant degradation of the soluble receptors was observed. The level of initial soluble receptors in the supernatant may decrease up to 50% after a 30 min incubation with COS-1 cells. Incorporating these two sources of background soluble receptors was the most accurate way to calculate the net TRRE activity.

The premise that increase in the level of soluble receptors in the supernatant was due to the proteolytic cleavage of membrane bound receptors was also supported by the loss of binding of $^{125}$I-labeled TNF to C75R cells after incubation with TRRE. Since the receptor generated by TRRE was similar in size to that found in biological fluids, this reinforced the finding that TRRE generates sTNF-R in vivo.

The induction patterns of TRRE and known MMPs by PMA stimulation are quite different. In order to induce MMPs, monocytic U-937 cells, fibrosarcoma HT-1080 cells, or peritoneal exudate macrophages (PEM) usually have to be stimulated for one to three days with LPS or PMA. On the other hand, as compared with this prolonged induction, TRRE is released very quickly in culture supernatant following 30 min of PMA-stimulation. As disclosed in Example 2, TRRE is stored in the cell very close to the cell membrane to be secreted immediately by PMA-stimulation, and TRRE is synthesized very quickly within 2 hours also by PMA-stimulation. Therefore, judging from zymography gel data and the different induction patterns by PMA, TRRE cannot be classified into one of the pre-existing MMP families, despite their resemblance regarding metal-requirement and involvement of serine proteases in their activation.

Soluble TNF-R has been shown to bind to TNF or LT and form a complex consisting of 3 sTNF-R with 3 TNF or LT. Banner et al. (1993). According to gel filtration analysis presented above, the profile of TRRE and soluble p75 TNF-R was quite similar, with both peaks approximately at 150 kDa. Since the molecular size of soluble p75 TNF-R was reported to be 40 kDa, this suggests that sTNF-R exist as a complex formed with TRRE or TNF, or otherwise as homo oligomers. The hypothesis that TRRE and sTNF-R form a complex in vitro was confirmed by the experiment that 25% TRRE activity was recovered from soluble p75 TNF-R affinity column. This means that free TRRE has the ability to bind to its catalytic product, sTNF-R. The remaining 75% which did not combine to the affinity column may already be bound to sTNF-R or may not have enough affinity to bind to sTNF-R even though it is in a free form.

Although a considerable amount of enzyme product (EP) complex is thought to exist in the reacting solution, TRRE retained 86% of its activity after treated once with excessive substrate, suggesting that this complex can be easily separated when it meets new substrate. This EP complex does not seem to inhibit the enzymatic reaction of TRRE significantly. While sTNF-R is a potent inhibitor against the biological activities of TNF and LT, it was also shown that sTNF-R has another role in stabilizing TNF activity in vitro. Aderka et al. (1992) *J. Exp. Med.* 175:323–329. Thus sTNF-R might act as a stabilizer not only for TNF, but also for TRRE by composing complex formation. This EP complex between TRRE and sTNF-R may be formed presumably under in vitro conditions, however it is possible that TRRE, sTNF-R and TNF make up several types of complexes in vivo as well as in vitro, and therefore may have physiological significance.

EXAMPLE 2

Biological Effect of TRRE

In this Example, the effect and biological significance of TRRE is investigated, including (a) substrate specificity and (b) function in vitro.

Fluorescein isothiocyanate (FITC)-conjugated anti-CD54, FITC-conjugated goat anti-rabbit and mouse antibodies, mouse monoclonal anti-CD30, anti-CD11b and anti-IL-1R (Serotec, Washington D.C.) were utilized in this study. Rabbit polyclonal anti-p55 and p75 TNF-R were constructed according to the method described by Yamamoto et al. (1978) *Cell Immunol.* 38:403–416. THP-1 cells were treated for 30 min with 1,000 and/or 5,000 U/ml of TRRE eluted from the DEAE-Sephadex column and transferred to 12×75 mm polystyrene tubes (Fischer Scientific, Pittsburgh, Pa.) at $1 \times 10^5$ cells/100 µl/tube. The cells were then pelleted by centrifugation at 350×g for 5 min at 4° C. and stained directly with 10 µl FITC-conjugated anti-CD54 (diluted in cold PBS/0.5% sodium aside), indirectly with FITC-conjugated anti-mouse antibody after treatment of mouse monoclonal anti-CD11b, IL-1R and CD30 and also indirectly with FITC-conjugated anti-rabbit antibody after treatment of rabbit polyclonal anti-p55 and p75 TNF-R.

THP-1 cells stained with each of the antibodies without treatment of TRRE were utilized as negative controls. The tubes were incubated for 45 min at 4° C., agitated every 15 min, washed twice with PBS/2%FCS, repelleted and then resuspended in 200 µl of 1% paraformaldehyde. These labeled THP-1 cells were analyzed using a fluorescence activated cell sorter (FACS) (Becton-Dickinson, San Jose, Calif.) with a 15 mW argon laser with an excitation of 488 nm. Fluorescent signals were gated on the basis of forward and right angle light scattering to eliminate dead cells and aggregates from analysis. Gated signals ($10^4$) were detected at 585 BP filter and analyzed using Lysis II software. Values were expressed as percentage of positive cells, which was calculated by dividing mean channel fluorescence intensity (MFI) of stained THP-1 cells treated with TRRE by the MFI of the cells without TRRE treatment (negative control cells).

In order to test the in vitro TNF cytolytic assay by TRRE treatment the L929 cytolytic assay was performed according to the method described by Gatanaga et al. (1990b). Briefly, L929 cells, an adherent murine fibroblast cell line, were plated (70,000 cells/0.1 ml/well in a 96-well plate) overnight. Monolayered L929 cells were pretreated for 30 min with 100, 500 or 2,500 U/ml of partially-purified TRRE and then exposed to serial dilutions of recombinant human TNF for 1 hour. After washing the plate with RPMI-1640 with 10% FCS to remove the TRRE and TNF, the cells were incubated for 18 hours in RPMI-1640 with 10% FCS containing 1 µg/ml actinomycin D at 37° C. in 5% $CO_2$. Culture supernatants were then aspirated and 50 µl of 1% crystal violet solution was added to each well. The plates were incubated for 15 min at room temperature. After the plates were washed with tap water and air-dried, the cells stained with crystal violet were lysed by 100 µl per well of 100 mM HCl in methanol. The absorbance at 550 nm was measured using an EAR 400 AT plate reader (SLT-Labinstruments, Salzburg, Austria).

Figure 4:
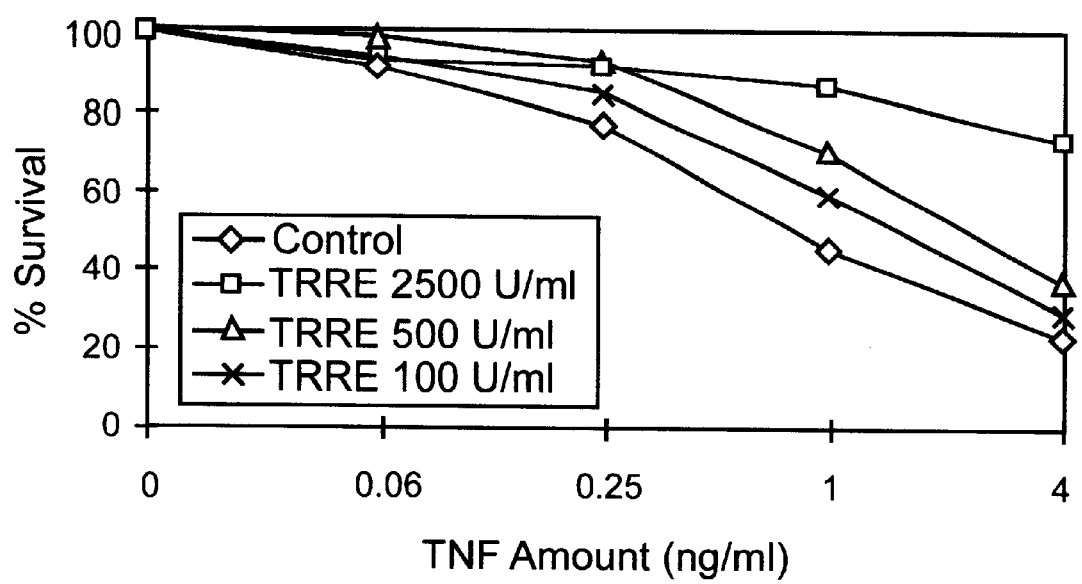
FIG. 4 is a graph depicting the results of a modified in vitro TNF cytolytic assay by TRRE treatment to L929 cells.

TRRE was originally defined as a protease which truncated the human p75 TNF-R that was overexpressed on cDNA-transduced COS-1 cells (C75R). To investigate whether TRRE may truncate not only p75 but also p55 TNF-R on human cells, partially-purified TRRE from human THP-1 cells was applied to THP-1 cells which express low levels of both p55 and p75 TNF-R (approximately 1,500 receptors/cell by Scatchard analysis, data not shown). TRRE eluate from the DEAE-Sephadex column was added to THP-1 cells ($5 \times 10^6$ cells/ml) at a final TRRE concentration of 1,000 U/ml for 30 min. The concentration of soluble p55 and p75 TNF-R in that supernatant was measured by soluble p55 and p75 TNF-R ELISA. TRRE was found to truncate both human p55 and p75 TNF-R on THP-1 cells and released 2,382 and 1,662 pg/ml soluble p55 and p75 TNF-R, respectively (FIG. 4). Therefore, TRRE was capable of truncating human p75 TNF-R on C75R cells and both human p55 and p75 TNF-R on THP-1 cells.

EXAMPLE 3

Use of TRRE in Treating Septic Shock

The following protocol was followed to test the effects of TRRE in preventing mortality in test animals which were treated with lipopolysaccharides (LPS) to induce sepsis and septic shock.

Generally, mice were injected with lethal or sublethal levels of LPS, and then with a control buffer or TRRE. Samples of peripheral blood were then collected at intervals to establish if TRRE blocked TNF-induced production of other cytokines in the bloodstream. Animals were assessed grossly for the ability of TRRE to block the clinical effects of shock and then euthanized and tissues examined by histopathological methods.

More specifically, adult Balb/c mice, the traditional animal model for septic shock studies [see, for example, Mack et al. (1997) *J. Surg. Res.* 69:399–407; and Seljelid et al. (1997) *Scand. J. Immunol.* 45:683–7], were placed in a restraining device and injected intravenously via the tail vein with a 0.1 ml solution containing 10 ng to 10 mg of LPS in phosphate buffer saline (PBS). These levels of LPS induce mild to lethal levels of shock in this strain of mice. Shock results from changes in vascular permeability, fluid loss, and dehydration, and is often accompanied by symptoms including lethargy, a hunched, stationary position, rumpled fur, cessation of eating, cyanosis, and, in serious cases, death within 12 to 24 hours. Control mice received an injection of PBS. Different amounts (2,000 or 4,000 U) of purified human TRRE were injected IV in a 0.1 ml volume within an hour prior to or after LPS injection. Serum (0.1 ml) was collected with a 27 gauge needle and 1 ml syringe IV from the tail vein at 30, 60 and 90 minutes after LPS injection. This serum was heparinized and stored frozen at −20° C. Samples from multiple experiments were tested by ELISA for the presence of sTNF-R, TNF, IL-8 and IL-6. Animals were monitored over the next 12 hours for the clinical effects of shock. Selected animals were euthanized at periods from 3 to 12 hours after treatment, autopsied and various organs and tissues fixed in formalin, imbedded in paraffin, sectioned and stained by hematoxalin-eosin (H and E). Tissue sections were subjected to histopathologic and immunopathologic examination.

Figure 5:
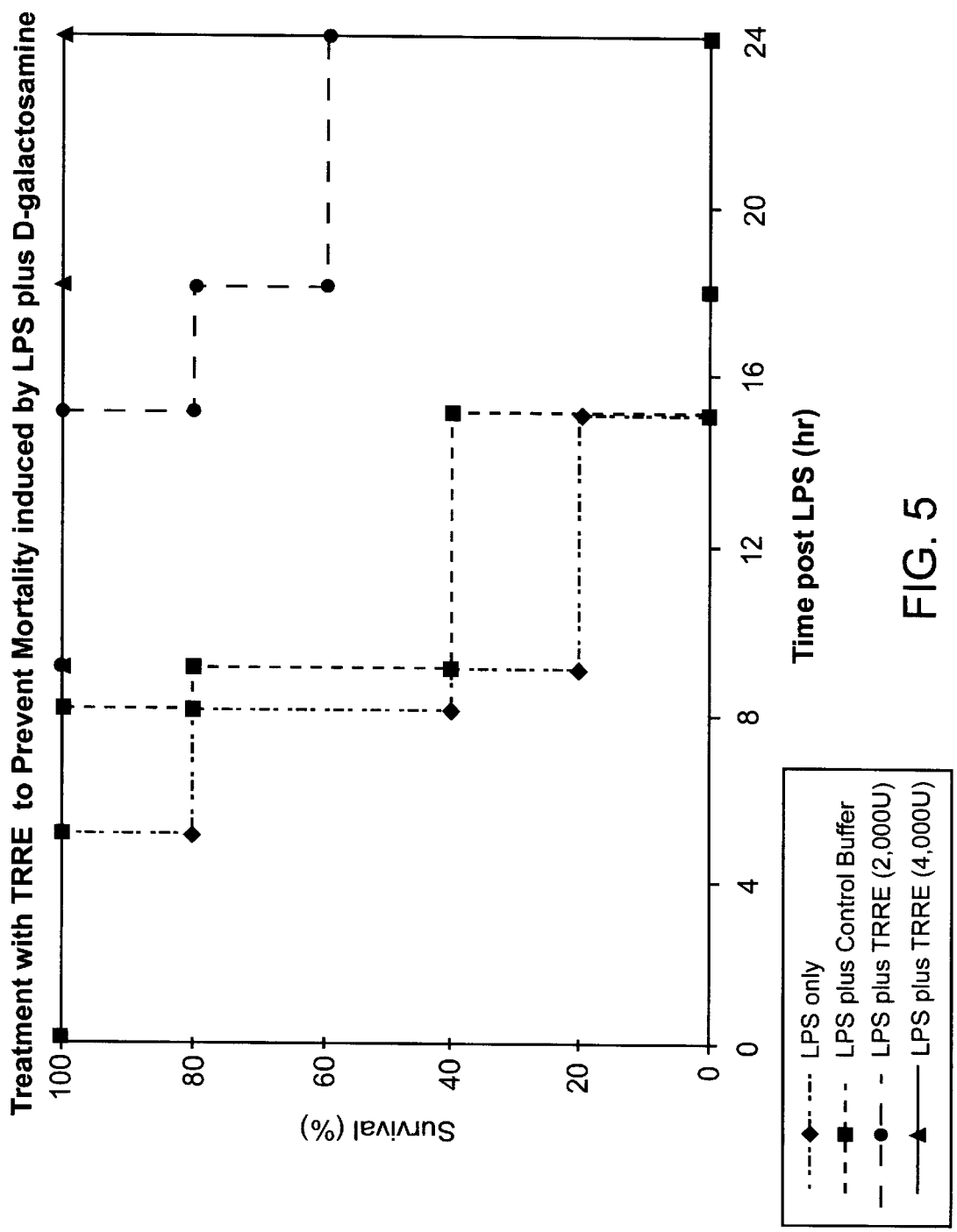
FIG. 5 is a graph depicting the effect of TRRE on preventing mortality in mice treated with lipopolysaccharide (LPS) to induce septic peritonitis.

As shown in FIG. 5, mice injected with LPS alone or LPS and a control buffer demonstrated rapid mortality. 50% of the test animals were dead after 8 hours (LPS) or 9 hours (LPS plus control buffer), and 100% of the animals were dead at 15 hours. In contrast, when injections of LPS were accompanied by injections of a 2,000 U of TRRE, death was delayed and death rates were lower. Only 40% of the animals were dead at 24 hours. When 4,000 U of TRRE was injected along with LPS, all of the animals had survived at 24 hours. Thus, TRRE is able to counteract the mortality induced by LPS in test animals.

EXAMPLE 4

Effect of TRRE on the Necrotizing Activity of Human TNF in Vivo

The following protocol was followed to test the effects of TRRE in affecting tumor necrosis in test animals in which tumors were produced, and in which TNF was subsequently injected.

Generally, on Day 0, cutaneous Meth A tumors were produced on the abdominal wall of fifteen BALB/c mice by intradermal injection of $2 \times 20^5$ Meth A tumor cells.

On Day 7, the mice were divided into three groups of five mice each and treated as follows:

Group 1: Injected intravenously with TNF (1 µg/mouse).

Group 2: Injected intravenously with TNF (1 µg/mouse) and injected intratumorally with TRRE (400 units/mouse, 6, 12 hours after TNF injection).

Group 3: Injected intravenously with TNF (1 µg/mouse) and injected intratumorally with control medium (6, 12 hours after TNF injection).

On Day 8, tumor necrosis was measured with the following results:

| | % of necrosis |
|---|---|
| Group 1: | 100 (5/5) |
| Group 2: | 20 (1/5) |
| Group 3: | 80 (4/5) |

Therefore, injections of TRRE greatly reduced the ability of TNF to induce necrosis in Meth A tumors in BALB/c mice.

EXAMPLE 5

Clones Involved in TRRE Activity

Nine clones involved in TRRE activity were obtained and designated clones 2-8, 2-9, 2-14, 2-15, P2-2, P2-10, P2-13, P2-14, and P2-15; the DNA sequences represented by SEQ ID NOs:1 to 10, with partial sequences of clone 2–8 represented by SEQ ID NOs:2 and 3. While not wishing to be bound by any particular theory, the inventors suggest that none of these clones encodes the TRRE itself, but these clones may be templates for RNAs or encode proteins involved in TRRE expression or function.

1. Obtaining Clones Involved in TRRE Activity

Clones 2-8, 2-9, 2-14, 2-15, P2-2, P2-10, P2-13, P2-14, and P2-15 (represented by SEQ ID NOs:1 to 10) were selected from a library of $10^6$ Jurkat T cell (ATCC #TIB-152) cDNA inserts in the ZAP Express™/EcoRI vector (catalog no. 938201, Stratagene, La Jolla, Calif.). Jurkat cells have a high TRRE activity (850 TRRE U/ml at $10^{-7}$M PMA). The library was divided into 48 groups of DNA and transformed into COS-1 cells, which normally lack TRRE activity. Once these cells were grown out, the TRRE assay (described above) was performed, and five positive groups selected. DNA from each of these five groups and transfected into E. coli, with 15 plates per group. DNA was prepared from these cells and then transfected again into COS-1 cells. Again, once the cells were grown out, the TRRE activity was tested. Two positive groups were selected and transfected into E. coli, yielding 98 colonies. DNA was prepared from 96 of these colonies and transfected into COS-1 cells. The TRRE assay was performed again, and nine positive clones selected that substantially increased TRRE activity. These clones were designated 2-8, 2-9, 2-14, 2-15, P2-2, P2-10, P2-13, P2-14, and P2-15. The Production of TRRE activity from these clones is demonstrated in FIG. 6. This figure shows that each clone is able to substantially increase (by 85% to 130%) TRRE activity compared to the control.

These nine clones were then sequenced. The strategy used to sequence the inserts in the clones included a combination of procedures which are summarized below:

1. Plasmid DNA was prepared using a modified alkaline lysis procedure.
2. DNA sequencing was performed using DyeDeoxy termination reactions (ABI). Base-specific fluorescent dyes were used as labels.
3. Sequencing reactions were analyzed on 5.75% Long Ranger™ gels by an ABI 373A-S or on 5.0% Long Ranger™ M gels by an ABI 377 automated sequencer.
4. Subsequent data analysis was performed using Sequencher™ 3.0 software.
5. Standard primers T7X, T3X, -40, -48 Reverse, and BK Reverse (BKR) were used in sequencing reactions. For each clone, several additional internal sequencing primers (listed below) were synthesized.

The sequence alignment printout reports generated using Sequencher™ 3.0 software and edited by hand are presented below.

NCBI BLAST (Basic Local Alignment Search Tool) sequence analysis [Altschul et al. (1990) J. Mol. Biol. 215:403–410] was performed to determine if any known sequences were significantly similar to these sequences. Both the DNA sequences of the clones and the corresponding ORFs (if any) were compared to sequences available in databases.

The following clones were obtained and sequenced:

| Clone | Sequence Designation | Length (bp) | Homology | SEQ ID NO: |
|---|---|---|---|---|
| 2-9 | AIM2 | 4,047 | novel | 1 |
| 2-8* | AIM3T3 | 739 | similar to M. musculus 45S pre-rRNA gene | 2 |
|  | AIM3T7 | 233 | novel | 3 |
| 2-14 | AIM4 | 2,998 | human arfaptin 2 | 4 |
| 2-15 | AIM5 | 4,152 | novel | 5 |
| P2-2 | AIM6 | 3,117 | novel | 6 |
| P2-10 | AIM7 | 3,306 | Human Insulin-like Growth factor II Receptor | 7 |
| P1-13 | AIM8 | 4,218 | novel | 8 |
| P2-14 | AIM9 | 1,187 | novel | 9 |
| P2-15 | AIM10 | 3,306 | novel | 10 |

*Clone 2-8 (AIM3) was only partially sequenced, generating two partial sequences of 739 and 233 bp, designated AIM3T3 and AIM3T7, respectively.

2. Clone 2-9 (AIM2)

The internal sequencing primers synthesized and used to obtain the sequence of this clone were:

|  |  |  | SEQ ID NO: |
|---|---|---|---|
| AIM2 | AP1 | 5' TGC GGG GCC AGA GTG GGC TG 3' | 11 |
| AIM2 | AP2 | 5' GCA GTC CTG GCC TGC GGA TG 3' | 12 |
| AIM2 | AP3 | 5' GTC GAC AGG AGA ATT GGT TC 3' | 13 |
| AIM2 | AP4 | 5' GCC TGG GTT CGG TGC GGG AC 3' | 14 |
| AIM2 | AP5 | 5' TGG TCG GGT GTT TGT GAG TG 3' | 15 |
| AIM2 | AP6 | 5' CCT CTT CCG TCT CCT CAG TG 3' | 16 |
| AIM2 | AP7 | 5' GGA TTG CTA GTC TCA CAG AC 3' | 17 |
| AIM2 | AP8 | 5' TTA AGG GTG GCT GAA GGG AC 3' | 18 |
| AIM2 | AP9 | 5' ACC TTC CCT CCC TGT CAC AG 3' | 19 |
| AIM2 | AP10 | 5' TGG TCG GGT GTT TGT GAG TG 3' | 20 |
| AIM2 | AP11 | 5' ACA CCA TTC CAG AAA TTC AG 3' | 21 |
| AIM2 | AP12 | 5' AAA CTG CAG GTG GCT GAG TC 3' | 22 |
| AIM2 | AP13 | 5' GTC CTA ATG TTT TCA GGG AG 3' | 23 |
| AIM2 | AP14 | 5' AAA ACC TAT GGT TAC AAT TC 3' | 24 |
| AIM2 | AP15 | 5' TCC TAG ACA TGG TTC AAG TG 3' | 25 |
| AIM2 | AP16 | 5' GAT ATA ATT AGT TCT CCA TC 3' | 26 |
| AIM2 | AP17 | 5' ATG CCT GTT CCA GGC TGC AC 3' | 27 |
| AIM2 | AP18 | 5' GGA CGG CGA CCT CCA CCC AC 3' | 28 |
| AIM2 | AP19 | 5' GGG CTC CTC CGA CGC CTG AG 3' | 29 |
| AIM2 | AP20 | 5' AGT CTA GCC CTG GCC TTG AC 3' | 30 |
| AIM2 | AP21 | 5' GTC ACT GGG GAC TCC GGC AG 3' | 31 |
| AIM2 | AP22 | 5' CAG CTT TCC CTG GGC ACA TG 3' | 32 |
| AIM2 | AP23 | 5' CAC AGC TGT CTC AAG CCC AG 3' | 33 |
| AIM2 | AP24 | 5' ACT GTT CCC CCT ACA TGA TG 3' | 34 |
| AIM2 | AP25 | 5' ATC ATA TCC TCT TGC TGG TC 3' | 35 |
| AIM2 | AP26 | 5' GTT CCC AGA GCT TGT CTG TG 3' | 36 |
| AIM2 | AP27 | 5' GTT TGG CAG ACT CAT AGT TG 3' | 37 |
| AIM2 | AP28 | 5' TAG CAG GGA GCC ATG ACC TG 3' | 38 |

The sequence of AIM2 is presented in SEQ ID NO:1. The complementary strand of the AIM2 sequence is SEQ ID NO:147. The longest ORF in the AIM2 sequence is 474 AA long and represented in SEQ ID NO:148.

The BLAST search did not reveal any sequences with significant similarity to the AIM2 sequence.

3. Clone 2-8 (AIM3)

Of all the clones obtained, only this clone was not sequenced in its entirety. Two partial sequences of length 739 and 233 were obtained and designated AIM3T3 and AIM3T7. The internal sequencing primers synthesized and used to obtain the sequence of this clone were:

| | | | SEQ ID NO: |
|---|---|---|---|
| AIM3 | AP1 | 5' CTT GGC GCC AGA AGC GAG AG 3' | 39 |
| AIM3 | AP2 | 5' CCT CTC TCT CTC TCT CTC TC 3' | 40 |
| AIM3 | AP3 | 5' TCC CCG CTG ATT CCG CCA AG 3' | 41 |
| AIM3 | AP4 | 5' CTT TTT GAA TTC GGC ACG AG 3' | 42 |
| AIM3 | AP5 | 5' CCC CTG GTC CGC ACC AGT TC 3' | 43 |
| AIM3 | AP6 | 5' GAG AAG GGT CGG GGC GGC AG 3' | 44 |
| AIM3 | AP7 | 5' AAA TCA CAT CGC GTC AAC AC 3' | 45 |
| AIM3 | AP8 | 5' TAA GAG AGT CAT AGT TAC TC 3' | 46 |

The sequences of AIM3T3 and AIM3T7 are presented in SEQ ID NOs:2 and 3, respectively. The BLAST search revealed that the AIM3T3 sequence may be homologous to the mouse (*M. musculus*) 28S ribosomal RNA [Hassouna et al. (1984) *Nucleic Acids Res.* 12:3563–3583] and the *M. musculus* 45S pre-rRNA genes [Accession No. X82564, Goegel et al., *Chromosoma*, in press]. The complementary sequence of the AIM3T3 sequence showed 99% similarity over 408 bp beginning with nt 221 of SEQ ID NO:2 to the former and 97% similarity over the same span to the latter.

The BLAST search did not reveal any known sequence homologous to the AIM3T7 sequence.

4. Clone 2-14 (AIM4)

The internal sequencing primers synthesized and used to obtain the sequence of this clone were:

| | | | SEQ ID NO: |
|---|---|---|---|
| AIM4 | AP1 | 5' GCT CTA GAA GTA CTC TCG AG 3' | 47 |
| AIM4 | AP2 | 5' ACT CTG GCC ATC AGG AGA TC 3' | 48 |
| AIM4 | AP3 | 5' CAG GCG TTG TAG ATG TTC TG 3' | 49 |
| AIM4 | AP4 | 5' AGT GGC AGG CAG AAG TAA TG 3' | 50 |
| AIM4 | AP5 | 5' GGT TGG AGA ACT GGA TGT AG 3' | 51 |
| AIM4 | AP6 | 5' CTA TTC AGA TGC AAC GCC AG 3' | 52 |
| AIM4 | AP7 | 5' CCA TGG CAC ACA GAG CAG AC 3' | 53 |
| AIM4 | AP8 | 5' GCT ACC ATG CAG AGA CAC AG 3' | 54 |
| AIM4 | AP9 | 5' CAG GCT GAC AAG AAA ATC AG 3' | 55 |
| AIM4 | AP10 | 5' GGC ACG CAT AGA GGA GAG AC 3' | 56 |
| AIM4 | AP11 | 5' TGG GTG ATG CCT TTG CTG AC 3' | 57 |
| AIM4 | AP12 | 5' AAA ACA AGA TCA AGG TGA TG 3' | 58 |
| AIM4 | AP13 | 5' TTG CCC ACA TTG CTA TGG TG 3' | 59 |
| AIM4 | AP14 | 5' GAC CAA GAT CAG AAG TAG AG 3' | 60 |
| AIM4 | AP15 | 5' CCC CTG GGC CAA TGA TGT TG 3' | 61 |
| AIM4 | AP16 | 5' TCT TCC CAC CAT AGC AAT G 3' | 62 |
| AIM4 | AP17 | 5' TGG TCT TGG TGA CCA ATG TG 3' | 63 |
| AIM4 | AP18 | 5' ACA CCT CGG TGA CCC CTG TG 3' | 64 |
| AIM4 | AP19 | 5' TCT CCA AGT TCG GCA CAG TG 3' | 65 |

The sequence of AIM4 is presented in SEQ ID NO:4.

The complementary strand of the AIM4 sequence is SEQ ID NO:149. The longest ORF in the AIM4 sequence is 236 AA long and represented in SEQ ID NO:150.

The BLAST search revealed that this clone may be homologous or identical to the human arfaptin 2, putative target protein of ADP-ribosylation factor (GENBANK locus HSU52522, accession U52522).

5. Clone 2-15 (AIM5)

The internal sequencing primers synthesized and used to obtain the sequence of this clone were:

| | | | SEQ ID NO: |
|---|---|---|---|
| AIM5 | AP1 | 5' ACA TGG GCT GCA CTC ACG AC 3' | 66 |
| AIM5 | AP2 | 5' GAT CCT CTG AAC CTG CAG AG 3' | 67 |
| AIM5 | AP3 | 5' GGA AAT GAG GTG GGG CGA TC 3' | 68 |
| AIM5 | AP4 | 5' CTT TGC CTT GGA CAA GGA TG 3' | 69 |
| AIM5 | AP5 | 5' GCA CCT GCC ATT GGG GGT AG 3' | 70 |
| AIM5 | AP6 | 5' GGT GGA AGC CAT TGA CGG TG 3' | 71 |
| AIM5 | AP7 | 5' TGC GTC TCT CGT CGC TGC TG 3' | 72 |
| AIM5 | AP8 | 5' GCG GAA ACT CTG TGG TGC TG 3' | 73 |
| AIM5 | AP9 | 5' AGG ATT GCC TTC CTC TAC TG 3' | 74 |
| AIM5 | AP10 | 5' TGT CTG TTT CAC CAG GGC AG 3' | 75 |
| AIM5 | AP11 | 5' CCA GTG CCT CTA TGC ATG TC 3' | 76 |
| AIM5 | AP12 | 5' AGG AAG CCC ACG CAC ACC AC 3' | 77 |
| AIM5 | AP13 | 5' CCC TTT GTT CCC TGA TCT TC 3' | 78 |
| AIM5 | AP14 | 5' CGC TCG GGA TCC AGG TCA TC 3' | 79 |
| AIM5 | AP15 | 5' TCG AGG TTC AGA GCG TAG TG 3' | 80 |

The sequence of AIM5 is presented in SEQ ID NO:5.

The BLAST search revealed that the AIM5 sequence is novel. However, it displays some similarity, but not complete similarity, to Human Initiation Factor 5A (eIF-5A) [Koettnitz et al. (1995) *Gene* 159:283–284] and Human Initiation Factor 4D (eIF 4D) [Smit-McBride et al. (1989) *J. Biol. Chem.* 264:1578–1583].

6. Clone P2-2 (AIM6)

The internal sequencing primers synthesized and used to obtain the sequence of this clone were:

| | | | SEQ ID NO: |
|---|---|---|---|
| AIM6 | AP1 | 5' TCT TGG ATC TCT GGC ACC TC 3' | 81 |
| AIM6 | AP2 | 5' CCA TCA GAG TGA AGG AGG AG 3' | 82 |
| AIM6 | AP3 | 5' CCA TCT TCC ACT GGT CAG AG 3' | 83 |
| AIM6 | AP4 | 5' CTC CTT CTC TTG GAT CTC TG 3' | 84 |
| AIM6 | AP5 | 5' TTA CTT CAG CAC TGT TAG TC 3' | 85 |
| AIM6 | AP6 | 5' AGG GAG GTA GCT CAA AGC TC 3' | 86 |
| AIM6 | AP7 | 5' TGG GTC CAC AGT TCG CAC AG 3' | 87 |
| AIM6 | AP8 | 5' CAA CTC TGT GAT GGC TCC AG 3' | 88 |
| AIM6 | AP9 | 5' AGC AGG GTT CTG TTC AAG AC 3' | 89 |
| AIM6 | AP10 | 5' CCA TTG GGT GCT AGT CTC TC 3' | 90 |
| AIM6 | AP11 | 5' CAG CCA TGC TGT CCC AGC AG 3' | 91 |
| AIM6 | AP12 | 5' CTG GAC CTG AGG TAG CGC TG 3' | 92 |
| AIM6 | AP13 | 5' ATA ACC ACC CTG AGG CAC TG 3' | 93 |

Sequence analysis of the AIM6 clone sequence revealed the ORF represented in SEQ ID NO:151.

The sequence of AIM6 is presented in SEQ ID NO:6. The longest ORF in the AIM6 sequence is 1038 AA long and represented in SEQ ID NO:151.

The BLAST search did not reveal any sequences of known function with significant similarity to the AIM6 sequence.

7. Clone P2-10 (AIM7)

The internal sequencing primers synthesized and used to obtain the sequence of this clone were:

| | | | SEQ ID NO: |
|---|---|---|---|
| AIM7 | AP1 | 5' CCT GCA GGT CGA CAC TAG TG 3' | 94 |
| AIM7 | AP2 | 5' AAT TGG AAT GAG GAG GAC TG 3' | 95 |
| AIM7 | AP3 | 5' GCT CTA GAA GTA CTC TCG AG 3' | 96 |
| AIM7 | AP4 | 5' ATT GTA TGA CAA TGC ACC AG 3' | 97 |
| AIM7 | AP5 | 5' TCC ACA GAG GGC TTC ATC AC 3' | 98 |
| AIM7 | AP6 | 5' CCT GAC TGG CCT AAG CAC AG 3' | 99 |
| AIM7 | AP7 | 5' AAG CCT CAT AAC CAC CAG TG 3' | 100 |
| AIM7 | AP8 | 5' TGT CAA CGG TGA CAA GTG TG 3' | 101 |
| AIM7 | AP9 | 5' TTG TAC ACC AGC TGC AGG TC 3' | 102 |
| AIM7 | AP10 | 5' GGG TGT GGT GCA GAT GAG TC 3' | 103 |
| AIM7 | AP11 | 5' ATC ACA CTC TTA TAG CTC AG 3' | 104 |
| AIM7 | AP12 | 5' GTG GGA AGC TTT CCT CAG AC 3' | 105 |
| AIM7 | AP13 | 5' TGA TGA ACA TGG GCC TGG AG 3' | 106 |

The sequence of AIM7 is presented as SEQ ID NO:7. The longest ORF in the AIM7 sequence is 849 AA long and represented in SEQ ID NO:152.

The BLAST search revealed that this clone may be the Human Insulin-like Growth Factor II Receptor [Morgan et al. (1987) *Nature* 329:301–307] or the Human Cation-Independent Mannose 6-Phosphate Receptor mRNA [Oshima et al. (1988) *J. Biol. Chem.* 263:2553–2562]. The AIM7 sequence showed 99% identity to both sequences over 2520 nucleotides beginning with nt 12 of SEQ ID NO:7 and 99% similarity to the latter over the same span.

7. Clone P2-13 (AIM8)

The internal sequencing primers synthesized and used to obtain the sequence of this clone were:

| | | | SEQ ID NO: |
|---|---|---|---|
| AIM8 | AP1 | 5' CAT TGT GGA TGT ACT ACC AC 3' | 107 |
| *AIM8 | AP2 | 5' TGT GTT TTG CAA CCT GAG TG 3' | 108 |
| AIM8 | AP3 | 5' ATA GTG GCA CCA CTT ACG AG 3' | 109 |
| AIM8 | AP4 | 5' AAT TCT GCA ACG TGA TGG CG 3' | 110 |
| AIM8 | AP5 | 5' CAC AAG ATG CCT CGT CTG TG 3' | 111 |
| AIM8 | AP6 | 5' AAT CCG GAC AAG GTA CAG TC 3' | 112 |
| AIM8 | AP7 | 5' GCA CGA GTG GCA CAA GCG TG 3' | 113 |
| AIM8 | AP8 | 5' GCA AGC GTG TGG TGT CAG TG 3' | 114 |
| AIMB | AP9 | 5' TGT TTG AAC AGG CTC TGG AC 3' | 115 |
| AIM8 | AP10 | 5' CGG CAT GGC AAT GAG GAC AC 3' | 116 |
| AIM8 | AP11 | 5' AGG ACG AGA TGG ACC TCC AG 3' | 117 |
| AIM8 | AP12 | 5' CCC TCT GTC CTC TAG CCC AC 3' | 118 |

*Primers did not produce useable sequence data.

The sequence of AIM8 is presented as SEQ ID NO:8.

The longest ORF in the AIM8 sequence is 852 AA long and represented in SEQ ID NO:153.

The BLAST search did not reveal significant similarity of the AIM8 sequence to any sequence in the database.

9. Clone P2-14 (AIM9)

The internal sequencing primers synthesized and used to obtain the sequence of this clone were:

| | | | SEQ ID NO: |
|---|---|---|---|
| AIM9 | AP1 | 5' TCT TGA GGG GAC TGA CTC TG 3' | 119 |
| AIM9 | AP2 | 5' TGA GTG AGG AGG CAG ATG TC 3' | 120 |
| AIM9 | AP3 | 5' TGG CTT TGA AGA AAG AGC TG 3' | 121 |
| AIM9 | AP4 | 5' GCA AAA GAC CAG GCT GAC TG 3' | 122 |
| AIM9 | AP5 | 5' TGC AGC TCC TTG GTC TTC TC 3' | 123 |
| *AIM9 | AP6 | 5' GAT TCA CAG TCC CAA GGC TC 3' | 124 |

*Primers did not produce useable sequence data.

The sequence of AIM9 is presented as SEQ ID NO:9. No ORFS longer than 149 AA long were found in the AIM9 sequence.

The BLAST search did not reveal any sequences which had significant similarity to the AIM9 sequence.

10. Clone P2-15 (AIM10)

The internal sequencing primers synthesized and used to obtain the sequence of this clone were:

| | | | SEQ ID NO: |
|---|---|---|---|
| AIM10 | AP1 | 5' ATC TGG ATG AGG CGG TTG AG 3' | 125 |
| AIM10 | AP2 | 5' GGT CAC TCT CCG ACG AGG AG 3' | 126 |
| AIM10 | AP3 | 5' GGA TCC AAA GTT CGT CTC TG 3' | 127 |
| AIM10 | AP4 | 5' CGC TGT GTG TCT GAT CCC TC 3' | 128 |
| AIM10 | AP5 | 5' ATG AAG GTA AAC CCC GGG AG 3' | 129 |
| AIM10 | AP6 | 5' TGG TCT CTG GCT CTG AGC AC 3' | 130 |
| AIM10 | AP7 | 5' GCC TGG AGA AGC CCA GTC TG 3' | 131 |
| AIM10 | AP8 | 5' CAC ACT CTG GAC CGT TGC TG 3' | 132 |
| AIM10 | AP9 | 5' AAA GCT CCG CAG CCG CAG TG 3' | 133 |
| AIM10 | AP10 | 5' TCT TCC AGG AAG CTG CGG TC 3' | 134 |
| AIM10 | AP11 | 5' GAT GGT GGG GCA GCA TTG AG 3' | 135 |
| AIM10 | AP12 | 5' GTC ACC AGT GGT GCC TGC AG 3' | 136 |
| AIM10 | AP13a | 5' ACC TCA CGG TTG CCA ACC TG 3' | 137 |
| AIM10 | AP13b | 5' CGC AAC AGC GTC TCC CTC TG 3' | 138 |
| AIM10 | AP14 | 5' AGT ACC TTC ATA AGT TCT TC 3' | 139 |
| AIM10 | AP15 | 5' TCC CAG ACT TCA ACC TTC AC 3' | 140 |
| AIM10 | AP16 | 5' AAA CAT CTT CCC GGT CGG AC 3' | 141 |
| AIM10 | AP17 | 5' GCT GAG CAC CTT TAC CTC AC 3' | 142 |
| AIM10 | AP18 | 5' GAC GTC CGT CCG GGA AGA TG 3' | 143 |
| AIM10 | AP19 | 5' ACA CAG GAG ATG CAG GTC AC 3' | 144 |
| AIM10 | AP20 | 5' GAG TCT TCC ATG AAG AAC AG 3' | 145 |
| AIM10 | AP21 | 5' GCA GTG AGG AAG GTA AGG AG 3' | 146 |

*Primers did not produce useable sequence data.

The sequence of AIM10 is presented as SEQ ID NO:10. The longest ORF in the AIM10 sequence is 693 AA long and represented in SEQ ID NO:154.

The BLAST search did not reveal any sequences with significant similarity to the AIM10 sequence.

Thus, cloning the TRRE gene yielded nine clones, each of which encoded a protein having TRRE activity. These clones were designated 2-8, 2-9, 2-14, 2-15, P2-2, P2-10, P2-13, P2-14, and P2-15, which encode sequences designated AIM2, AIM3T3/AIM3T7, AIM4, AIM5, AIM6, AIM7, AIM8, AIM9, and AIM10, and shown in SEQ ID NOs:1 to 10. Each clone increases TRRE activity of COS-1 cells in vitro. Sequence analysis of these clones indicated that AIM3 may be homologous to *M musculus* 45S pre-rRNA gene; AIM5, Human eIF-5A transcription factor; and AIM7, Human Insulin-like Growth Factor II Receptor. Without wishing to be bound by any particular theory, the inventors suggest that some or all of these clones may be templates for RNAs or encode proteins which are involved in transcription and/or translation of TRRE. Alternatively, some or all of these factors may be involved in increasing the activity of TRRE (e.g., acting as an accessory protein).

Clonal DNA may be directly injected into test animals in order to test the ability of these nucleic acids to induce TRRE activity, counteract septic shock and/or affect tumor necrosis, as is described in detail in Examples 3 and 4.

Alternatively, proteins or RNA can be generated from the clonal DNA and similarly tested in animals.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention which is delineated by the appended claims.

What is claimed is:
1. An isolated polypeptide selected from the following:
   a) a protein with a complete amino acid sequence encoded in any of SEQ. ID NOs: 1, 5, 6, 8, 9, or 10;
   b) a fragment of said protein; and
   c) a fusion protein containing the protein or fragment according to a) or b);
wherein the polypeptide causes TNF receptor to be released from cells expressing the receptor.

2. The polypeptide of claim 1, which is a protein with a complete amino acid sequence encoded in any of SEQ. ID NOs: 1, 5, 6, 8, 9, or 10.

3. The polypeptide of claim 1, comprising a fragment encoded within any of SEQ. ID NOs: 1, 5, 6, 8, 9, or 10, which causes TNF receptor to be cleaved and released from cells expressing said receptor.

4. The polypeptide of claim 3, comprising said fragment fused to another amino acid sequence.

5. The polypeptide of claim 1, comprising an amino acid sequence contained in any of SEQ. ID NOs: 151, 153, or 154.

6. The polypeptide of claim 1, comprising the complete amino acid sequence in any of SEQ. ID NOs: 151, 153, or 154.

7. The polypeptide of claim 1, which is a metalloproteinase.

8. The isolated polypeptide of claim 1, which cleaves TNF receptor from the surface of cells.

9. The isolated polypeptide of claim 1, which causes release of the human p55 TNF receptor from cells expressing the receptor.

10. The isolated polypeptide of claim 1, which causes release of the human p75 TNF receptor from cells expressing the receptor.

11. The polypeptide of claim 1, selected from the following:
   a) a protein with a complete amino acid sequence encoded in SEQ. ID NO: 1;
   b) a fragment of said protein; and
   c) a fusion protein containing the protein or fragment according to a) or b);
wherein the polypeptide causes TNF receptor to be released from cells expressing the receptor.

12. The polypeptide of claim 1, selected from the following:
   a) a protein with a complete amino acid sequence encoded in SEQ. ID NO:5;
   b) a fragment of said protein; and
   c) a fusion protein containing the protein or fragment according to a) or b);
wherein the polypeptide causes TNF receptor to be released from cells expressing the receptor.

13. The polypeptide of claim 1, selected from the following:
   a) a protein with a complete amino acid sequence encoded in SEQ. ID NO: 6;
   b) a fragment of said protein; and
   c) a fusion protein containing the protein or fragment according to a) or b);
wherein the polypeptide causes TNF receptor to be released from cells expressing the receptor.

14. The polypeptide of claim 1, selected from the following:
   a) a protein with a complete amino acid sequence encoded in SEQ. ID NO: 8;
   b) a fragment of said protein; and
   c) a fusion protein containing the protein or fragment according to a) or b);
wherein the polypeptide causes TNF receptor to be released from cells expressing the receptor.

15. The polypeptide of claim 1, selected from the following:
   a) a protein with a complete amino acid sequence encoded in SEQ. ID NO:9;
   b) a fragment of said protein; and
   c) a fusion protein containing the protein or fragment according to a) or b);
wherein the polypeptide causes TNF receptor to be released from cells expressing the receptor.

16. The polypeptide of claim 1, selected from the following:
   a) a protein with a complete amino acid sequence encoded in SEQ. ID NO: 10;
   b) a fragment of said protein; and
   c) a fusion protein containing the protein or fragment according to a) or b);
wherein the polypeptide causes TNF receptor to be released from cells expressing the receptor.

17. An isolated polypeptide selected from the following:
   a) a protein with a complete amino acid sequence encoded in SEQ. ID NO:8;
   b) a fragment of said protein; and
   c) a fusion protein containing the protein or fragment according to a) or b);
wherein the polypeptide has metalloproteinase activity.

18. An isolated polypeptide selected from the following:
   a) a protein with a complete amino acid sequence encoded in SEQ, ID NO:9;
   b) a fragment of said protein; and
   c) a fusion protein containing the protein or fragment according to a) or b);
wherein the polypeptide has metalloproteinase activity.

19. A pharmaceutical composition, comprising the polypeptide of claim 1, in a suitable excipient.

20. A pharmaceutical composition, comprising the polypeptide of claim 17, in a suitable excipient.

21. A pharmaceutical composition, comprising the polypeptide of claim 18, a suitable excipient.

22. A method of causing enzymatic release of TNF receptor from a cell, comprising contacting the cell with a polypeptide according to claim 1.

23. A method of causing enzymatic release of TNF receptor from a cell, comprising contacting the cell with a polypeptide according to claim 11.

24. A method of causing enzymatic release of TNF receptor from a cell, comprising contacting the cell with a polypeptide according to claim 12.

25. A method of causing enzymatic release of TNF receptor from a cell, comprising contacting the cell with a polypeptide according to claim 13.

26. A method of causing enzymatic release of TNF receptor from a cell, comprising contacting the cell with a polypeptide according to claim 14.

27. A method of causing enzymatic release of TNF receptor from a cell, comprising contacting the cell with a polypeptide according to claim 15.

28. A method of causing enzymatic release of TNF receptor from a cell, comprising contacting the cell with a polypeptide according to claim 16.

29. A method of causing enzymatic release of TNF receptor from a cell, comprising contacting the cell with a polypeptide according to claim 17.

30. A method of causing enzymatic release of TNF receptor from a cell, comprising contacting the cell with a polypeptide according to claim 18.

31. A method of altering signal transduction from TNF into a cell, comprising contacting the cell with a polypeptide according to claim 1.

* * * * *